(12) United States Patent
Sintim et al.

(10) Patent No.: US 8,952,192 B2
(45) Date of Patent: Feb. 10, 2015

(54) PHOSPHORYLATED AND BRANCHED DIHYDROXY-PENTANE-DIONE (DPD) ANALOGS AS QUORUM SENSING INHIBITORS IN BACTERIA

(75) Inventors: Herman O. Sintim, Bowie, MD (US); William E. Bentley, Annapolis, MD (US); Varnika Roy, College Park, MD (US); Jacqueline Smith, District Heights, MD (US); Reza Ghodssi, Silver Spring, MD (US); Mariana Tsacoumis Meyer, Baltimore, MD (US)

(73) Assignee: University of Maryland, College Park, College Park, MD (US)

( * ) Notice: Subject to any disclaimer, the term of this patent is extended or adjusted under 35 U.S.C. 154(b) by 100 days.

(21) Appl. No.: 13/430,000

(22) Filed: Mar. 26, 2012

(65) Prior Publication Data

US 2012/0294900 A1   Nov. 22, 2012

Related U.S. Application Data

(60) Provisional application No. 61/467,228, filed on Mar. 24, 2011.

(51) Int. Cl.

| | | |
|---|---|---|
| C07C 69/16 | (2006.01) |
| C07C 235/80 | (2006.01) |
| C07C 49/337 | (2006.01) |
| C07D 307/46 | (2006.01) |
| A61K 31/12 | (2006.01) |
| A61K 31/121 | (2006.01) |
| A01N 35/02 | (2006.01) |
| C07F 9/09 | (2006.01) |
| C07C 317/24 | (2006.01) |
| C07C 49/82 | (2006.01) |
| C07C 205/45 | (2006.01) |
| C07C 49/17 | (2006.01) |
| A01N 43/08 | (2006.01) |
| C07C 69/28 | (2006.01) |
| A01N 37/12 | (2006.01) |
| A01N 35/04 | (2006.01) |
| C07F 9/38 | (2006.01) |
| A01N 57/12 | (2006.01) |
| C07D 241/42 | (2006.01) |
| C07D 405/04 | (2006.01) |

(52) U.S. Cl.
CPC .............. *C07C 317/24* (2013.01); *A01N 35/02* (2013.01); *C07F 9/091* (2013.01); *C07C 49/82* (2013.01); *C07C 205/45* (2013.01); *C07C 49/17* (2013.01); *C07C 49/337* (2013.01); *A01N 43/08* (2013.01); *C07C 69/28* (2013.01); *C07C 235/80* (2013.01); *A01N 37/12* (2013.01); *A01N 35/04* (2013.01); *C07F 9/3808* (2013.01); *A01N 57/12* (2013.01); *C07D 241/42* (2013.01); *C07C 69/16* (2013.01); *C07D 307/46* (2013.01); *C07D 405/04* (2013.01)
USPC ........... 560/264; 568/303; 568/306; 568/336; 568/381; 568/413; 549/488; 514/461; 514/547; 514/675; 514/676; 514/689; 514/690

(58) Field of Classification Search
USPC .......... 560/264; 568/303, 306, 336, 381, 413; 514/547, 675, 676, 689, 690, 461; 549/488
See application file for complete search history.

(56) References Cited

U.S. PATENT DOCUMENTS

| | | |
|---|---|---|
| 7,183,099 B2 | 2/2007 | Taga et al. |
| 7,326,542 B2 | 2/2008 | Bassler et al. |
| 7,547,726 B2 | 6/2009 | Miller et al. |
| 2004/0115245 A1 | 6/2004 | Jonker |
| 2006/0229259 A1 | 10/2006 | Miller et al. |
| 2010/0137249 A1 | 6/2010 | Wang et al. |
| 2011/0123586 A1 | 5/2011 | Bassler et al. |

OTHER PUBLICATIONS

Smith et al, Chemical Communications., 2009, (45), 7033-7035.*
Frezza et al, Tetrahedron Letters, 2005, 46(38), 6495-98.*
Kadirvel et al, Bioorganic & Medicinal Chemical Letters, 2007, 17(5), 1428-31.*
Kuroboshi et al, Bulletin of Chemical Society of Japan, 1990, 63(2), 428-37.*
Lowery, C.A. et al. An unexpected switch in the modulation of AI-2-based quorum sensing discovered through synthetic 4,5-dihydroxy-2,3-pentanedione analogues, J. Am. Chem. Soc. Jun. 25, 2008, vol. 130, pp. 9200-9201.
Meijler, M.M. et al. Inhibition of *Pseudomonas aeruginosa* quorum sensing by AI-2 analogs, Bioorganic and Medicinal Chemistry Letters, vol. 19, Mar. 9, 2009, pp. 3941-3944.
Roy, V. ey al. Synthetic Analogs tailor native AI-2 signaling across bacterial species, J. Am. Chem. Soc., Jul. 26, 2010, vol. 132, pp. 11141-11150.

* cited by examiner

*Primary Examiner* — Shailendra Kumar
(74) *Attorney, Agent, or Firm* — Hodgson Russ LLP

(57) ABSTRACT

Provided are compositions and methods for modulating quorum sensing in microbes. The compounds are AI-2 analogs and as such have structures similar to 4,5-dihydroxy-2,3-pentanedione that can act as agonists/antagonists of quorum sensing. The compounds are useful for modulating quorum sensing in bacteria and can be used in methods for prophylaxis or therapy of bacterial infections and for reduction of biofilms.

8 Claims, 32 Drawing Sheets
(10 of 32 Drawing Sheet(s) Filed in Color)

B) Processing of AI-2 into AI-2*

Me and Et phospho-AI-2 destabilizes LsrR-DNA inetractions (Agonist)

When C1 is greater than Et, phospho-AI-2 antagonizes teh action of phospho-AI-2 a) Linear and Branched C1-analogs b) Cyclic and aromatic C1-analogs

PHOSPHORYLATED AND BRANCHED DIHYDROXY-PENTANE-DIONE (DPD) ANALOGS AS QUORUM SENSING INHIBITORS IN BACTERIA

CROSS-REFERENCE TO RELATED APPLICATIONS

This application claims priority to U.S. provisional patent application No. 61/467,228, filed Mar. 24, 2011, the disclosure of which is incorporated herein by reference.

STATEMENT REGARDING FEDERALLY SPONSORED RESEARCH

This invention was made with government support under contract no. NSF EFR10735987 awarded by the National Science Foundation (NSF). The government has certain rights in the invention.

STATEMENT REGARDING COLOR DRAWINGS

The patent or application file contains at least one drawing executed in color. Copies of this patent or patent application publication with color drawing(s) will be provided by the Office upon request and payment of the necessary fee.

FIELD OF THE INVENTION

The present invention relates generally to the field of quorum sensing in microbes and more specifically to compounds and methods of using the compounds to modulate quorum sensing.

BACKGROUND OF THE INVENTION

Bacteria can exist as single entity as well as be part of a community of other bacteria (which could consist of same or different species of bacteria). In either lifestyle (free flowing or community), bacteria communicate with their neighbors via small molecules called autoinducers (a process called quorum sensing, QS). It is now appreciated that QS controls the expression of virulence factors or biofilm-associated genes in a variety of clinically important bacteria. AI-2 is termed a universal quorum sensing autoinducer and is used by a variety of bacteria, both pathogenic and human microbiota. Interception of AI-2 signaling with analogs at the synthesis level (LuxS), extracellular receptor (LuxP), transport of signal into bacteria (LuxB) have been proposed but compositions and methods for inhibition of AI-2 or processed AI-2 (such as phosphorylatedvAI-2) binding to intracellular receptors are poorly developed.

Bacteria that attach to surfaces can encase themselves in a self-synthesized hydrated matrix of polysaccharides and proteins to form slimy layers or biofilms. Biofilms mediate persistence and shield bacteria from hostile environments. These structured communities enable a multicellular existence that is distinct from planktonic forms. Biofilms are of high clinical relevance, as they exist in ~80% of human infections. Pathogens in biofilms can exhibit antibiotic tolerance ~1000 times higher than their planktonic counterparts. Antibiotic therapy, most effective against planktonic cells that slough off biofilms, is oftentimes unable to eradicate the biofilm itself. Thus, biofilm infections typically become chronic, leading to continual administration of antibiotics, which, in turn, contributes to the clinical challenge of antibiotic resistance. Further, modulation of specific bacteria, in the presence of other bacteria that also use AI-2 has been an unsolved challenge, and to date there has been no reported use of AI-2 antagonists to synergistically potentiate the activity of other antimicrobial agents.

Thus, there remains an ongoing and unmet need for new and improved compositions and methods for modulating the tactics that are used by bacteria that cause infection and/or undesirable biofilm formation. The present invention meets these and other needs.

BRIEF SUMMARY OF THE INVENTION

The present invention provides compounds and methods that relate to modulation of quorum sensing in bacteria. In various embodiments, a compound provided by the invention is a compound having the following structure:

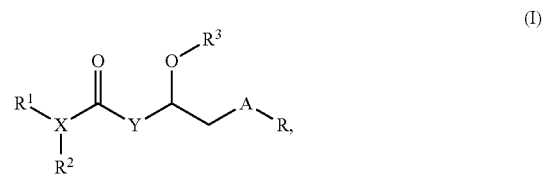

(I)

wherein R and $R^3$ are each independently a H, keto group, phosphonate group, sulfonate group, sulfoxide group, or carboxylate group; A is selected from the group consisting of: S, NH, $CH_2$, O, $CZ_2$, and CHZ, where Z is a halogen; Y is selected from the group consisting of: $CH_2$, $CZ_2$, and C=O, where Z is a halogen; X is selected from the group consisting of: CH, C—$CH_3$, and N; $R^1$ is selected from the group consisting of: H, $C_1$ to $C_{16}$ substituted or unsubstituted branched alkyl group, $C_1$ to $C_{16}$ substituted or unsubstituted linear alkyl group, $C_1$ to $C_{16}$ heterocyclic ring, and $C_3$ to $C_8$ carbocyclic ring, and $R^2$ is selected from the group of: H and $CH_3$, wherein, optionally, taken together $R^1$—X—$R^2$ form a $C_3$ to $C_8$ carbocyclic ring or heterocyclic ring, and the ring is, optionally, substituted, wherein, optionally, X is CH, $R^1$ is $CR^xR^y$, and $R^x$ is H or $C_1$ to $C_{16}$ substituted or unsubstituted linear alkyl group, $R^y$ is H or $C_1$ to $C_{16}$ substituted or unsubstituted linear alkyl group, and the bond between $R^1$ and X is a double bond, wherein, optionally, X is CH, and $R^1$ and X are each bonded to a single O to form an epoxide, wherein, optionally, A is a N, and taken together A and R form a 1,2,5-thiadiazolidin-3-one 1,1-dioxide, and wherein when A is O, X is CH, Y is C=O, $R^1$ is H, $R^2$ is H, $R^3$ is H, and R is not H or phosphonate, or when A is O, R is H, X is CH, Y is C=O, $R^2$ is H, $R^3$ is H, and $R^1$ is not $C_1$ to $C_6$ unsubstituted linear alkyl group.

In another embodiment, a compound provided by the invention has the following structure:

(V)

wherein X is selected from the group consisting of: CH and N; $R^1$ is selected from the group consisting of: H, $C_1$ to $C_{16}$ substituted or unsubstituted branched alkyl group, $C_1$ to $C_{16}$ substituted or unsubstituted linear alkyl group; $R^2$ is selected from the group consisting of: H, $C_1$ to $C_{16}$ substituted or unsubstituted branched alkyl group, and $C_1$ to $C_{16}$ substituted or unsubstituted linear alkyl group; $R^6$ is selected from the group consisting of: halogen, $NR^7R^8$, $OR^7$, and $SR^7$; $R^7$ is selected from the group consisting of: H, $C_1$ to $C_{16}$ substituted or unsubstituted branched alkyl group, $C_1$ to $C_{16}$ substituted or unsubstituted linear alkyl group, and $C_3$ to $C_8$ carbocyclic or heterocyclic ring; $R^8$ is selected from the group consisting of: H, $C_1$ to $C_{16}$ substituted or unsubstituted branched alkyl group, $C_1$ to $C_{16}$ substituted or unsubstituted linear alkyl group, and $C_3$ to $C_8$ carbocyclic or heterocyclic ring, and wherein, optionally, taken together $R^1$—X—$R^2$ form a $C_3$ to $C_8$ carbocyclic or heterocyclic ring, wherein the ring is, optionally, substituted.

In another embodiment, the invention provides a compound having the following structure:

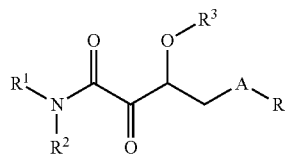

(VI)

wherein R and $R^3$ are each independently a H, keto group, phosphonate group, sulfonate group, sulfoxide or carboxylate group; A is selected from the group consisting of: NH, $CH_2$, $CF_2$, CHF and O; $R^1$ is selected from the group consisting of: $C_1$ to $C_{16}$ substituted or unsubstituted branched alkyl group and $C_1$ to $C_{16}$ substituted or unsubstituted linear alkyl group; $R^2$ is selected from the group consisting of: $C_1$ to $C_{16}$ substituted or unsubstituted branched alkyl group and $C_1$ to $C_{16}$ substituted or unsubstituted linear alkyl group, and wherein, optionally, taken together $R^1$—N—$R^2$ form a $C_3$ to $C_8$ heterocyclic ring, wherein the ring is, optionally, substituted.

Compositions, including pharmaceutical preparations, comprising compounds of the invention are provided. The compositions can further comprise other agents for use in inhibiting bacterial growth, such as antibiotics. The compositions can also comprise other known compounds which can modulate quorum sensing in bacteria.

The invention also provides method for modulating quorum sensing in a population of bacteria comprising contacting the population of bacteria with a composition comprising a compound of the invention. Also provided are non-living surfaces coated with a composition of the invention and methods of making such surfaces.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
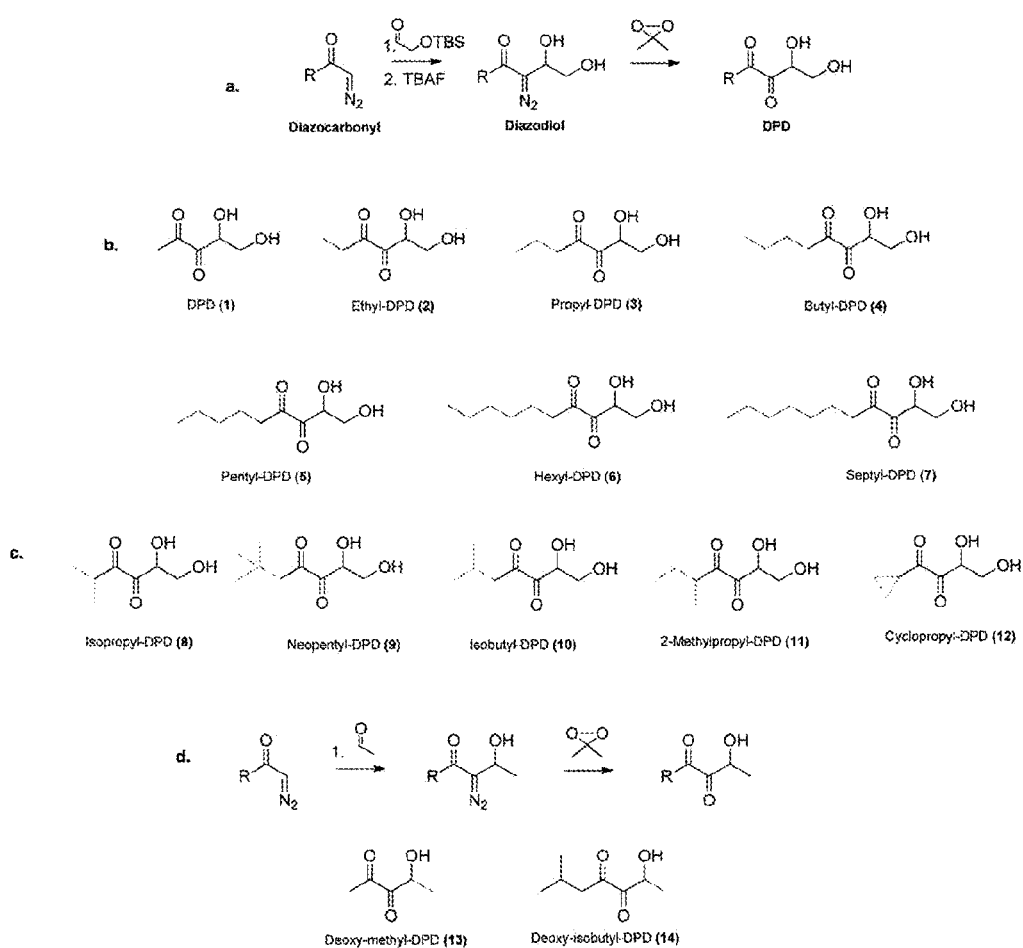
FIG. 1. Library of 14 C1-alkyl analogs. (a) Synthesis strategy for linear and branched DPD analogs. (b) Structures of the seven linear DPD analogs. (c) Structures of the five branched DPD analogs. (d) Synthesis strategy and structures for the deoxy-DPD analogs FIG. 2. Analogs inhibit native signaling in E. coli and S. typhimurium. AI-2 dependent β-galactosidase production in E. coli ZK126 pLW11 and S. typhimurium MET708 both (luxS+) in response to (a) linear analogs and (b) branched and deoxy analogs. (100% Native E. coli (ZK126) response=1103 Miller units and 100% native S. typhimurium (MET708) response=4478 Miller units.)

In this era of antibiotic resistant bacteria, treatment of unwanted microbial growth, such as microbial infections and biofilms, requires alternative antimicrobial therapies. Quorum sensing (QS) in bacteria is important for virulence phenotypes and biofilm formation. In the present invention we developed compounds based in part on the universal autoinducer AI-2. The compounds are useful for modulating QS in bacteria. Modulating QS in bacteria has a variety of benefits, including but not necessarily limited to enhancing the bactericidal activity of conventional antibiotics and inhibiting the formation and/or persistence of biofilms.

As used herein, the terms "QS-modulating" and "modulating QS" and "QS modulation" mean altering QS in one or more microbes. Modulating QS effected by contacting a bacterium and/or members of a bacterial population can be evidenced by occurrences which include but are not necessarily limited to (and which are not necessarily mutually exclusive) changes in expression of one or more genes involved in QS, changes in binding of one or more proteins involved in QS to a segment of bacterial DNA (such as binding of the transcriptional regulator LsrR to a portion of the lsr operon), changes in AI-2 binding to LsrR, changes in the amount of proteins involved in QS in a bacterium, changes in bacterial virulence, i.e., a lessening of virulence, disruption in the formation and/or integrity of a biofilm, and combinations thereof. In one embodiment, modulating QS is evidenced by reducing a biofilm. In another embodiment, modulating QS can be evidenced by disruption of extracellular polysaccharide material produced by bacteria in a biofilm. The QS modulation that is effected or is capable of being effected by a composition containing a compound of the invention is an alteration that would not be expected to occur in the absence of the compound.

With respect to the compounds provided by the invention, as used herein, "DPD analog" refers to compounds of similar structure to 4,5-dihydroxy-2,3-pentanedione that can act as agonists/antagonists of quorum sensing.

As used herein, "alkyl group" refers to branched or unbranched hydrocarbons. Examples of such alkyl groups include methyl groups, ethyl groups, butyl groups, nonyl groups, neopentyl groups, and the like. For example, the alkyl group can be a $C_1$ to $C_{16}$ alkyl group, including all integer numbers of carbons and ranges of numbers of carbons therebetween. The alkyl group can be substituted with groups such as, for example, a $C_3$ to $C_8$ carbocyclic or heterocyclic group, heteroatoms (e.g., N, S, O, etc.), halogen, silyl ether, organometallic complexes (e.g. Ruthenium Arenes of the type from Inorg. Chem. 2006, 45, 9006, incorporated herin by reference) and the like.

As used herein, "carbocyclic ring" refers to a cyclic compound having a ring in which all of the atoms forming the ring are carbon atoms. The carbocyclic ring can be aromatic or nonaromatic, and include compounds that are saturated, partially unsaturated, and fully unsaturated. Examples of such groups include cyclcopropyl, cyclobutyl, cyclopentyl, cyclohexyl, cycloheptyl, phenyl, 4-methoxyphenyl and the like. For example, the carbocyclic ring can be $C_3$ to $C_8$, including all integer numbers of carbons and ranges of numbers of carbons therebetween. The carbocyclic ring can be substituted with groups such as, for example, alkyl group, alkenyl group, alkynyl group, methoxy group, nitro group, halogen, amino group, $C_3$ to $C_8$ carbocyclic ring, $C_3$ to $C_8$ heterocyclic ring, and the like.

As used herein, "heterocyclic ring" refers to a cyclic compound having a ring where at least one of the atoms forming the ring is a heteroatom (e.g., O, N, S, etc.). The heterocyclic ring can be aromatic or nonaromatic, and include compounds that are saturated, partially unsaturated, and fully unsaturated. Examples of such groups include epoxy, triazolyl, tetrazolyl, pyridyl, pyrrolodinyl, tetrahydrofuryl and the like. For example, the heterocyclic ring can be $C_3$ to $C_8$, including all integer numbers of carbons and ranges of numbers of carbons therebetween.

As used herein "keto group" refers to

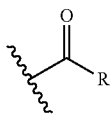

and R is $C_1$ to $C_{16}$ linear alkyl group. For example, the keto group can be

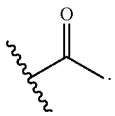

As used herein "halogen" refers to Cl, Br, F, and I.
As used herein "sulfonate group" refers to

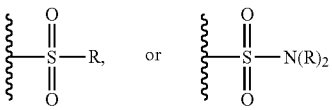

and can be bonded to C, O, N or S, where each R independently can be H, OH, $C_1$ to $C_{16}$ substituted or unsubstituted branched alkyl group, $C_1$ to $C_{16}$ substituted or unsubstituted linear alkyl group, $C_3$ to $C_8$ heterocyclic ring, or $C_3$ to $C_8$ carbocyclic ring and salts thereof. For example, the sulfonate group can be

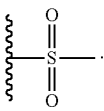

As used herein "sulfoxide group" refers to

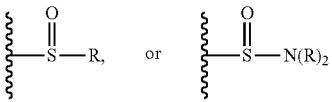

and can be bonded to C, O, N or S, where each R independently can be H, OH, $C_1$ to $C_{16}$ substituted or unsubstituted branched alkyl group, $C_1$ to $C_{16}$ substituted or unsubstituted linear alkyl group, $C_3$ to $C_8$ heterocyclic ring, or $C_3$ to $C_8$ carbocyclic ring and salts thereof.

As used herein "phosphonate group" refers to both esters and salts of phosphonates which can include phosphonamidates, phosphon bisamidates, phosphorothioates, and the like. For example, the phosphonate group can be

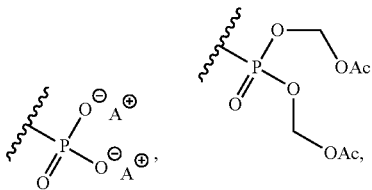

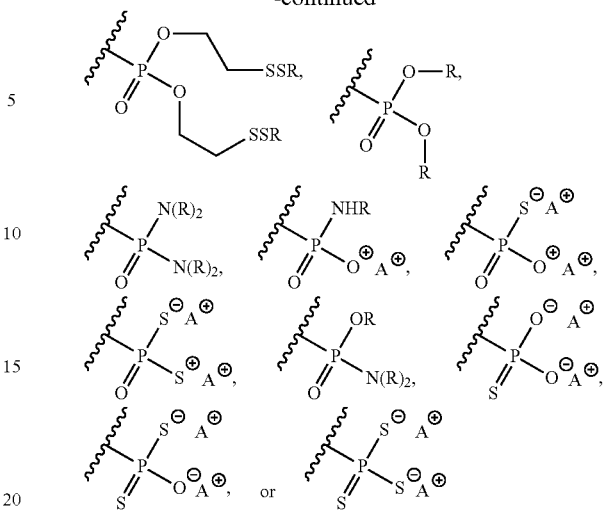

and can be bonded to C, O, N, or S, where $A^+$ is $H^+$, alkali metal cation (e.g., $Na^+$, $K^+$, etc.), divalent cation (e.g., $Ca^{2+}$, $Mg^{2+}$, $Zn^{2+}$, etc.), trivalent cation (e.g., $Al^{3+}$, etc.), ammonium cation, and the like. Each R independently can be H, $C_1$ to $C_{16}$ substituted or unsubstituted branched alkyl group, $C_1$ to $C_{16}$ substituted or unsubstituted linear alkyl group, $C_3$ to $C_8$ heterocyclic ring, $C_3$ to $C_8$ carbocyclic ring, a group that can be cleaved in vivo including, or a group that facilitates permeation into a cell.

As used herein "carboxylate" refers to the metal (e.g., $Na^+$, $K^+$, $NH_4^+$ etc.) salt of a carboxylic acid or a carboxylic acid.

In an embodiment, the DPD analogs have the following structure:

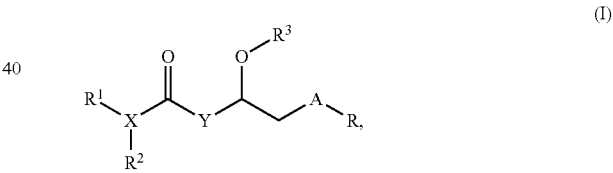

(I)

where R and $R^3$ are each independently a H, keto group, phosphonate group, sulfonate group, sulfoxide group, or carboxylate group; A is selected from the group consisting of: S, NH, $CH_2$, O, $CZ_2$, and CHZ, where Z is a halogen; Y is selected from the group consisting of: $CH_2$, $CZ_2$, and C=O, where Z is a halogen; X is selected from the group consisting of: CH, C—$CH_3$, and N; $R^1$ is selected from the group consisting of: H, $C_1$ to $C_{16}$ substituted or unsubstituted branched alkyl group, $C_1$ to $C_{16}$ substituted or unsubstituted linear alkyl group, $C_3$ to $C_8$ heterocyclic ring, and $C_3$ to $C_8$ carbocyclic ring; $R^2$ is selected from the group consisting of: H and $CH_3$. In certain embodiments, taken together $R^1$—X—$R^2$ form a $C_3$ to $C_8$ carbocyclic ring or heterocyclic ring. In certain embodiments, X is CH, $R^1$ is $CR^xR^y$, and $R^x$ is H or $C_1$ to $C_{16}$ substituted or unsubstituted linear alkyl group, $R^y$ is H or $C_1$ to $C_{16}$ substituted or unsubstituted linear alkyl group, and the bond between $R^1$ and X is a double bond. In an embodiment, X is CH, and $R^1$ and X are each bonded to O to form an epoxide. In an embodiment, where A is N, and taken together A and R form a 1,2,5-thiadiazolidin-3-one 1,1-dioxide. In another embodiment, A is O, X is CH, Y is C=O, $R^1$ is H, $R^2$ is H, $R^3$ is H, and R is not H or phosphonate, or A is O, R is H, X is CH, Y is C=O, $R^2$ is H, $R^3$ is H, and $R^1$ is not $C_1$ to $C_6$ unsubstituted linear alkyl group. In certain embodiments, R and $R^3$ are not H.

In an embodiment, the DPD analogs have the following structure:

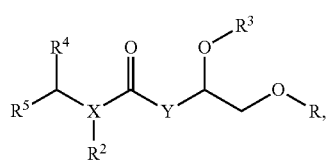
(II)

where R and $R^3$ are each independently selected from the group consisting of: H and keto group; X is selected from the group consisting of: CH, C—$CH_3$, and N; Y is selected from the group consisting of: $CH_2$, $CZ_2$, and C=O, where Z is a halogen; $R^2$ is selected from the group consisting of: H and $CH_3$; $R^4$ is selected from the group consisting of: $C_1$ to $C_{16}$ substituted or unsubstituted branched alkyl group, $C_1$ to $C_{16}$ substituted or unsubstituted linear alkyl group, $C_3$ to $C_8$ heterocyclic ring, and $C_3$ to $C_8$ carbocyclic ring; and $R^5$ is selected from the group consisting of: $C_1$ to $C_{16}$ substituted or unsubstituted branched alkyl group, $C_1$ to $C_{16}$ substituted or unsubstituted linear alkyl group, $C_3$ to $C_8$ heterocyclic ring, and $C_3$ to $C_8$ carbocyclic ring.

In an embodiment, the DPD analogs have the following structure:

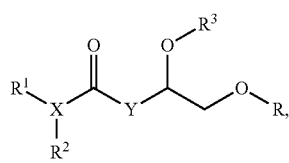
(III)

where X is selected from the group consisting of: CH, C—$CH_3$, and N; Y is selected from the group consisting of: $CH_2$, $CZ_2$, and C=O, where Z is a halogen; R and $R^3$ are each independently selected from the group consisting of: H, keto group and phosphonate group, and taken together $R^1$—X—$R^2$ form a $C_3$ to $C_8$ carbocyclic ring or heterocyclic ring. In certain embodiments, R and $R^3$ are not H.

In another embodiment, the DPD analogs have the following structure:

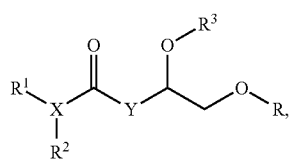
(III)

where X is selected from the group consisting of: CH, and N; Y is selected from the group consisting of: $CH_2$, $CZ_2$, and C=O, where Z is a halogen; R and $R^3$ are each independently selected from the group consisting of: H and keto group; $R^1$ is $C_1$ to $C_{16}$ substituted or unsubstituted linear alkyl group, and $R^2$ is H. In another embodiment, X is CH, $R^1$ is $CR^xR^y$, $R^x$ is H or $C_1$ to $C_{16}$ substituted or unsubstituted linear alkyl group, $R^y$ is H or $C_1$ to $C_{16}$ substituted or unsubstituted linear alkyl group, and the bond between $R^1$ and X is a double bond. In yet another embodiment, X is CH, and $R^1$ and X are each bonded to O to form an epoxide. In certain embodiments, R and $R^3$ are not H.

In an embodiment the DPD analogs have the following structure:

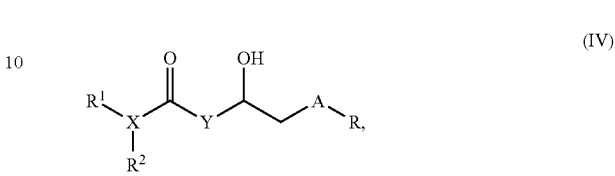
(IV)

where X is selected from the group consisting of: CH, C—$CH_3$, and N;
Y is selected from the group consisting of: $CH_2$, $CZ_2$, and C=O, where Z is a halogen;
A is selected from the group consisting of: S, NH, $CH_2$, O, $CZ_2$, and CHZ, where Z is a halogen;
R is selected from the group consisting of: keto group, phosphonate group, sulfonate group, sulfoxide group, and carboxylate group; $R^1$ is selected from the group consisting of: $C_1$ to $C_{16}$ substituted or unsubstituted branched alkyl group, $C_1$ to $C_{16}$ substituted or unsubstituted linear alkyl group, and $C_3$ to $C_8$ carbocyclic ring; $R^2$ is selected from the group consisting of: H or $CH_3$. In certain embodiments taken together $R^1$ and $R^2$ form a $C_3$ to $C_8$ carbocyclic ring or heterocyclic ring where the ring can be substituted or unsubstituted.

In certain embodiments, X is CH, $R^1$ is $CR^xR^y$, and $R^x$ is H or $C_1$ to $C_{16}$ substituted or unsubstituted linear alkyl group, $R^y$ is H or $C_1$ to $C_{16}$ substituted or unsubstituted linear alkyl group, and the bond between $R^1$ and X is a double bond. In certain embodiments, X is CH, $R^1$ and X are each bonded to O to form an epoxide. In another embodiment, A is N and taken together A and R form a 1,2,5-thiadiazolidin-3-one 1,1-dioxide. In certain embodiments, R is not H.

In an embodiment, the DPD analogs have the following structure:

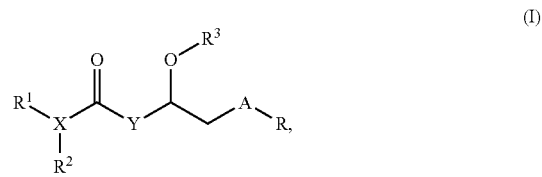
(I)

where A is $CH_2$, X is CH, $R^2$ is H, $R^1$ is $C_1$ to $C_{16}$ unsubstituted linear alkyl group, Y is C=O or $CZ_2$, where Z is halogen, $R^3$ is H, and R is a phosphonate group.

In an embodiment, the DPD analogs have the following structure:

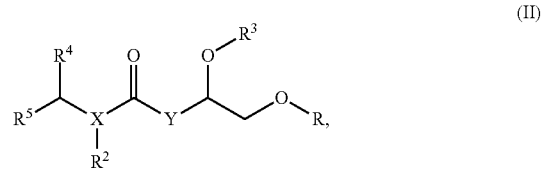
(II)

where X is CH, Y is C=O or $CZ_2$, where Z is halogen, R is H, keto group, or phosphonate group. $R^2$ is H, $R^3$ is H or a keto group, and $R^4$ and $R^5$ are $CH_3$. In certain embodiments, R and $R^3$ are not H.

In an embodiment, the DPD analogs have the following structure:

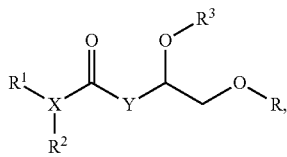

(III)

where Y is C=O or $CZ_2$, where Z is halogen, R is H, keto group, or phosphonate group and $R^3$ is H or a keto group, where taken together $R^1$—X—$R^2$ form a $C_3$ to $C_8$ carbocyclic ring or heterocyclic ring where the carbocyclic ring is a ring in which all of the atoms forming the ring are carbon atoms and the heterocyclic ring is a ring where at least one of the atoms forming the ring is a heteroatom. The ring can be substituted. Examples of substituents include, but are not limited to, methoxy, nitro, halogen, and the like. In certain embodiments, R and $R^3$ are not H.

In an embodiment, the DPD analogs have the following structure:

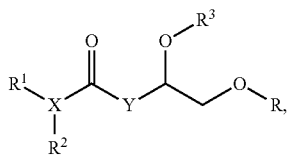

(III)

where X is CH, $R^1$ is $CR^xR^y$, $R^x$ is H or $C_1$ to $C_{16}$ substituted or unsubstituted linear alkyl group, and $R^y$ is H or $C_1$ to $C_{16}$ substituted or unsubstituted linear alkyl group, the bond between $R^1$ and X is a double bond or X is CH, $R^1$ and X are each bonded to O to form an epoxide. In this embodiment, Y is C=O or $CZ_2$, where Z is halogen, R is H or a keto group, and $R^3$ is H or a keto group. In certain embodiments, R and $R^3$ are not H.

In an embodiment, the DPD analogs have the following structure:

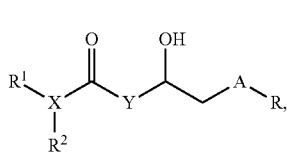

(IV)

where X is CH, Y is C=O or $CZ_2$, where Z is halogen, A is $CH_2$, R is a carboxylate, sulfonate group, or phosphonate group, $R^1$ is $C_1$ to $C_{16}$ unsubstituted linear alkyl group, and $R^2$ is H.

In an embodiment, the DPD analogs have the following structure:

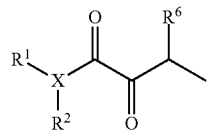

(V)

where X is CH or N, $R^6$ is selected from the group consisting of: halogen, $NR^7R^8$, $OR^7$, and $SR^7$; $R^1$ is selected from the group consisting of: H, $C_1$ to $C_{16}$ substituted or unsubstituted branched alkyl group, and $C_1$ to $C_{16}$ substituted or unsubstituted linear alkyl group; $R^2$ is selected from the group consisting of: H, $C_1$ to $C_{16}$ substituted or unsubstituted branched alkyl group, and $C_1$ to $C_{16}$ substituted or unsubstituted linear alkyl group; $R^7$ is selected from the group consisting of: H, $C_1$ to $C_{16}$ substituted or unsubstituted branched alkyl group, $C_1$ to $C_{16}$ substituted or unsubstituted linear alkyl group, and $C_3$ to $C_8$ carbocyclic or heterocyclic ring; and $R^8$ is selected from the group consisting of: H, $C_1$ to $C_{16}$ substituted or unsubstituted branched alkyl group, $C_1$ to $C_{16}$ substituted or unsubstituted linear alkyl group, and $C_3$ to $C_8$ carbocyclic or heterocyclic ring. In certain embodiments, taken together $R^1$—X—$R^2$ form a $C_3$ to $C_8$ carbocyclic ring or heterocyclic ring where the carbocyclic ring is a ring in which all of the atoms forming the ring are carbon atoms and the heterocyclic ring is a ring where at least one of the atoms forming the ring is a heteroatom. The ring can be substituted. Examples of substituents include, but are not limited to, methoxy, nitro, halogen, and the like.

In an embodiment, the DPD analogs have the following structure:

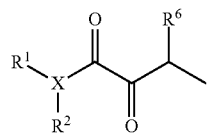

(V)

where X is CH or N, $R^6$ is OH; $R^1$ is selected from the group consisting of: H, $C_1$ to $C_{16}$ substituted or unsubstituted branched alkyl group, and $C_1$ to $C_{16}$ substituted or unsubstituted linear alkyl group; $R^2$ is selected from the group consisting of: H, $C_1$ to $C_{16}$ substituted or unsubstituted branched alkyl group, and $C_1$ to $C_{16}$ substituted or unsubstituted linear alkyl group.

In an embodiment, the DPD analogs have the following structure:

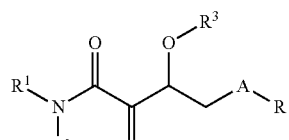

(VI)

where R and $R^3$ are each independently a H, keto group, phosphonate group, sulfonate group, sulfoxide group, or carboxylate group; A is selected from the group consisting of: S, NH, $CH_2$, O, $CZ_2$, and CHZ, where Z is a halogen; $R^1$ is selected from the group consisting of: $C_1$ to $C_{16}$ substituted or unsubstituted branched alkyl group and $C_1$ to $C_{16}$ substituted or unsubstituted linear alkyl group; $R^2$ is selected from the group consisting of: $C_1$ to $C_{16}$ substituted or unsubstituted branched alkyl group and $C_1$ to $C_{16}$ substituted or unsubstituted linear alkyl group. In certain embodiments, taken together $R^1$—N—$R^2$ form a $C_3$ to $C_8$ heterocyclic ring. The ring can be substituted. Examples of substituents include, but are not limited to, methoxy, nitro, halogen, and the like.

In an embodiment, the DPD analogs have the following structure:

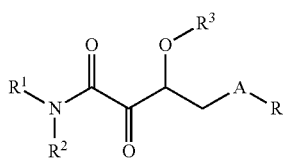

(VI)

where R and $R^3$ are each H; A is O; $R^1$ is selected from the group consisting of: $C_1$ to $C_{16}$ substituted or unsubstituted branched alkyl group and $C_1$ to $C_{16}$ substituted or unsubstituted linear alkyl group; $R^2$ is selected from the group consisting of: $C_1$ to $C_{16}$ substituted or unsubstituted branched alkyl group and $C_1$ to $C_{16}$ substituted or unsubstituted linear alkyl group. In certain embodiments, taken together $R^1$—N—$R^2$ form a $C_3$ to $C_8$ heterocyclic ring. The ring can be substituted. Examples of substituents include, but are not limited to, methoxy, nitro, halogen, and the like.

In various embodiments, the DPD analogs have the following structures:

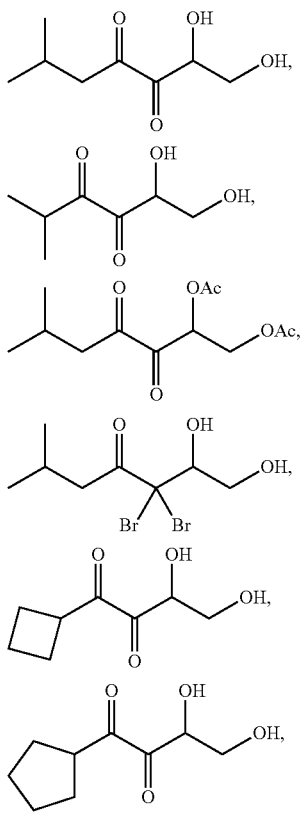

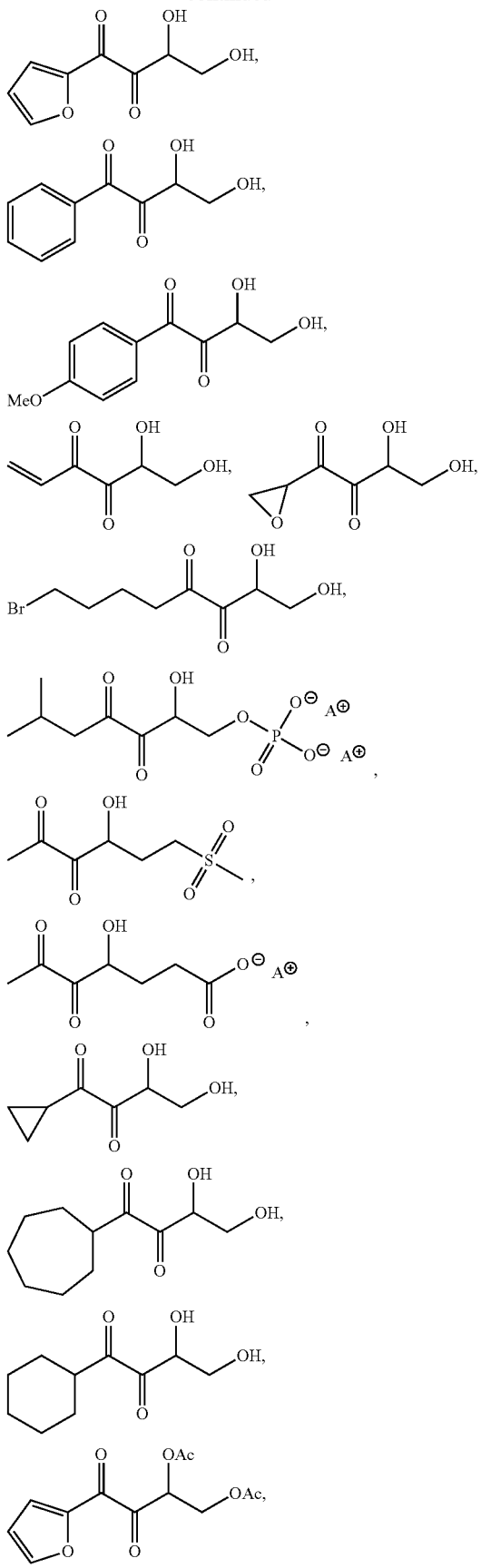

17
-continued

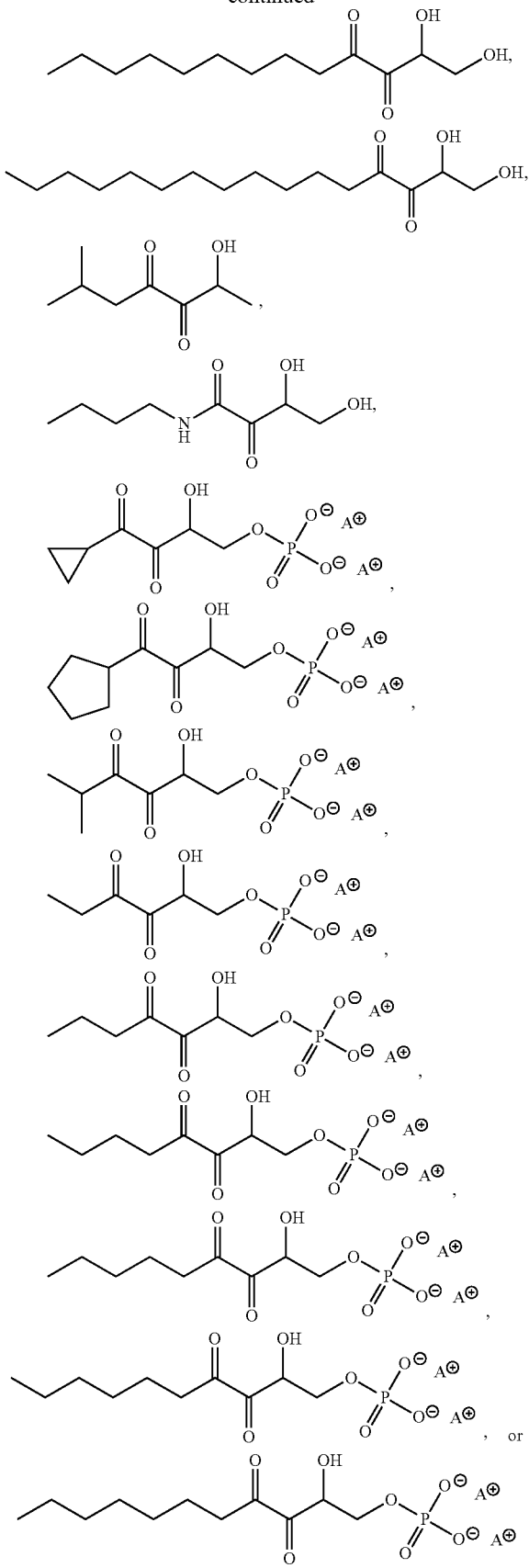

18 where A⁺ is H⁺, alkali metal cation (e.g., Na⁺, K⁺, etc.), divalent cation (e.g., Ca$^{2+}$, Mg$^{2+}$, Zn$^{2+}$, etc.), trivalent cation (e.g., Al$^{3+}$, etc.), ammonium cation, and the like.

In an embodiment, in the method the aforementioned compounds (structures I-VI) can be used in combination with one or more of the following six compounds (Group NN compounds):

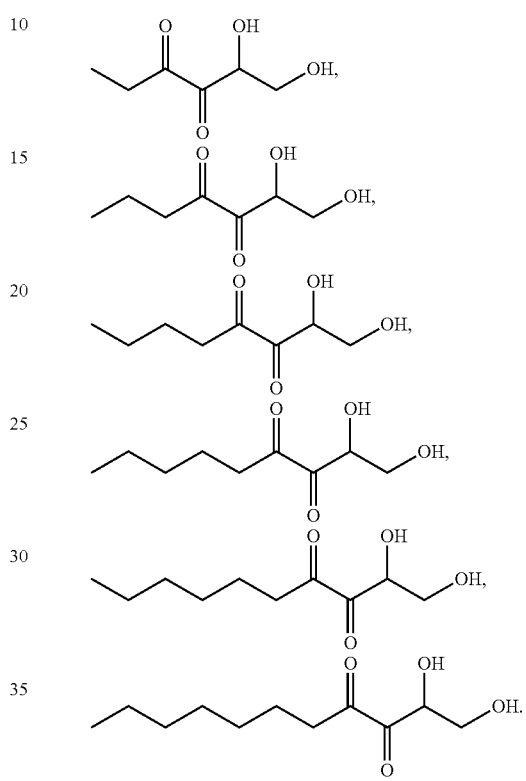

It will be recognized from the foregoing that the present invention contemplates classes of compounds and distinct compounds having the structures described above, which can be considered to be QS modulating compounds. The instant disclosure also contemplates excluding any distinct atom, moiety, group or class of moieties, compounds, or any class of compounds described herein from its scope. For example, in certain embodiments, any compound or class of compounds of the invention may be qualified with the proviso that it does not include any distinct atom, moiety, group or class of moieties, or compound or class of compounds. This does not preclude including previously known compounds in combination with novel compounds disclosed herein for compositions and methods of the invention. In one embodiment, a compound of the invention does not include any single, or any combination of compounds described in U.S. Pat. No. 7,547, 726, Janda et al. (J. Am. Chem. Soc., 2008, 130, 9200-9201), and Meijler et al. (Bioorg. & Med. Chem. Lett. 2009, 19, 3941-3944), from each of which the description of compounds and methods of making them are incorporated herein by reference.

The compounds of the invention can be used and/or formulated for use alone, or in any combination with one another, and in any combination with known QS-modulating compounds, and in any combination with any one or any combination of antibiotics. The invention also provides compositions which contain one or more of the QS-modulating compounds of the invention. Thus, the compositions can comprise only one QS-modulating compound, or they may comprise any combination of QS-modulating compounds described herein. The compositions can contain one or more antibiotic agents. In various embodiments, antibiotics that are members of classes such as aminoglycosides, beta lactams (with or without beta lactamase inhibitor such as clavulanic acid), macrolides, glycopeptides, polypeptides, cephalosporins, lincosamides, ketolides, rifampicin, polyketide, carbapenem, pleuromutilin, quinolones, streptogranin, oxazolidinones, lipopeptides, metals (including nanoparticles) can be use. Examples of specific antibiotics to be used are, but not limited to, gentamicin, silver (both colloidal and nanoparticle), vancomycin, Ampicillin, methicillin, Amoxicillin, Metronidazole (an antiprotozoal drug that can also be used to treat bacterial infections), Roxithromycin, Azithromycin, Levofloxacin, Cefixime, Ciprofloxacin, Moxifloxacin, Norfloxacin, Ofloxacin, Clarithromycin, Linezolid, Clindamycin, Doxycycline Hyclate, Tetracycline, Tigecycline, Aztreonam, Bacitracin, Trimethoprim-sulfamethoxazole, Daptomycin, Telithromycin, platensimycin, Rifampin, Isoniazid.

In various embodiments, the invention provides a composition that includes a QS-modulating component. The QS-modulating component can comprise, consist essentially of, or consist of one or a combination of the QS-modulating compounds described herein. The compositions can comprise additional agents. In some embodiments, a composition comprising a combination of at least one of the QS-modulating compounds of the invention and at least one antibiotic is provided. In certain embodiments, the combination of a compound of the invention and an antibiotic imparts the composition with the capability to synergistically affect bacteria, such as by synergistic reduction of a biofilm.

The compositions of the invention can include any compound selected from those described above as the structures I, II, III, IV, V and VI, and combinations thereof. A composition that includes at least one of these compounds can further include any one or any combination of the NN compounds described above. As noted, any of these compositions can further comprise an antibiotic, and may further comprise additional agents that are desirable for affecting microbes.

It will be apparent to those skilled in the art that, in various embodiments, a compound of the invention may constitute a type of pro-drug which can be metabolized once introduced into a microbe, and wherein a product of microbe metabolism of the pro-drug can be phosphorylated by a kinase that is endogenous to the microbe into which the compound is introduced. In certain embodiments, only the phosphorylated form of the compound is effective for modulating QS.

In another embodiment, the invention provides for the use of hydroxy methyl diketones wherein one terminal side contains a $CH_3$ group. Such compounds are expected to disrupt QS of non-Vibrio bacteria. Some representative compounds from this group are described in Roy, et al. J. Am. Chem. Soc. 2010 132(32):11141-50. The entire description of QS modulating compounds from Roy et al. is incorporated herein by reference.

The compounds of the invention can be provided as a pharmaceutical formulation. The pharmaceutical formulations provided by the invention can include pharmaceutically acceptable carriers with formulation ingredients such as salts, carriers, buffering agents, emulsifiers, diluents, excipients, chelating agents, fillers, drying agents, antioxidants, preservatives, binding agents, bulking agents, silicas, solubilizers, or stabilizers, or any combination thereof. Examples of pharmaceutically acceptable carriers can be found in: Remington: The Science and Practice of Pharmacy (2005) 21st Edition, Philadelphia, Pa. Lippincott Williams & Wilkins. The pharmaceutical preparations can formulated to be administered according to the method of the invention using any acceptable route. Thus, pharmaceutical preparations provided by the invention can be provided in the form of pills, tablets, coated tablets, lozenges, capsules, solutions, syrups, emulsions, suspensions, as aerosol mixtures, gels, sols, slurries, ointments, creams or tinctures, and can also include liposomes, microsomes, nanoparticles, and any other suitable vehicle for delivering a compound of the invention to an individual or to a non-living surface, as described further below.

In one embodiment, the invention provides a method for modulating QS in a microbe. The method comprises contacting a microbe with a compound of the invention. Contacting the microbe with the compound can include introducing the compound into the microbe. In one embodiment, the method involves contacting a population of microbes with a compound of the invention. In various embodiments, the population of microbes is comprised of either a homogeneous bacterial species, or is a mixed population of different bacterial species. In one embodiment, the population of bacteria comprises or consists of Gram-negative bacteria. In one embodiment, the population of bacteria is present in a biofilm. Biofilms are associations of microorganisms (of the same or different species) growing attached to a surface and generally producing a layer of extracellular polymers in which the microbial consortia are embedded in a protective environment. Biofilms can form on or within a living individual, as well as on non-living surfaces, as described further below. In one embodiment, the invention provides a non-living surface coated with a composition comprising a compound of structure I-IV and combinations thereof. The non-living surface can be a medical device surface as described further below. In a related embodiment, the invention provides a method of making a non-living surface that is resistant to biofilm formation. This comprises coating the surface with a composition comprising a compound of the invention.

In various aspects of the invention, methods are provided for modulating QS in a population of bacteria. The method comprises contacting a plurality of bacteria in the population with a composition of the invention. In various embodiments, the bacteria population in which QS is modulated is a mixed population of bacteria that includes 2 or more bacteria. In one embodiment, the population comprises or consist of at least three types of bacteria. In certain embodiments, the population of bacteria includes at least one type of bacteria selected from the genus consisting of, but not limiting to *Peptoniphilus, Staphylococcus, Pseudomonas, Enterobacter, Stenotrophomonas, Finegoldia, Serratia, Vibrio, Proteus, Salmonella, Clostridium, Alcaligenes, Brevundimonas, Streptococcus, Acinetobacter, Enterococcus, Pantoea, Corynebacterium, Bacillus, Paenibacillus, Eubacterium, Klebsiella, Xanthomonas, Ferrimonas, Finegoldia, Dendrosporobacter, RhodoPseudomonas, Veillonella, Haemophilus, Morganella, Dialister, Peptococcus, Delftia, Gordonia, Gemella, Fusobacterium, Varibaculum, Eikenella, Anaerococcus, Hydrogenophaga, Sphingomonas, Abiotrophia, Acidovorax, Prevotella, Bacteroides, Selenomonadaceae, Brevibacterium, Shewanella, Riemerella, Citrobacter, Bradyrhizobium*. Some of the specific species selected from the bacterial genus are, *P. agglomerans, P. niger, E. lenta, V. cambriense, A. europaeus, A. faecalis, A. lactolyticus, A. vaginalis, B. fragilis, F. magna, M. morganii, P. harei, C. novyi, V. atypical, A. para-adiacens, V. parvula, C. murliniae, H. segnis, E. avium, E. aerogenes, P. asaccharolyticus, E. cloacae, K oxytoca, D. acidovorans, D. invisus E. coli, V. cholerae, M. luteus, P. aeruginosa, B. burg-* dorferi, S. typhimurium, S. aureus, E. faecalis, A. baumannii, A. iwoffii, S. marcescens, P. mirabilis, K. pneumoniae, A. calcoaceticus, S. mutans, P. gingivalis, H. influenza, H. pylori, N. meningitides, N. gonorrhea, M. kansasii, B. anthracis, P. acnes, C. tetani, C. trachomatis, L. pneumophila, Y. pestis, B. abortus, F. tularensis, V. harveyi, and combinations thereof. In one embodiment, the population comprises E. coli, S. typhimurium, and P. aeruginosa.

In one embodiment, the invention provides for using a compound of the invention that can selectively modulate QS in certain bacteria, but not others. For instance, in one embodiment, the invention provides for administering a compound that can selectively modulate QS in pathogenic bacteria, but does not modulate QS in non-pathogenic and/or mutualistic bacteria that are generally considered neutral or beneficial to the individual. In one embodiment, the compound selectively modulates QS in a pathogenic bacterial species present in the gut of the individual, such as enterohemorrhagic E. coli. In another embodiment, the compound selectively modulates QS in a bacterial species that is an undesirable resident of the epidermis of the individual. Thus, certain types of bacteria can be targeted for selective QS modulation. For instance, as non-limiting examples, in a case where it would be desirable to use a compound that functions as a QS agonist in, for example, a bacterial population that is known or suspected to comprise E. coli and/or S. typhimurium, a composition comprising an ethyl-DPD or another analog thereof provided by the invention can be used. In a case where broad spectrum QS modulation is desired, a composition comprising isobutyl DPD or another analog of it provided by the invention can be used. If selective QS modulation for E. coli is desired, a composition comprising isopropyl DPD or another analog thereof provided by the invention can be used. In cases where it is desirable to use a compound of the invention as an antagonist, in general, the bacteria will comprise LsrR or orthologs/paralogs of LsrR (i.e., it is considered that the analog will function to make the repressor bind more tightly and/or more stably to the DNA), and in such cases, the analog should comprise an alkyl chain of $C_3$ or longer, such as $C_3$, $C_4$, $C_5$, $C_6$ or $C_7$.

It will be recognized that when modulating QS in a mixed population of bacteria, it is not necessarily vital to modulate QS in all species of bacteria in the mixed population. For example, if a mixed population of bacteria are present in a biofilm such that there are at least three bacterial species present, modulating QS in one or two species is expected to be adequate to reduce or inhibit the biofilm.

Illustrative and non-limiting examples of compounds and combinations thereof and bacteria for which they can be used for QS modulation are presented in Table 1.

TABLE 1

DPD Analogs and representative bacterial species affected

| DPD analog | V. harveyi[a] | S. mutans | S. typhimurium | E. coli | P. aeruginosa |
|---|---|---|---|---|---|
| Ethyl DPD | x | | | x | |
| Propyl DPD | x | | | x | |
| Butyl DPD | x | | | x | |
| Isobutyl DPD | x | | x | x | |
| Isopropyl DPD | | | | x | |
| Pentyl DPD | x | | | x | |
| Hexyl DPD | x | | | x | |
| Septyl DPD | | | | x | |
| Cyclohexyl DPD | x | | | x | |
| Cyclopentyl DPD | | | | x | |
| Cyclobutyl DPD | | x | | | |

TABLE 1-continued

DPD Analogs and representative bacterial species affected

| DPD analog | V. harveyi[a] | S. mutans | S. typhimurium | E. coli | P. aeruginosa |
|---|---|---|---|---|---|
| Furanyl DPD | | x | | | |
| Phenyl DPD | | | | | x |

In one embodiment, the invention provides a method for modulating QS in a population of bacteria resident in or on an individual in need of therapy for the bacterial population. The method comprises administering to the individual a composition comprising at least one compound of the invention in an amount effective to modulate QS in bacteria in the bacterial population in or on the individual. In certain embodiments, the compositions include at least one antibiotic agent. Such compositions can be used for therapeutic and/or prophylaxis of bacterial infections. Therapeutic approaches are used for an individual diagnosed with or suspected of having a bacterial infection. Prophylactic methods are used for individuals who are at risk for contracting bacterial infections, such as individuals with compromised immune systems or who are undergoing immunsuppresive treatment or are otherwise predisposed to bacterial infections.

Various methods known to those skilled in the art may be used to administer the compositions of the invention to an individual. These methods include but are not necessarily limited to intradermal, transdermal, intravenous, topical, intramuscular, intraperitoneal, intravenous, subcutaneous, oral, and intranasal routes. Further, it will be recognized by those of skill in the art that the form and character of the particular dosing regimen employed in the method of the invention will be dictated by the route of administration and other well-known variables, such as the age, sex, health and size of the individual, the type and severity of bacterial infection, or risk of bacterial infection, and other factors that will be apparent to the skilled artisan given the benefit of the present disclosure.

The invention provides compositions comprising compounds of the invention that are formulated for reducing and/or inhibiting the formation of a biofilm on a surface. Such compositions can include but are not necessarily limited to the pharmaceutical preparations described herein, but can also be formulated differently for use on non-living surfaces. The surfaces on which these compositions can be used include porous and non-porous surfaces. In one embodiment, the surface is a component of a device. In various embodiments, the device is a medical device. The invention accordingly includes a method of inhibiting or reducing a biofilm on a surface comprising applying a composition comprising a compound of the invention to a surface. The surface is thereby resistant to biofilm formation, and/or a biofilm on the surface is reduced by virtue of applying the composition.

Medical devices include but are not necessarily limited to any material or device that is used on, in, or through a subject's or patient's body, for example, in the course of medical treatment. Thus, medical devices include, but are not necessarily limited to such items as medical implants, wound care devices, blood bag systems, and drug delivery devices. The medical implants include, but are not limited to, urinary catheters, intravascular catheters, pacemakers, surgical pins, stents and shunts, prosthetic joints, endotracheal and gastrointestinal tubes, dentifrices, wound drain tubes, skin sutures, vascular grafts, implantable meshes, intraocular devices, heart valves, cochlear implants, etc. Wound care devices include but are not necessarily limited to general wound dressings, biologic graft materials, tape closures and dressings, meshes, sutures, and surgical incise drapes. Drug delivery devices include, but are not necessarily limited to needles, drug delivery skin patches, drug delivery mucosal patches and medical sponges. The invention is also suitable for inhibiting or reducing biofilms on devices or other items that are used within the body for short periods, such as tampons, sponges, surgical and examination gloves, contact lenses, toothbrushes, and intrauterine devices (IUDs). The invention provides for inhibiting and/or preventing medical device-associated bacterial infections and as such includes articles coated and/or impregnated with a QS modulating compound of the invention. Also provided are methods for making a medical device that is resistant to bacteria contamination and/or biofilm formation. The method comprises providing a medical device and coating and/or impregnating the medical device with a composition comprising one or more compounds of the invention. The application makes the device surface resistant to biofilm formation and/or reduces a biofilm on the device. Standard methods for coating and impregnating materials can be used. The materials may be fully or partially coated or impregnated with the compositions of the invention.

In other embodiments, the invention provides methods for inhibiting and/or disrupting biofilms on non-medical device surfaces, which include but are not necessarily limited to devices and parts of devices involved in areas where reduction of bacterial contamination and especially of biofilms is desirable. These surfaces include but are not necessarily limited to surfaces that are used in food processing, such as countertops, meat, fish, fruit, vegetable and liquid food and drink processing and/or dispensing surfaces and devices, food packaging devices and materials, and also such surfaces as children's toys, pet toys, non-human animal feed containers, surfaces in daycare centers, surfaces of hulls and other areas of waterborne vessels that are prone to biofilm formation, water handling and purification pipes and units, water or air-cooling systems, lavatories, automobile and airplane parts, floor coverings, sporting event surfaces such as wrestling or martial arts or tumbling mats, protective sporting goods equipment, and clothing items that are worn for extended periods of time, and any other surface whereupon undesirable biofilms are known to form. The same steps that are described for medical device use apply to making surfaces that are not part of medical devices resistant to bacteria contamination and/or biofilm formation in that the method comprises applying and/or impregnating such surfaces with a composition of the invention.

With respect to the role of compounds of the invention in modulating bacterial processes, it should be note that the AI-2 precursor 4,5-Dihydroxy-2,3-pentanedione DPD), is synthesized from S-adenosylhomocysteine (SAH) via a two-step enzymatic process catalyzed by MTA nucleosidase (Pfs) and S-ribosylhomocysteinase (LuxS). While synthase inhibitors, such as inhibitors of Pfs, can potentially alter both AI-1 and AI-2 signaling by disrupting signal generation, an alternative and equally important strategy is provided by the present invention. As discussed above, this involves disruption of AI-2 QS signaling by interfering with the signal reception and transduction processes. In this regard, the ubiquitous nature of AI-2 opens avenues for inhibiting or modulating AI-2 based QS among multiple pathogenic species simultaneously. For example, AI-2 modulates the growth of lethal bacteria such as *Bacillus anthracis*, and controls virulence in clinically important pathogens such as *V. cholerae* and *E. coli* O157 as well as a variety of other pathogenic bacteria. There was heretofore however, a paucity of small molecule antagonists of AI-2 quorum sensing.

In enteric bacteria such as pathogenic *E. coli* O157 and *S. enterica* Serovar Typhimurium, AI-2 is internalized and processed by various proteins. In these organisms, AI-2 is transported into the cells by an ABC cassette-like transporter, followed by phosphorylation via the kinase LsrK. The phosphorylated AI-2 binds to the transcriptional regulator (LsrR) and releases it from the lsr (luxS regulated) operon, thus de-repressing the system and allowing transcription of genes in the QS circuit. LsrR has been shown to play important roles in *E. coli* biofilm maturation, as well as regulating the expression of over 68 proteins in *E. coli*, including important virulence determinants. LsrR-like proteins are therefore in certain embodiments targets of the compounds of the present invention.

Without intending to be constrained by theory, it is considered that the antagonistic activity of $C_1$-alkyl analogs of AI-2 we report in the present invention is likely due to competitive binding to the LsrR transcriptional regulator. Unlike other bacterial kinases, LsrK from *E. coli* has broad substrate specificity and phosphorylates $C_1$-alkyl AI-2 analogs of different shapes and sizes, as also demonstrated herein. In *E. coli*, the majority of the phosphorylated AI-2 analogs compete with phospho-AI-2 for binding to LsrR. Interestingly, and again without intending to be bound by any particular theory, we believe we have discovered that lower alkyl chain AI-2 analogs ($C_1$ and $C_2$) destabilize the LsrR-DNA complex and promote lsr transcription whereas higher alkyl chain AI-2 analogs ($C_3$-$C_7$) stabilize Lsr-DNA complex and inhibit lsr transcription. The Lsr proteins in *S. typhimurium* and *E. coli* share high sequence and predicted structural homologies, yet the majority of AI-2 analogs that inhibited lsr expression in *E. coli* failed to do so in *S. typhimurium*; demonstrating both flexibility and specificity in QS circuitry. The present invention therefore demonstrates that, depending on the nature of the C1-alkyl chain, some AI-2 analogs can either quench QS in a variety of bacteria (broader-spectrum anti-QS) or in selected bacteria. Given the benefit of the present invention, those skilled in the art will recognize how to exploit the broader-spectrum and more selective actions by using the compounds of the invention in various combinations when desired. In this regard, the ability to modulate QS en mass or selectively has important clinical implications. For example in the gut, the microflora population is composed of various non-pathogenic and mutualistic bacteria that also utilize AI-2 signaling for non-pathogenic processes and therefore specifically targeting pathogenic bacterial species such as enterohemorrhagic *E. coli*, but not the symbionts, will allow the useful bacteria to coordinate their behavior in an energy efficient manner whereas the targeted pathogenic species will be out-of-sync and hence engage in "out-of-quorum" behaviors.

In the present invention, the ability of $C_1$-acyl AI-2 analog, isobutyl-DPD, to significantly inhibit the maturation of *Escherichia coli* biofilms grown in vitro is demonstrated. Using a novel microfluidic device that incorporates dynamic, real time measurements of biofilm density, it was also shown that a combinatorial approach wherein isobutyl-DPD is used with the antibiotic gentamicin, is quite effective in rendering near-complete clearance of pre-existing *E. coli* biofilms. Similarly, another AI-2 analog, phenyl-DPD, also used in combination with low levels of gentamicin resulted in clearance of pre-formed *Pseudomonas aeruginosa* biofilms. Clearance of pre-existing biofilms has remained a significant health care challenge; the present invention therefore demonstrates a new approach based on the combination of "quenching" QS signal transduction processes with traditional antibiotic treatment.

Selectively quenching the communication of a few bacteria, in the presence of several others in an ecosystem, using analogs of AI-2 is non-trivial due to the ubiquity of AI-2 processing receptors in many bacteria that co-exist. Herein, demonstrated is that wherein an AI-2 analog, isobutyl DPD (which is a QS quencher in both *Escherichia coli* and *Salmonella typhimurium*) is modified with ester groups, which get hydrolyzed once inside the bacterial cells, only QS in *E. coli*, but not in *S. typhimurium*, is inhibited. Such differences could be utilized to selectively target QS in specific bacteria amongst a consortium of other species that also use AI-2 signaling.

Linear and branched acyl analogs of AI-2 can selectively modulate AI-2 signaling in bacteria. Additionally, LsrK-dependent phosphorylated analogs are likely the inhibitory form against AI-2 signaling. In connection with this we synthesized an expanded and diverse array of AI-2 analogs, which included aromatic as well as cyclic $C_1$-alkyl analogs. Species-specific analogs that disrupted AI-2 signaling in *Escherichia coli, Salmonella typhimurium* are identified. Similarly, analogs that disrupted QS behaviors in *Pseudomonas aeruginosa* were found. Moreover, a strong correlation between LsrK-dependent phosphorylation of these acyl analogs and their ability to suppress QS was discovered in this invention. Significantly, we demonstrate that these analogs can selectively antagonize QS in single bacterial strains in a physiologically relevant polymicrobial culture. Furthermore, we have determined that dihydroxy-pentane-dione DPD-based antagonists of lsr expression can enter bacteria cells via both ABC transporter and alternative pathways, perhaps by secretion was revealed. The analogs are first phosphorylated by LsrK upon cell entry; it is the phospho-analog and not the unphosphorylated form which likely acts as lsr expression antagonist. In a trispecies synthetic ecosystem created from AI-2 responding *E. coli, S. typhimurium* and *V. harveyi*, both broader and narrow-spectrum anti-AI-2 QS activities from analogs were discovered. We also demonstrate the capability to achieve a synergistic reduction of biofilms using as illustrative embodiments a compound of the invention and a conventional antibiotic.

The following examples are presented to illustrate the present invention. They are not intended to limiting in any manner.

EXAMPLE 1

This Example provides a description of synthesis of a panel of C1-alkyl analogs.

Various linear (1-7 (FIG. 1)) and non-linear DPD analogs (8-12 (FIG. 1)) were prepared via a simple two-pot DPD synthesis. This expedient synthesis of DPD uses diazocarbonyls as an umpolung for the dione (dicarbonyl) of DPD. Aliphatic diazocarbonyls were readily generated from acid chlorides and diazomethane. The various diazocarbonyls were then reacted with a silyl-protected oxo-aldehyde under mild, catalytic DBU-conditions. Without isolation of the resulting adduct, the silyl group was deprotected with TBAF and the diazodiols were oxidized with dimethyl dioxirane to afford DPD analogs.

Initial investigations using the synthesized DPD analogs revealed that the analogs which acted as lsr antagonists were also phosphorylated by LsrK; suggesting that phospho-DPD analogs and not the unphosphorylated analogs might be the true antagonists. However, the possibility that residual unphosphorylated DPD analogs were also antagonists of lsr expression could not be excluded. DPD analogs ((13-14) FIG. 1) that lacked the primary hydroxyl unit were synthesized. Since these deoxy-DPD analogs cannot be phosphorylated, they would test if the phosphate moiety of AI-2 analogs was important for lsr antagonism.

Identifying Quorum Quenchers in Enteric Bacteria

Figure 10:
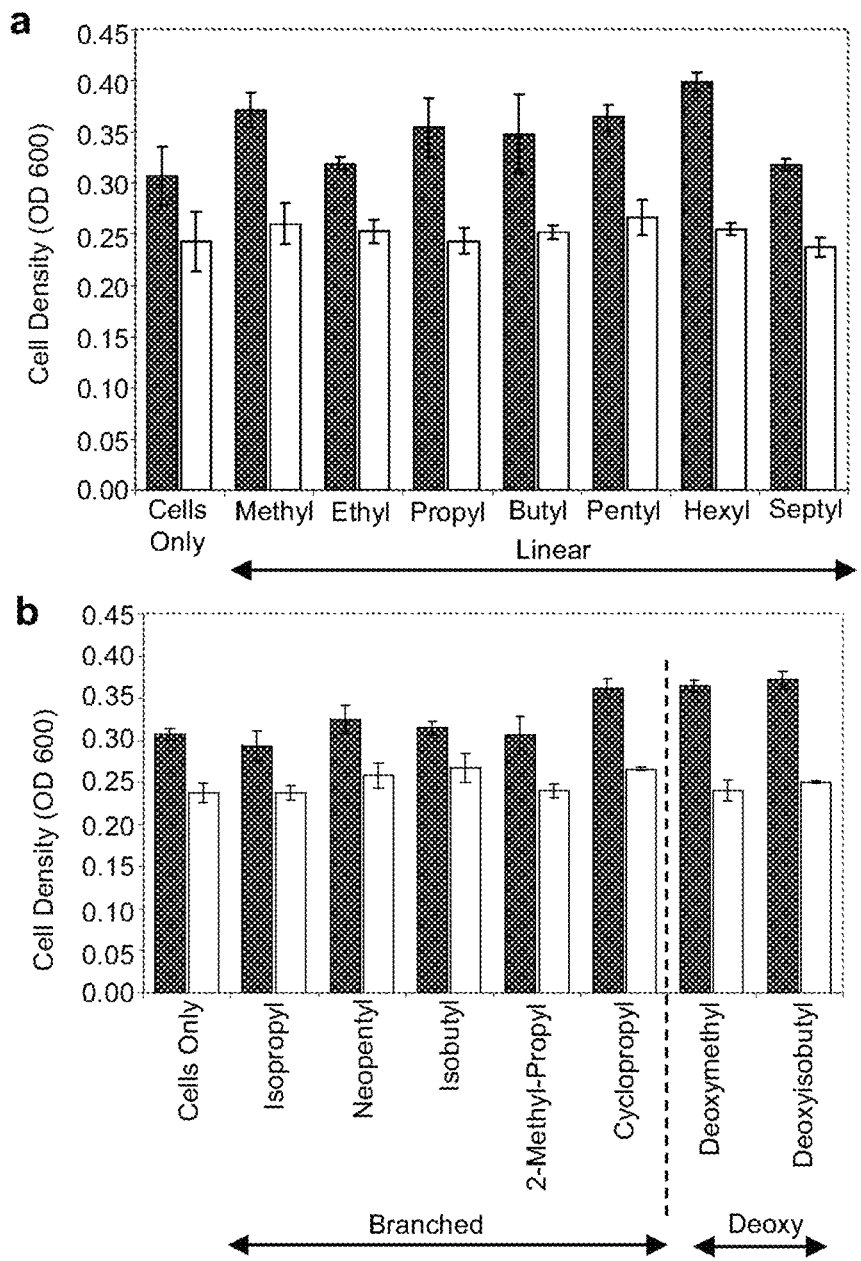
FIG. 10. Analogue Library is not bacteriostatic or bacteriocidal in E. coli and S. typhimurium Cell density ($OD_{600}$) of the cells remains unaffected after two hours of analogue treatment (a) linear analogues (b) branched and deoxy analogues, all added at 20 μM concentrations FIG. 11. Competitive inhibition of QS signaling by analogues in the presence of stoichiometric amounts of in vitro enzymatically synthesized AI-2 in E. coli and S. typhimurium; AI-2 dependent β-galactosidase production in E. coli LW7 pLW11 and S. typhimurium MET708 (both luxS−) and 20 μM in vitro synthesized AI-2 (a) linear analogues (b) branched and deoxy analogues all added at 20 μM concentrations.
Figure 11:
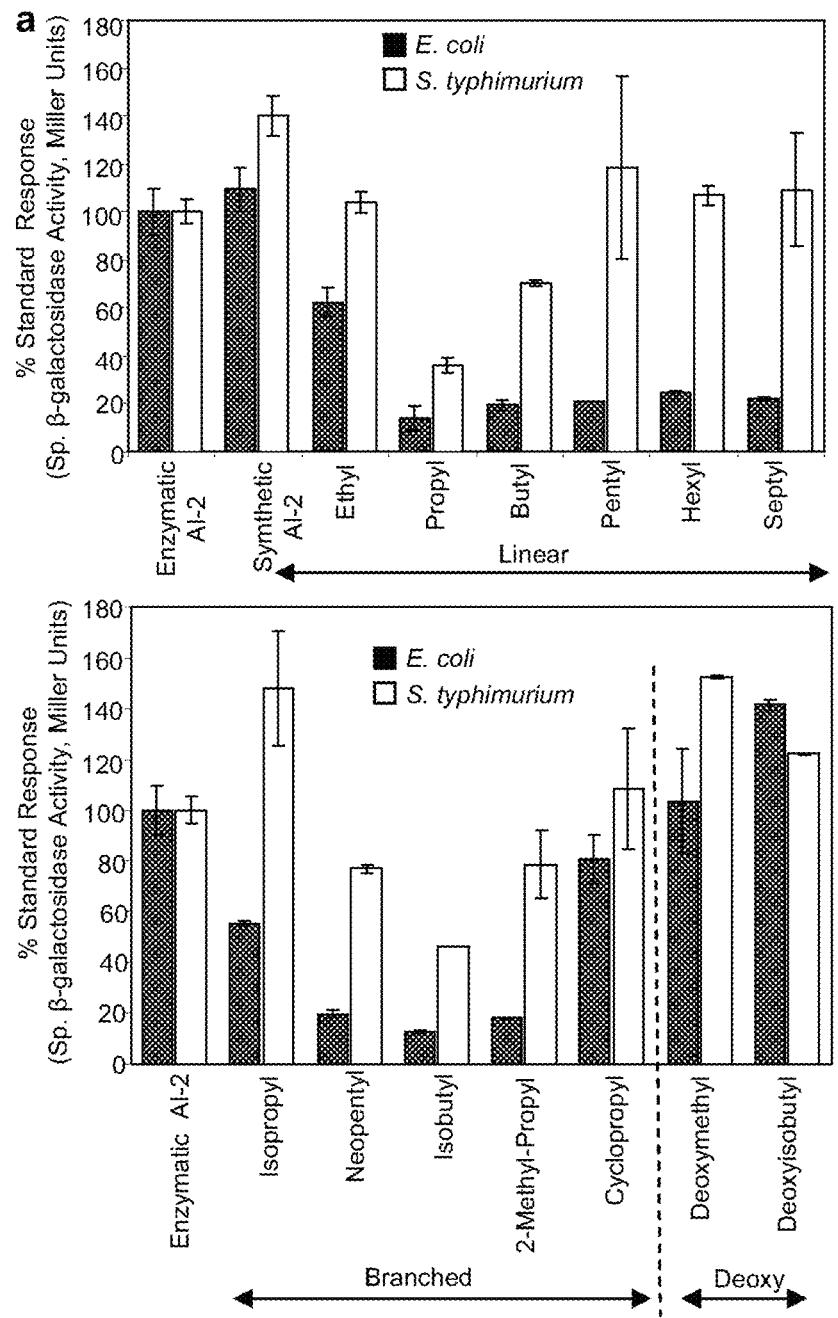

The panel of C1-alkyl analogs was screened to identify QS modulators in the enteric bacteria *E. coli* and *S. typhimurium*. Transcription of the QS associated lsr operon, by using lsr-lacZ reporter strains (Table 2) which produce β-galactosidase in response to added AI-2 was monitored. In order to first establish if the analogs were agonists or antagonists in the QS circuit, the analogs were incubated with *E. coli* LW7 pLW11 and *S. typhimurium* MET715 (FIG. 19a-b) both of which are luxS−. None of the analogs, except ethyl-DPD behaved as agonists for lsr expression. Previous studies investigating AI-2 antagonism in *P. aeruginosa* or in *S. typhimurium* were carried out using chemically synthesized AI-2 added to luxS− cells. In order to simulate the natural scenario where wild-type cells produce their own AI-2, the C1-alkyl analogs were tested on luxS+ cells (*E. coli* ZK126 pLW11 and *S. typhimurium* MET708 (Table 2). A minimum of three carbons in the C1 alkyl chain of DPD were required for QS antagonism was observed; propyl-DPD, and all larger linear alkyl chain analogs tested (FIG. 2a) caused a significant knockdown in native lsr expression in *E. coli*. However, for the linear analogs, only butyl-DPD caused a considerable QS response reduction in *S. typhimurium*. In the panel of non-linear DPD analogs (FIG. 2b), neopentyl-DPD, isopropyl-DPD and 2-methylpropyl-DPD caused substantial reduction of the *E. coli* QS response, but only isobutyl-DPD caused significant knocked down of the wild type lsr expression in both *E. coli* and *S. typhimurium* (FIG. 2b). The deoxy-C1-analogs did not significantly reduce the QS response in either *E. coli* or *S. typhimurium* (FIG. 2a,b). The same trends were obtained by adding a 1:1 ratio of enzymatically synthesized AI-2 and DPD analogs to the luxS− strains *E. coli* LW7 pLW11 and *S. typhimurium* MET715 (FIG. 11a-b). None of the tested DPD analogs were bacteriocidal or bacteriostatic as the OD600 values of *E. coli* ZK126 pLW11 and *S. typhimurium* MET708 in the presence and absence of the analogs were similar (FIG. 10). Though the QS circuitry of the enteric organisms, *E. coli* and *S. typhimurium* are homologous they respond differently to the DPD analogs. The *E. coli* QS circuitry is susceptible to being silenced by a variety of DPD analogs of different shapes and sizes whereas in *S. typhimurium*, only a handful of DPD analogs could antagonize the action of AI-2. This suggests that the QS processing machinery in *E. coli* is flexible (or promiscuous) in processing different DPD analogs whereas that of *S. typhimurium* seems to be more specific. Isobutyl-DPD emerged as an effective and non-species-specific quencher; causing significant lsr expression knockdowns in both *E. coli* and *S. typhimurium*.

Uptake and Phosphorylation of Analogs by *E. coli*

The knockdown of lsr expression by the linear DPD analogs in *E. coli* seemed to be dependent on the length of the alkyl chain; a minimum C3 alkyl chain is required for significant lsr expression knockdown. To determine if the ABC-like AI-2 transporter was absolutely essential for AI-2 transport and that no other alternative AI-2 transport systems or processes existed, DPD analogs were added to *E. coli* LW9 pLW11 cells (Table 2) that lack the known AI-2 transporter. This particular *E. coli* also lacks phospho-AI-2 degradation enzymes, LsrG and LsrF, and therefore was expected to be more sensitive to detecting the presence of processed AI-2 or analogs than a strain that contains both LsrF and LsrG. The analogs demonstrated similar knockdown trends as seen in the case of the (transporter+) strains (FIG. 3a-b). This demonstrates that both AI-2 and analogs can enter enteric bacteria via an alternative pathway; either through simple diffusion (e.g., from "AI-1 like" alkyl chains) or else their uptake could be mediated by an unknown transporter.

Figure 4:
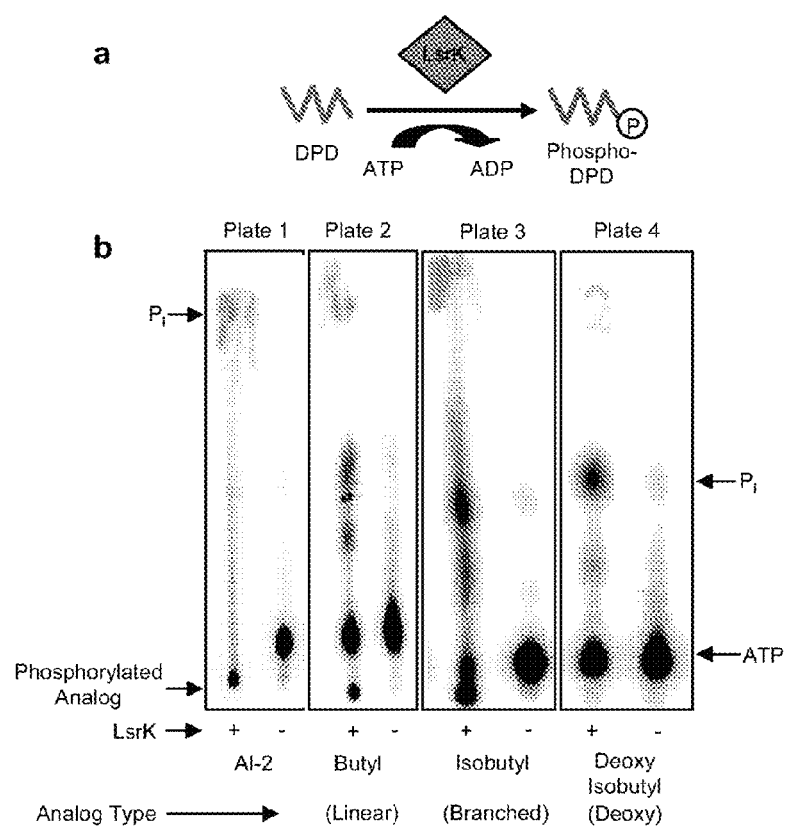
FIG. 4. In vitro phosphorylation of the analogs by LsrK a. Phosphorylation of DPD by LsrK in presence of ATP b. Representative thin layer chromatography (TLC) analysis of the LsrK mediated analog phosphorylation. Plate 1: Enzymatically synthesized AI-2. Plate 2: butyl-DPD. Plate 3: isobutyl-DPD. Plate 4: deoxy-isobutyl-DPD.
Figure 5:
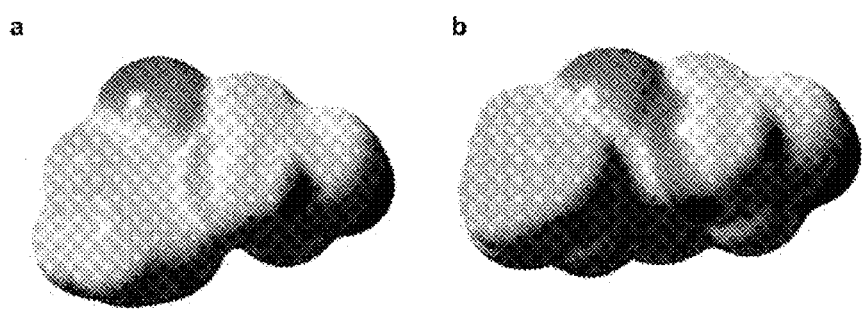
FIG. 5. Electrostatic potential map; the alkyl chain of the cyclopropyl-DPD analog is slightly more electron deficient than the isopropyl-DPD analog (a) cyclopropyl-DPD and (b) isopropyl-DPD. Both cyclopropyl (HOMO-3 orbital) and i-Pr (HOMO-4 orbital) stabilize the adjacent carbonyl group (LUMO) via hyperconjugation.
Figure 12:
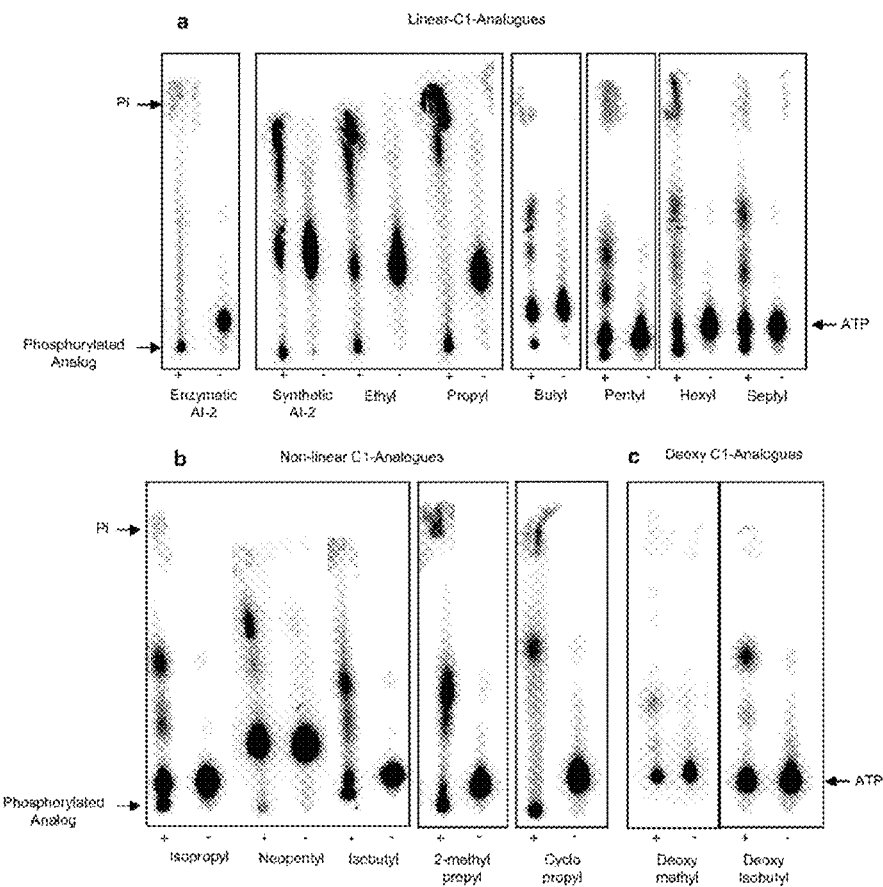
FIG. 12. In vitro phosphorylation of analogues by LsrK (a) Thin layer chromatography (TLC) analysis of the LsrK mediated reaction for 2 h. (a) linear (b) branched and (c) deoxy analogues.
Figure 13:
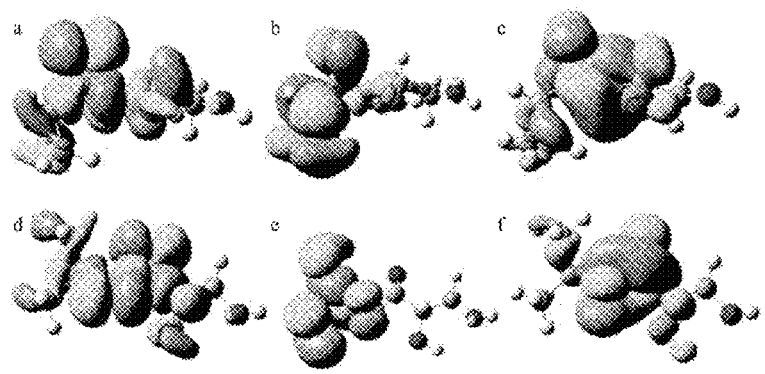
FIG. 13. Both cyclopropyl (HOMO-3 orbital) and i-Pr (HOMO-4 orbital) stabilize the adjacent carbonyl group (LUMO) via hyperconjugation. (a) HOMO of cyclopropyl-DPD (−0.23 eV); (b) HOMO-3 cyclopropyl-DPD (−0.30 eV); (c) LUMO cyclopropyl (−0.06 EV); (d) HOMO i-Pr-DPD (−0.24 eV); (e) HOMO-4 i-Pr-DPD (−0.34 eV); (f) LUMO i-Pr-DPD (−0.08 eV).

If the native AI-2 machinery is flexible, then analogs that are "AI-2 like" could be acted upon by the AI-2 processing machinery. In vivo, an important step that makes AI-2 functional in derepressing the lsr operon is the phosphorylation by the kinase LsrK. Thus, the ability of LsrK to phopshorylate the analogs was monitored by incubating the analogs with LsrK and an excess of ATP for 2 hours. All analogs, except the deoxy-C1-alkyl, were phosphorylated (FIG. 12). A representative TLC of DPD analog phosphorylation from each category (linear, branched and deoxy-C1-alkyl-DPD and enzymatically synthesized AI-2 as control) is shown in (FIG. 4) Radio-labeled phosphorylated DPD analogs have lower mobility than radio-labeled ATP. The deoxy-C1-analogs remained unphosphorylated as the terminal hydroxyl required for DPD phosphorylation was absent. Although isobutyl-DPD was found to be a potent QS "quencher", its unphosphorylated form, deoxy-isobutyl-DPD, was unable to silence the lsr operon as shown in (FIG. 2a-b). This provides circumstantial evidence that phosphorylation of an analog is most likely essential for its role in QS inhibition. Phosphorylation of a DPD analog is however not the only determinant of whether the analog can affect lsr expression. For example, cyclopropyl-DPD is phosphorylated by LsrK but is neither an lsr agonist nor antagonist. Significantly, isopropyl-DPD which has similar size and electrostatic molecular surface to cyclopropyl-DPD (see FIG. 5) is both phosphorylated by LsrK and acts as a partial antagonist of lsr expression. Cyclopropyl-DPD is similar in size/shape to isopropyl-DPD but the hydrogen bonding capability of the carbonyl moiety in cyclopropyl-DPD is slightly different from that of isopropyl-DPD. The cyclopropyl substituent can stabilize the carbonyl moiety better than the isopropyl alkyl group. DFT calculations (FIG. 13) reveal that although the highest occupied molecular orbital HOMO of both cyclopropyl-(HOMO-3) and isopropyl-(HOMO-4) DPD are close in energy to the carbonyl lowest unoccupied molecular orbital (LUMO) energies, the orbital symmetry of cyclopropyl HOMO-3 is more similar to the carbonyl LUMO than that of isopropyl HOMO-4 and carbonyl LUMO.

Figure 14:
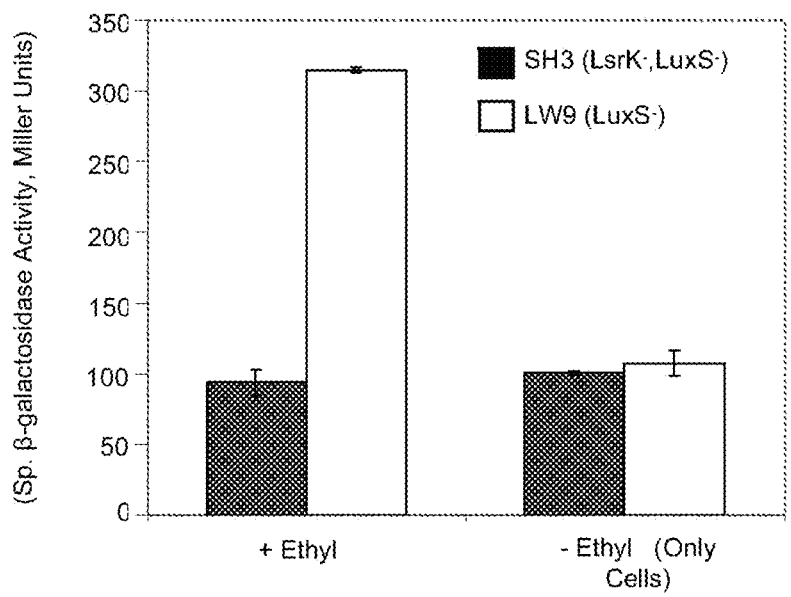
FIG. 14. Ethyl-DPD requires in vivo phosphorylation to function as an agonist of the QS response; SH3 (lsrK⁻, luxS⁻) and LW7 (lsrK⁻) are incubated in the prescence and absence of 20 μMethyl-DPD and the AI-2 dependent β-galactosidase response is quantified.
Figure 15:
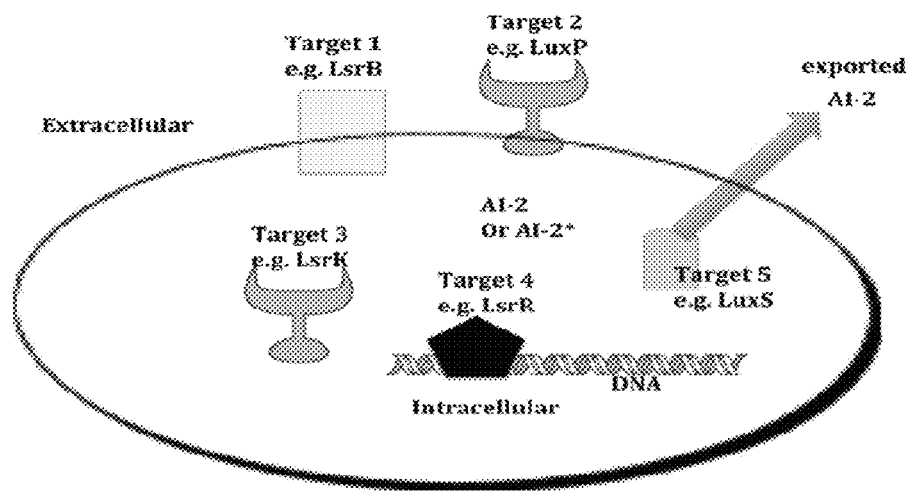
FIG. 15. Inhibition of AI-2-mediated quorum sensing at different targets.
Figure 16:
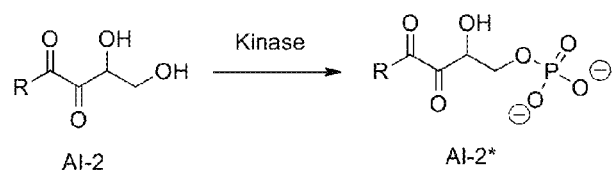
FIG. 16. Synthesis of phosphorylated analogs of DPD using LsrK (kinase).
Figure 17:
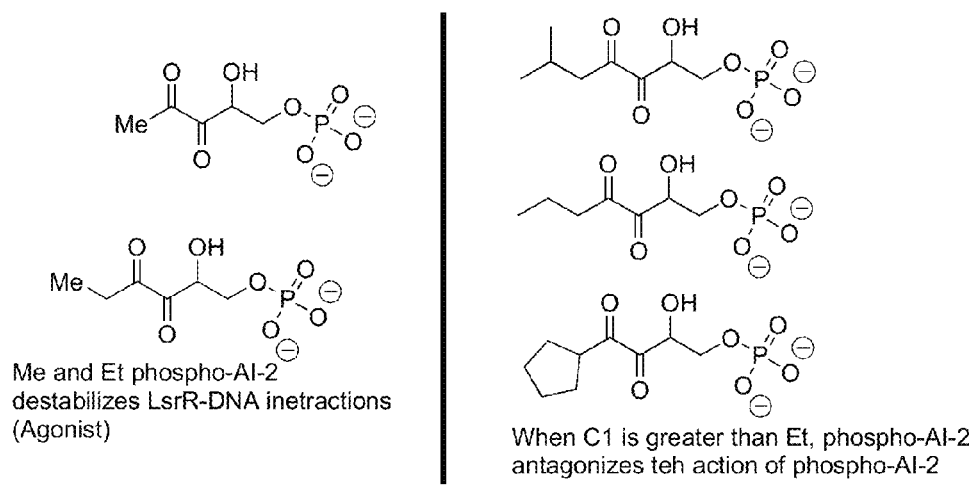
FIG. 17. Increasing the C1 size (greater than ethyl group) converts a phospho DPD-like molecule into an antagonist.

Ethyl-DPD also acts as a QS circuit agonist in *E. coli* but only in the presence of in vivo LsrK; in a LsrK knockout strain, ethyl-DPD did not initiate lsr transcription (FIG. 14). This suggests that the phosphorylation of DPD analogs by LsrK inside the bacterial cell is important for them to effect the lsr QS circuit; either as agonists or antagonists. The phosphate moiety in phospho-AI-2 and analogs, therefore, seem important for binding to LsrR, but it appears that the stabilization of LsrR/DNA complex is governed by the $C_1$ alkyl chain ($C_3$ is believed to be the minimum requirement).

Species-Specific and Species-Nonspecific Quorum Quenchers in a Synthetic Ecosystem To investigate the effect of the DPD analogs in a mixed bacterial environment, a synthetic ecosystem composed of three different bacterial populations was assembled. Specifically, *S. typhimurium* MET708, *V. harveyi* BB170 and *E. coli* W3110 (pCT6), each luxS+ (Table 2), and each producing their native AI-2 were co-cultured in the same tubes. By design, each species was selected so that a different reporter probe would indicate the specific bacterium's QS response: *S. typhimurium* (MET708) expresses β-galactosidase; *V. harveyi* (BB170) elicits bioluminescience; and *E. coli* (W331) are engineered to synthesize GFP. In this way, their responses can be differentiated and quantified in response to AI-2.

Figure 2:
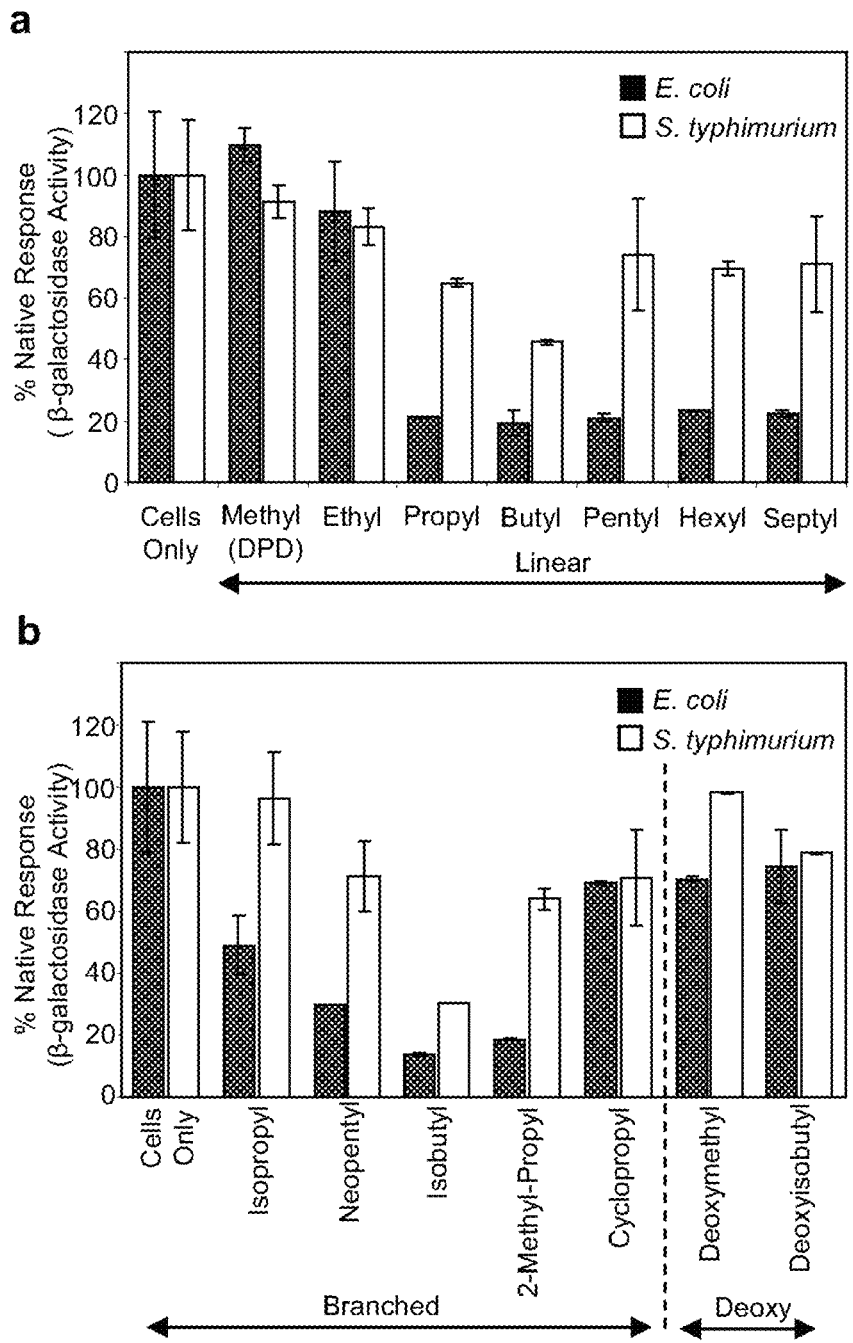
Figure 6:
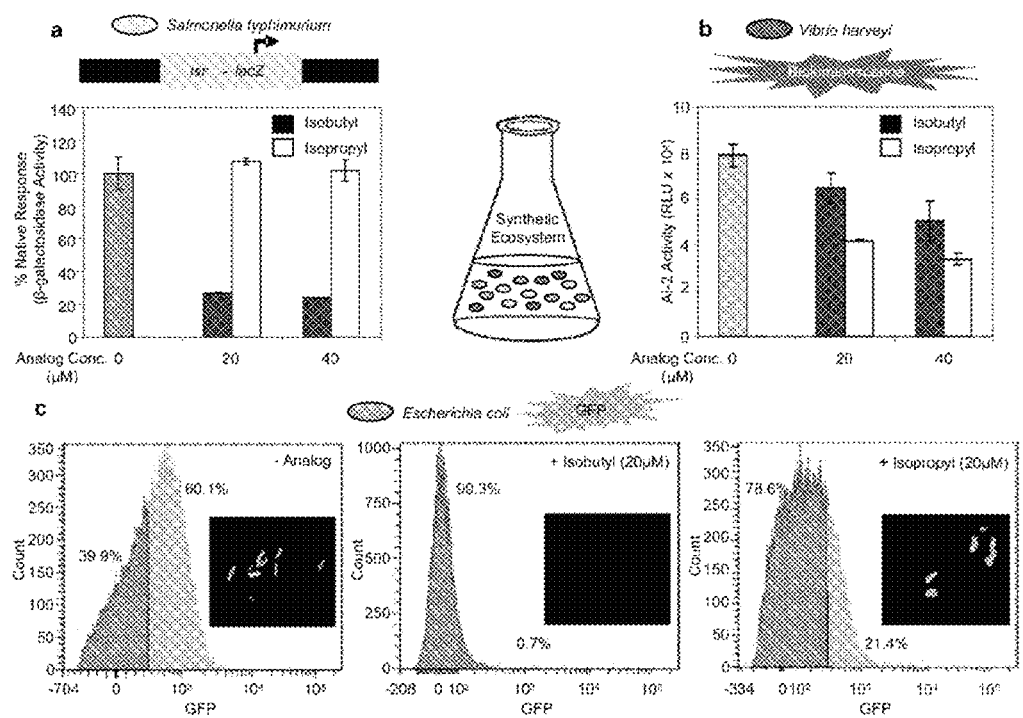
FIG. 6. Analogs inhibit native signaling in a trispecies synthetic ecosystem: (a) AI-2 dependent β-galactosidase production in S. typhimurium MET708 (100% Native S. typhimurium response in trispecies culture=1063 Miller units). (b) AI-2 dependent bioluminescence production in V. harveyi BB170 and (c) AI-2 dependent GFP induction in E. coli W3110 pCT6 (all strains are luxS+) in response to isobutyl-DPD and isopropyl-DPD.

Results shown in FIG. 2 demonstrated that isobutyl-DPD was able to suppress QS effectively in pure cultures of *E. coli* and *S. typhimurium*, while isopropyl-DPD selectively caused lsr suppression in *E. coli*. Therefore, these analogs were selected to monitor their specificity in the trispecies co-culture environment. Upon addition of isobutyl-DPD, *S. typhimurium*'s β-galactosidase's activity sharply decreased 4-fold while isopropyl-DPD was unable to cause any reduction in the *S. typhimurium* response (FIG. 6a). These trends were similar to those observed in pure culture studies. Then, isobutyl-DPD also decreased bioluminescence in *V. harveyi* grown in LM media by 33% at 40 µM, while isopropyl-DPD decreased bioluminescence in *V. harveyi* by 50% at both 20 µM and 40 µM (FIG. 6b). Of note, antagonism of bioluminescence in *V. harveyi* could not be observed when the bacteria were grown in AB media. It is important to note that the AI-2 uptake and processing machinery in *V. harveyi* are distinctly different from the enteric organisms *E. coli* and *S. typhimurium*. In *V. harveyi*, AI-2 binds to cell surface bound receptor LuxP which, in turn, recognizes a boronated form of AI-2; the QS signal is transduced through phospho-relay mechanisms whereas in *E. coli* or *S. typhimurium* AI-2 is first internalized and processed by lsr machinery before eliciting a QS response.

To ascertain the extent of QS signaling and quenching, the distribution of lsr expression in an *E. coli* population using AI-2 stimulated GFP expression and flow cytometry was monitored. In the absence of isobutyl-DPD, 60.7% of the population was QS positive (green). After the addition of isobutyl-DPD, QS positive cells were reduced to only 0.7%. Isopropyl-DPD only partially decreased the QS response to 21.4% of cells (FIG. 6c).

The results presented in this Example show that of the panel of DPD analogs, ethyl-DPD acts as a QS circuit agonist in *E. coli* and *S. typhimurium*. A variety of DPD analogs caused inhibition of native QS signaling in *E. coli*; butyl-DPD and isobutyl-DPD significantly inhibited signaling in the homologous QS circuit of *S. typhimurium*. Alignment studies (using protein blast) reveal that both *E. coli* and *S. typhimurium* LsrR proteins show significant homology (77% identical sequences). The 30 bp putative LsrR binding site in *E. coli* was aligned to the respective promoter region in *S. typhimurium* using Clustal W and showed 83% homology. Secondary and tertiary structure predictions show that LsrR from both *E. coli* and *S. typhimurium* have similar folds.

Figure 7:
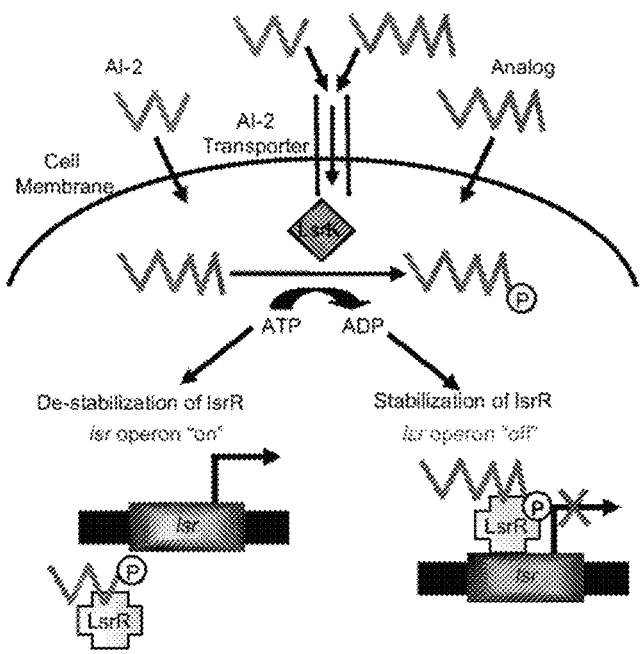
FIG. 7. Scheme for QS inhibition by a DPD analog in E. coli Analog/AI-2 enters the cell via the Lsr transporter or diffusise into the cell independent of the transporter. Analog needs to be phosphorylated by LsrK to function as an antagonist in the QS circuit. Phospho-analog also needs to compete with phosphor-AI-2 for binding to the repressor protein (LsrR) to repress lsr expression.
Figure 8:
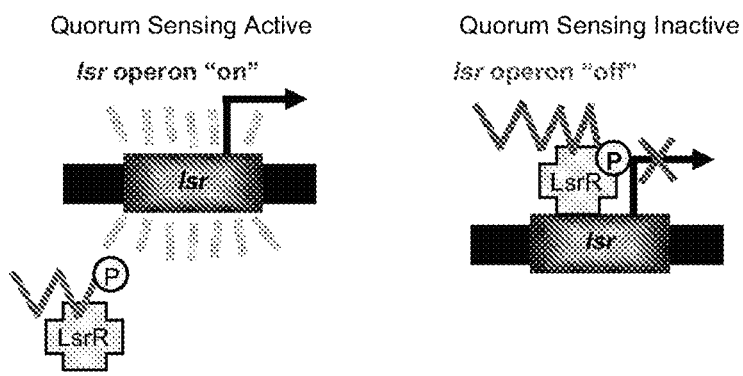
FIG. 8. $C_1$=methyl or ethyl leads to lsr expression whereas $C_1 \geq$ propyl leads to lsr expression off.
Figure 9:
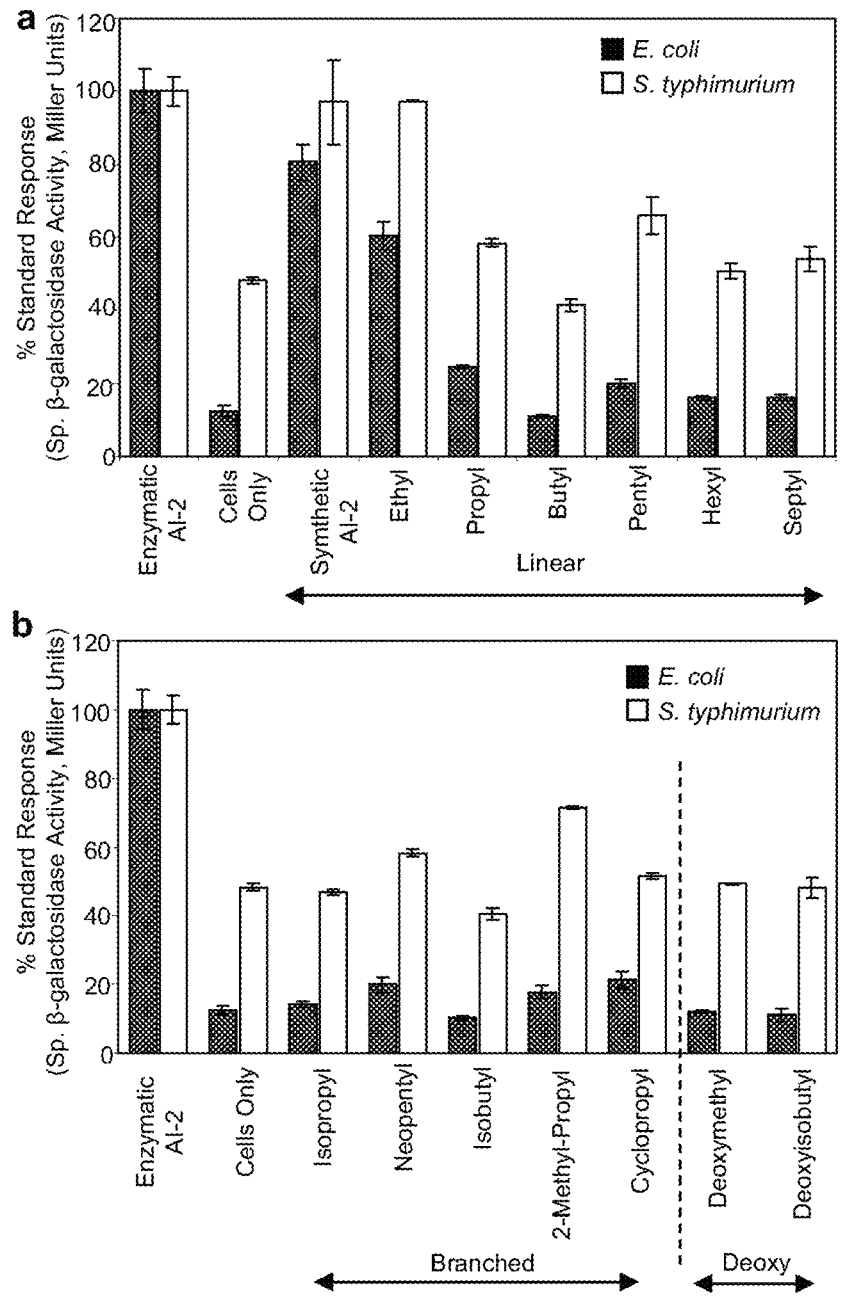
FIG. 9. Identification of analogues as agonists or antagonists in E. coli and S. typhimurium AI-2 dependent β-galactosidase production in E. coli LW7 pLW11 and S. typhimurium MET715 (both luxS− and no AI-2 added) in response to only the (a) linear analogues (b) branched and deoxy analogues respectively.

Data in this Example suggest that the phosphorylation of DPD analogs (FIG. 7) is the first essential checkpoint for lsr transcription repression; isobutyl-DPD is a potent quorum quencher while its unphosphorylated counterpart deoxy-isobutyl-DPD is unable to quench lsr transcription. However, phosphorylation is not the only criterion for antagonism, as some analogs such as cyclopropyl-DPD which is phosphorylated by LsrK are still not able to repress lsr expression. The second checkpoint is binding to LsrR (FIG. 7) to form a stable LsrR-lsr DNA complex, and thus preventing derepression of the lsr operon by phospho-AI-2 binding. Non-covalent interactions (most probably, van der Waals in nature) engages the alkyl chains of DPD analogs with certain residues in the active site of LsrR and locks the protein into a conformation that has a higher affinity for the DNA binding sequence. The observation that a minimum of $C_3$ alkyl chain length is required for DPD-analog antagonism, lends credence to the role that a probable hydrophobic pocket in LsrR plays in the distribution of the various LsrR conformations. Data presented in this Example demonstrates several important findings pertinent to AI-2-based QS in both *S. typhimurium* and *E. coli*. Depending on the nature of the C1-alkyl chain, phosphorylated AI-2-like molecules can either stabilize or destabilize LsrR-DNA complex. Therefore, small molecules that possess phosphate-like moieties as well as C1-alkyl chains of appropriate length and shape are expected to be useful QS modulators in bacteria that utilize LsrR-like transcriptional factors to regulate QS circuits. Secondly, subtle differences in AI-2 processing enzymes in different bacteria allow for selective modulation of QS processes in an ecosystem. On the other hand, it is also possible to effectively modulate QS processing in a variety of bacteria that have different QS receptors or processing enzymes using a single small molecule.

The following materials and methods were used to obtain the data described in this Example.

Synthesis of Diazodiols: To a solution of the diazocarbonyl in anhydrous acetonitrile (0.2M) was added DBU (0.16-0.20 eq) and the requisite aldehyde (2-(tert-butyldimethylsilyloxy)acetaldehyde or acetaldehyde) (1-1.5 eq). The reaction was stirred at room temperature under nitrogen for 4-8 hours and monitored by TLC. Upon disappearance of starting material, the reaction was quenched with sodium bicarbonate. The organic layer was extracted with dichloromethane (3×20 mL) and dried with magnesium sulfate. The solvent was evaporated under reduced pressure. To a solution of crude product in anhydrous tetrahydrofuran (0.2M) TBAF was added (1-2 eq) at 0° C. The solution was allowed to warm to room temperature and stirred for 1-3 hours under nitrogen. The solvent was evaporated and the crude product was purified by column chromatography. The product eluted as yellow oil with 1:3 to 3:2 ethyl acetate:hexane.

Synthesis of DPDs: To a solution of diazodiol (1 eq) in acetone (1-2 mL) was added dioxirane (15-20 mL) in acetone dropwise. The reaction was allowed to stir at room temperature (1-2 hrs) until complete disappearance of starting material as indicated by TLC (loss of UV activity). Solvent and excess reagent was evaporated under reduced pressure. NMR was taken without further purification.

Synthesis of Quinoxaline Derivatives: To a solution of DPD-analog was added 1,2-phenylenediamine (1.5 eq). The reaction was stirred at room temperature for 10 minutes and then the reaction mixture was washed with 2M HCl. The crude mixture was purified on silica.

Bacterial Strains and Growth Conditions (Table 2) lists the bacterial strains and plasmids used in this study. $S.$ $typhimurium$ and $E.$ $coli$ strains were cultured in Luria-Bertani medium (LB, Sigma) at either 30° C. or 37° C. with vigorous shaking (250 rpm) unless otherwise noted. The $V.$ $harveyi$ strains were grown in LM medium. Antibiotics were used for the following strains: 60 or 100 μg ml$^{-1}$ kanamycin for $S.$ $typhimurium$ MET715, 50 μg ml$^{1}$ ampicillin for $E.$ $coli$ BL21 luxS$^{-}$, 60 or 100 μg ml$^{-1}$ ampicillin for $E.$ $coli$ LW7 pLW11. 50 μg ml$^{-1}$ ampicillin and 50 μg ml$^{-1}$ kanamycin for $E.$ $coli$ MDAI-2 pCT6 and $E.$ $coli$ SH3 pLW11 along with 20 μg/ml chloramphenico for the latter and 20 μg ml$^{-1}$ kanamycin for $V.$ $harveyi$ BB170.

TABLE 2

List of bacterial strains, plasmids and primers used in this study

| Strain, plasmid or primer | Relevant genotype and/or property |
|---|---|
| *Escherichia coli* strains | |
| W3110 | Wild type |
| BL21 luxS$^{-}$ | F' ompT hsdS$_B$ (r$_B^-$m$_B^-$) gal dcm ΔluxS :: Kan |
| LW7 | W3110 ΔlacU160-tna2 ΔluxS :: Kan |
| ZK126 | W3110 ΔlacU169-tna2 |

TABLE 2-continued

List of bacterial strains, plasmids and primers used in this study

| Strain, plasmid or primer | Relevant genotype and/or property |
|---|---|
| LW9 | ZK126 Δ(lsrACDBFG)::Kan |
| SH3 | W3110 ΔlacU160-tna2 ΔluxS ΔlsrK :: Kan; Cm |
| *Salmonella typhimurium* strains | |
| MET715 | rpsl putRA :: Kan-lsr-lacZYA luxS :: T-POP |
| MET708 | rpsl putRA :: Kan-lsr-lacZYA |
| *V. harveyi* strains | |
| BB170 | BB120 luxN :: Tn5 (sensor 1$^-$, sensor 2$^+$); AI-1$^+$, AI-2$^+$ |
| Plasmids | |
| pLsrK | pET200 derivative, *Escherichia coli* W3110 LsrK$^+$ |
| pLW11 | galK'-lacZYA transcriptional fusion vector, containing lsrACDBFG promoter region, Amp$^r$ |
| pCT6 | pFZY1 derivative, containing lsrR and lsrR promoter region fused with T7RPol, Ap$^r$ |
| pET-GFP | pET200 derivative, containing gfpuv, Km$^r$ |

In Vitro Phosphorylation of Analogs

LsrK was purified and from $E.$ $coli$ BL21 pET200-LsrK as described before. Phosphorylated analogs were synthesized by incubating 1 μM LsrK with 40 μM ATP (Roche), 0.2 Ci of [γ-$^{32}$P] ATP (Perkin-Elmer), 300 μM AI-2, 200 μM MgCl$_2$, in 25 mM phosphate buffer, pH 7.4 for 2 hours. A 5 μL aliquot was then spotted onto a cellulose TLC plate (Selecto Scientific). The plate was developed using 0.8 M LiCl as the solvent, air dried and developed via autoradiography.

Measurement of the QS Response (lsr Expression)

The QS response indicated by lsr gene expression was analyzed in pure culture studies by culturing $E.$ $coli$ LW7 pLW11, $E.$ $coli$ ZK126 pLW11 and $S.$ $typhimurium$ MET708, $S.$ $typhimurium$ MET715 overnight in LB medium supplemented with appropriate antibiotics as stated previously. These cells were then diluted into fresh LB medium (with antibiotics) and grown to an OD$_{600}$ of 0.8-1.0 at 30° C., 250 rpm. Cells were then collected by centrifugation at 10,000×g for 10 minutes, and resuspended in 10 mM phosphate buffer. AI-2 (20 μM) and the respective analog (20 μM) were added to the $E.$ $coli$ or $S.$ $typhimurium$ suspension for 2 hours at 37° C. AI-2 dependent β-galactosidase production was quantified by the Miller assay.

Measurement of the QS Response (Bioluminescence)

The effect of isobutyl-DPD or isopropyl-DPD on QS associated bioluminescence production by $V.$ $harveyi$ was recorded by measuring the light production from reporter strain, $V.$ $harveyi$ BB170. The analogs were added at concentrations of (20 μM or 40 μM) to $V.$ $harveyi$ BB170 which was assayed as previously described.

Analyzing QS Response in the Synthetic Ecosystem

The $S.$ $typhimurium$ MET708, $V.$ $harveyi$ BB170 and $E.$ $coli$ W3110 pCT6 were each cultured separately overnight in LM medium supplemented with the appropriate antibiotic. $V.$ $harveyi$ BB170, $S.$ $typhimurium$ MET708 and $E.$ $coli$ MDAI-2 were diluted (1:4:8), respectively, into a single 1 ml volume of fresh LM medium without antibiotics. The co-culture was supplemented with either 20 μM or 40 μM analog initially and again after 3 and 5 hours of growth. The $V.$ $harveyi$ luminescence response was measured after 2.5 hours. The $S.$ $typhimurium$ lacZ (β-galactosidase) activity was measured after 4 hours. The $E.$ $coli$ response was determined after 8 hours, by fixing the cells with 1:1 cold 4% paraformaldehyde and using flow cytometric analysis. Samples were analyzed by flow cytometry (FACS Canto II, BD 394 Biosciences), with 20,000 gated events analyzed per sample.

EXAMPLE 2

This Example provides a description of certain compounds of the invention and methods for making and using them.

Synthesis of Phospho-Mimic of AI-2

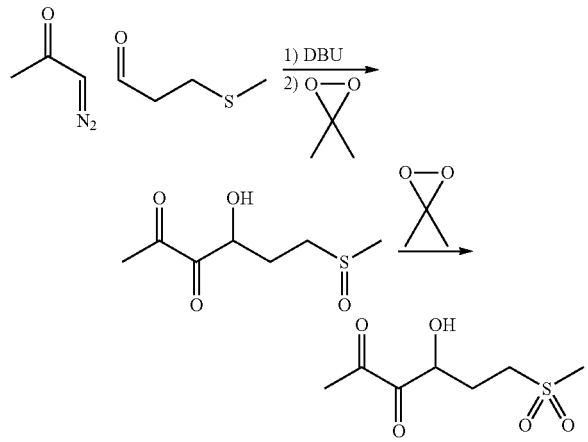

Characterization

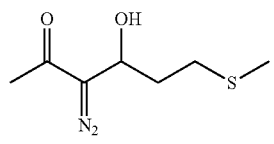

3-Diazo-4-hydroxy-6-methanesulfanyl-hexan-2-one: $^1$H NMR (400 MHz, CDCl$_3$) δ 4.95-4.92 (m, 1H), 2.68-2.66 (m, 2H), 2.28 (s, 2H), 2.14 (s, 1H), 1.99-1.86 (m, 2H). $^{13}$C NMR (100 MHz, CDCl$_3$) δ 15.9, 26.2, 30.6, 33.5, 65.4, 191.9. IR (cm$^{-1}$, CHCl$_3$): 3387.9, 2918.3, 2084.5, 1715, 1614.50.

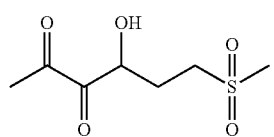

4-hydroxy-6-(methylsulfonyl)hexane-2,3-dione: $^1$H NMR (400 MHz, MeOD) δ 3.22, 2.56, 2.07, 1.95, 1.50. $^{13}$C NMR (100 MHz, MeOD) δ 207.9, 72.1, 51.4, 50.2, 39.9, 23.9. IR (cm$^{-1}$, MeOD): 3387.9, 2918.3, 1715, 1614.50

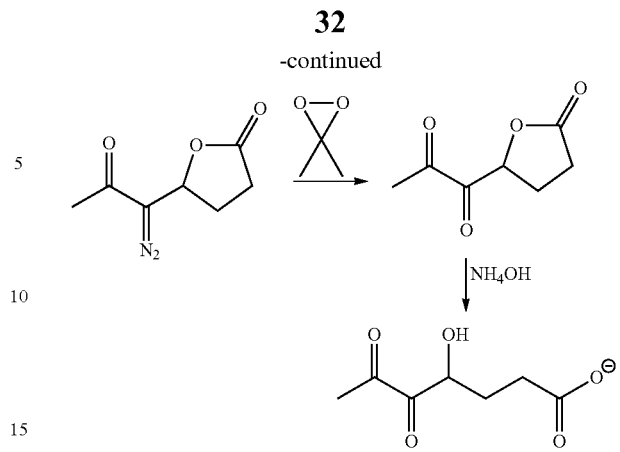

5-(1-Diazo-2-oxo-propyl)-dihydro-furan-2-one: $^1$H NMR (400 MHz, CDCl$_3$, δ): δ 5.59-5.50 (m, 1H), 2.80-2.54 (m, 2H), 2.31 (s, 3H), 2.25-2.06 (m, 2H). $^{13}$C NMR (100 MHz, CDCl$_3$) δ 26.3, 26.7, 29.3, 74.1, 177.0. IR (cm$^{-1}$, CHCl$_3$): 3000-2900, 2090.7, 1771.8, 1642.7.

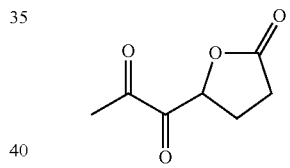

1-(5-oxotetrahydrofuran-2-yl)propane-1,2-dione: $^1$H NMR (400 MHz, MeOD) δ 2.76, 2.51-2.49, 2.25-2.09, 1.65-1.47. $^{13}$C NMR (100 MHz, MeOD) δ 206.1, 178.7, 99.7, 81.9, 80.8, 27.5, 26.2, 23.7, 21.9, 21.1. IR (cm$^{-1}$, CHCl$_3$): 3000-2900, 1771.8, 1642.7.

Synthesis of Amide Analogs of AI-2 and Phosphomimics

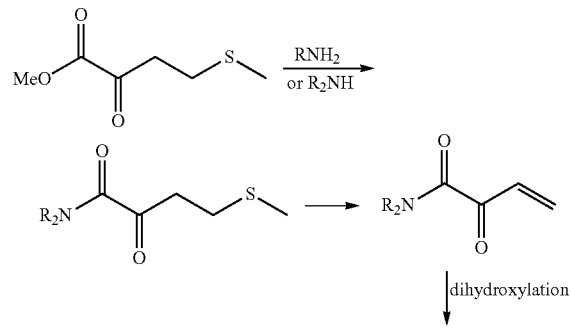

-continued

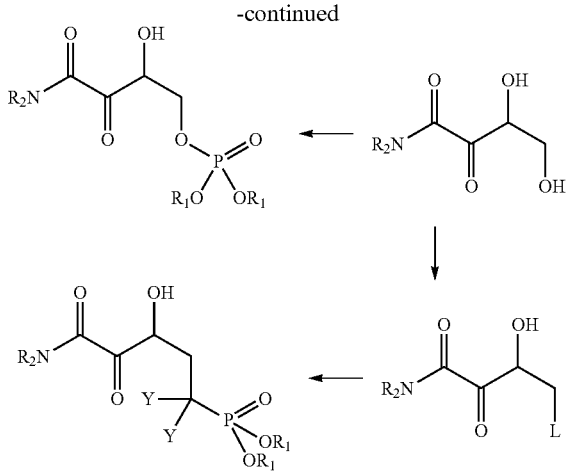

L = leaving group
Y = H or F
R₁ = H or prodrug group

EXAMPLE 3

Figure 19:
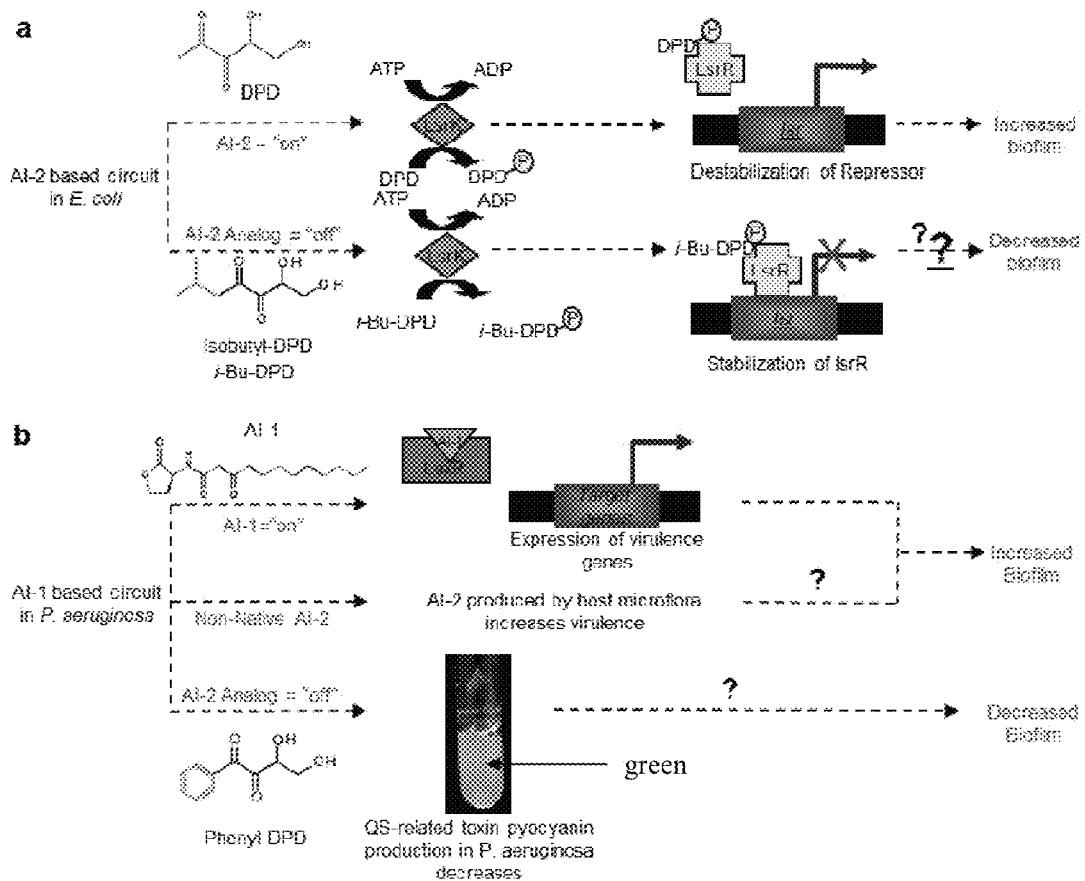
FIG. 19. (a) The AI-2 based circuit in *E. coli*. AI-2 (DPD) is phosphorylated by the *E. coli* kinase LsrK. Phospho-DPD binds to the repressor LsrR derepressing the lsr operon and switching on the expression of related QS genes. Addition of in vitro synthesized AI-2 is known to increase biofilm formation in *E. coli*. It has been shown that the AI-2 analog Isobutyl-DPD is phosphorylated and prevents lsr expression through working with LsrR. Isobutyl-DPD can decrease *E. coli* biofilm formation on its own and in conjunction with antibiotics. (b) The QS mechanism in *P. aeruginosa* is an AI-1 based circuit where AI-1 acts through a LuxI/R homologue circuit and switches on target genes such as biofilm formation. Although *P. aeruginosa* does not synthesize any AI-2 of its own, AI-2 produced by other organisms is known to increase *P. aeruginosa* virulence (Duan et al, 2003). C2 alkyl analogs of AI-2 can decrease pyocyanin (a green-colored toxin) production in *P. aeruginosa*. Phenyl-DPD had a similar effect in decreasing toxin production. Phenyl-DPD can reduce biofilm formation in *P. aeruginosa* on its own and in conjunction with antibiotics.

As shown in FIG. 19, isobutyl-DPD is phosphorylated by LsrK and inhibits QS-related lsr expression. It is thought that unlike AI-2, which is phosphorylated and switches lsr expression "on" by removing the repressor of the circuit LsrR, isobutyl-DPD switches lsr expression "off" by maintaining the LsrR repressor/DNA complex. Additionally, phenyl-DPD inhibits QS related pyocyanin production in *P. aeruginosa*. While this species employs AI-1 for communication and does not synthesize AI-2, gene expression in *P. aeruginosa* can still be regulated by extracellular AI-2 that is produced by surrounding microflora (FIG. 19b). In this invention, AI-2 analogs isobutyl-DPD and phenyl-DPD were used to test whether these "quorum quenchers" alter biofilm formation and maturation among *E. coli* and *P. aeruginosa* respectively.

Figure 20:
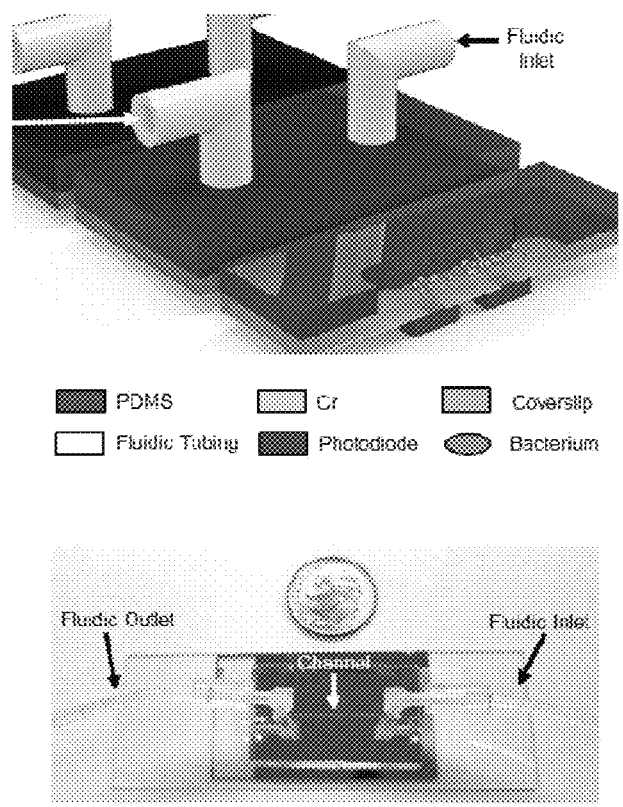
FIG. 20. Schematic and picture of the microfluidic flow cell in which biofilms were formed. The syringe pump was operated in withdrawal mode, providing flow of bacteria, growth media, or fluorescent dye from a reservoir through the channel. Note: the device photographed uses a coverslip with a chrome coating to aid in visualizing the microfluidic channel in the transparent PDMS.

To facilitate these studies, a new microfluidic setting that is useful for rapid real time analysis of biofilm formation, maturation, and removal was created. That is, most biofilm studies are performed in large flow cells with reactor volumes on the order of milliliters. In order to minimize quantities of small molecule effectors (phenyl-DPD & isobutyl-DPD) and perform these experiments in a high-throughput manner, biofilm studies in custom-fabricated microfluidic flow cells with a volume of ~1 μL were conducted (FIG. 20). The device enables minimal reactant volumes, high throughput, and tight control over the microenvironment for cell culture. Streamlined fabrication methods also make this system compatible with integrated sensing techniques, such as electrochemical, mechanical, and optical sensing. Such integrated platforms, or "Lab-on-a-Chip" devices, are capable of sample analysis without reliance on external sample preparation or metrology. Microfluidic devices are ideally suited for efficient bacterial biofilm formation, culture, and monitoring as they can be run in parallel with internal standards. Real time optical sensing is integrated within the microfluidic biofilm detection channel, showing the gradual appearance and clearance of the biofilms continuously over time in response to various treatments. In this way, experiments are not restricted to single end point measurements. In addition to observing the effects of isobutyl-DPD and phenyl-DPD on *E. coli* and *P. aeruginosa* biofilm growth, clearance of pre-formed biofilms was observed. Because of enhanced flexibility enabled by the microdevices, AI-2 analogs and the antibiotic gentamicin could be used to clear biofilms in a synergistic fashion was investigated.

The following materials and methods were used to obtain the data presented in this Example.

Microfluidic Device Fabrication and Assembly

Fabrication of the microfluidic device (FIG. 20) was described in. The device base is a coverslip, which provides a transparent substrate thin enough for high resolution confocal microscopy. In experiments where optical density was continuously measured, coverslips were patterned with two pinholes to allow alignment of windows with embedded optics. In confocal microscopy experiments, 7 fields in each channel were imaged; the coverslips were uncoated and unpatterned as optical density measurements were not performed.

The microfluidic channel itself consists of polydimethylsiloxane (PDMS) molded by photopatterned SU8-50. Here, the mold produces microfluidic channels 100 μm deep, 500 μm wide, and 2 cm long. Ports for interfacing the channel to fluidic tubing are drilled into the PDMS using a dermatological punch. The PDMS is reversibly adhered to the coverslip by soaking the bonded side of the PDMS in methanol for 1 min, then aligning and placing the section of PDMS over the coverslip.

The microfluidic channel is interfaced to external fluidic components using flexible Tygon tubing and barbed tube fittings. At the fluidic outlet, one end of the tubing is connected to a syringe pump operating in withdrawal mode, and at the inlet, the other end is inserted into a sealed microcentrifuge tube (1.5 mL) serving as a reservoir for growth medium or other liquids that are flowed into the channel. Each microfluidic device is pre-sterilized using 70% ethanol. The entire apparatus is positioned in an incubator held at 37° C.

Biofilm Formation

The *E. coli* biofilms were formed using the strain K-12 MG1655 ATCC(47076). *P. aeruginosa* biofilms were formed using wild type strain PAO1. For both strains, overnight cultures were diluted to an $OD_{600}$ of 0.25, introduced into the microfluidic channel, and incubated with no flow at 37° C. for 2 h. LB (Luria Bertani) growth medium was then continuously flowed into the device at a rate of 10 μL/hr. As needed, this medium was supplemented with various concentrations of analog or antibiotic at specified times. In studies of biofilm inhibition, after 2 hours of cell incubation, the analog diluted in LB medium is flown into the microfluidic channel for 48 hours at 10 μL/hr. In studies of effects on pre-formed biofilms, LB is introduced over the cells at 10 μL/hr for a period of 36 to 48 hours to yield stable biofilms. Then, the analog or analog-antibiotic combination was introduced for an additional 36 to 48 hours.

Biofilm Staining and Confocal Microscopy

Biofilms were stained in situ for microscopy. They were first treated with a Live/Dead bacterial labeling kit (Invitrogen #L7012) in which two labeling components were mixed in a 1:1 ratio to a final volume of 10 μL. The dye was introduced into the channel at 10 μL/hr, the same flow rate as during biofilm growth. This treatment was then followed by 10 μL/hr of a 100 μg/mL calcofluor (Fluorescence Brightener 28, Sigma #F3543) solution for labeling polysaccharides contained in the biofilm matrix. The dyes are fixed by flowing in 3% paraformaldehyde at the same flow rate.

Labeled samples are imaged using a confocal microscope (Zeiss LSM710). For unpatterned coverslips, Z-stacks were obtained at 7 points in each microfluidic channel, each stack was comprised of 150 slices. For patterned coverslips used while measuring the optical density of the biofilms, two stacks were obtained in each channel (i.e. one at each pinhole). The image stacks were analyzed using COMSTAT, which provides morphological characteristics. Average biofilm thickness and biomass were averaged over the image stacks obtained at each of these 7 data points in the microfluidic channel. Additionally, surface reconstructions of the biofilms were created using Imaris (Bitplane) to aid in visualization of the resulting structures. Images displayed were selected from locations where the thickness and biomass were closest to the average of all measurements.

The following results were obtained using the foregoing materials and methods described in this Example.

Biofilm Maturation in the Presence of AI-2 Analog

Figure 21:
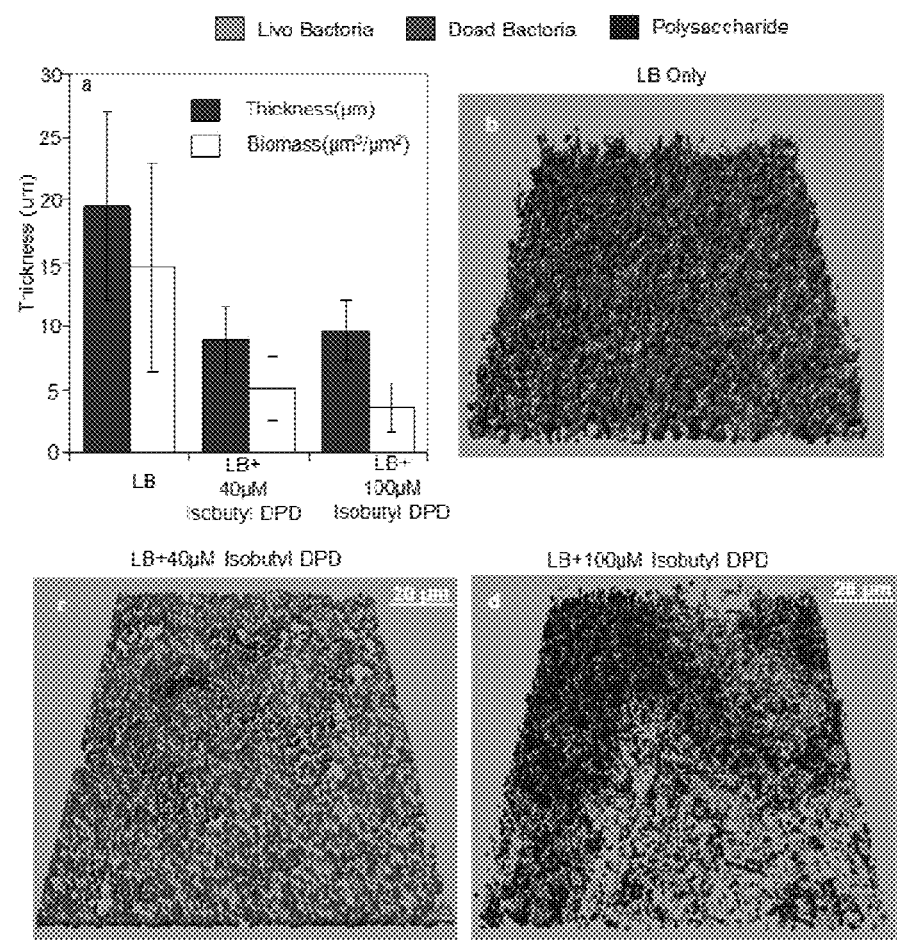
FIG. 21. Analysis of *E. coli* biofilm thickness and architecture in response to Isobutyl (a) Thickness and biomass of biofilm analyzed by COMSTAT (Average of 4 different points). (b-d) Representative Imaris 3-D surface reconstructions of the biofilm with (b) LB Only (c) LB+40 μM Isobutyl DPD (d) LB+100 μM Isobutyl DPD. Images were selected from locations with average thicknesses and biomasses closest to the average of all points analyzed.

The effect of the analog on biofilm growth was tested by continuously exposing the cells to analog diluted in LB. In (FIG. 21a), perfusion of LB media enabled biofilm growth to an average thickness of 22 µm and an average biomass of 14 $\mu m^3/\mu m^2$ by the end of the incubation period (48 h). The presence of 40 µM isobutyl-DPD inhibited the biofilm growth by ~70%, yielding films 7 µm thick with biomass of 3.5 $\mu m^3/\mu m^2$. Increased analog concentration to 100 µM had no further inhibitory effect on biofilm thickness. Surface rendering images of the biofilms confirmed that without isobutyl-DPD, the biofilm was much thicker and more structured (e.g., more void space, microchanneling, larger groupings of live and dead cells (FIG. 21b). The presence of analog (both 40 and 100 µM) yielded biofilms more like thin bacterial carpets (FIG. 21c-d). A striking difference however, was found between the isobutyl-DPD treated cultures. The biofilm with 100 µM isobutyl-DPD appeared more sparse and with less surface coverage than that exposed to 40 µM isobutyl-DPD. Moreover, nonviable cells were virtually gone and a preponderance of polysaccharide was found. These results are believed to be the first demonstration that an AI-2 analog, isobutyl-DPD, can decrease biofilm formation in E. coli.

Effects of Analog on Pre-formed E. coli and P. aeruginosa Biofilms

As isobutyl-DPD is an established QS quencher, it is neither bacteriostatic nor bacteriocidal among planktonic cells. Thus, if isobutyl-DPD were used to treat the bacteria and the pathogenic bacterial populations were not removed from the host, an infection would persist. While live biofilms seemed to persist, owing to their apparent thinner and more porous structure it was hypothesized that antibiotic co-administration could be more effective in their eventual eradication.

Figure 22:
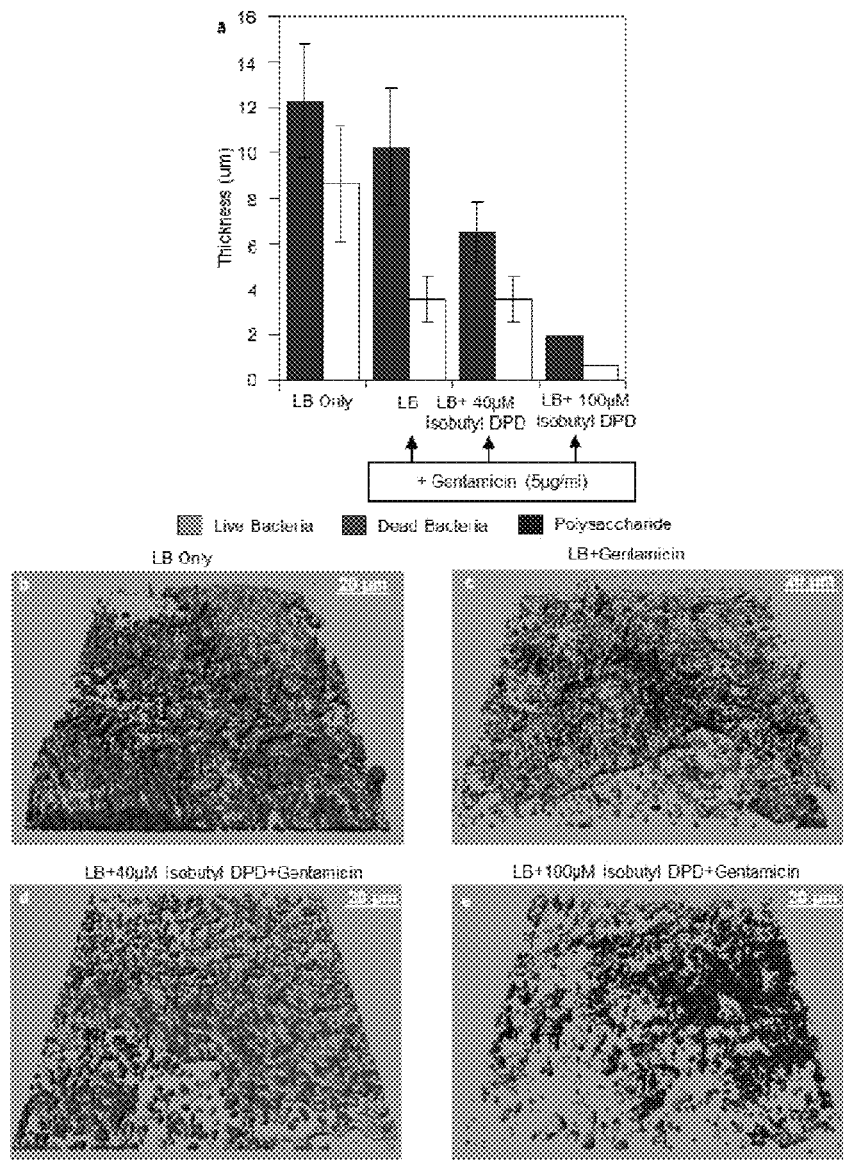
FIG. 22. Analysis of effect of combinatorial approach analog and gentamicin on preformed *E. coli* biofilm thickness and architecture (a) Thickness and biomass of biofilm analyzed by COMSTAT (Average of 5 different points in the channel). (b-e) Representative Imaris 3-D surface reconstructions of the biofilm with (b) LB Only (c) LB+5 μg/ml Gentamicin (d) LB+40 μM Isobutyl+5 μg/ml Gentamicin (e) LB+100 μM Isobutyl DPD+5 μg/ml Gentamicin. Images were selected from locations with average thicknesses and biomasses closest to the average of all points analyzed.

In order to test this approach, combinations of gentamicin (5 µg/ml) with increasing concentrations of isobutyl-DPD (40 µM and 100 µM) were used to treat pre-established E. coli biofilms. The control biofilm, exposed to LB medium only, exhibited an average thickness of 12 µm and an average biomass of 8.5 $\mu m^3/\mu m^2$ (FIG. 22a). Addition of gentamicin without AI-2 analog decreased the thickness slightly to 10 µm, yet the biomass dropped by ~50% (3.5 $\mu m^3/\mu m^2$). However, addition of a cocktail of antibiotic and analog (40 µM isobutyl-DPD) decreased the average biofilm thickness to 6 µm (FIG. 22a). Most importantly, this study showed that 100 µM isobutyl-DPD used with gentamicin was the most effective in clearing the pre-formed biofilm, shown by the reduction in thickness by more than 80% to an average of 2 µm and by the nearly complete removal of biomass. The 3-D surface rendering images confirmed morphological data (FIG. 22b-e), as the biofilm surface thickness decreased significantly in the presence of both isobutyl-DPD and gentamicin. With 100 µM of analog and 5 µg/ml gentamicin, the biofilm was extremely sparse.

Mechanistic bases for these C1-alkyl analogs in E. coli was suggested but there was no concrete inferences of mechanisms for attenuated QS communication among otherwise AI-1 communicating P. aeruginosa. A recently expanded set of C1-acyl analogs of DPD revealed QS quenching activity among P. aeruginosa for a few cyclic compounds, phenyl-DPD in particular. Here, the combination of phenyl-DPD (100 µM) and gentamicin (5 µg/ml) on pre-existing P. aeruginosa biofilms was tested. When treated with a combination of phenyl-DPD and gentamicin, P. aeruginosa biofilms became far more thin and more sparse than untreated controls (thickness, 2 µm vs. 26 µm; biomass, <2 $\mu m^3/\mu m^2$ vs. 15 $\mu m^3/\mu m^2$, FIG. 23a). These results were corroborated by the qualitative evaluation of the images obtained through surface rendering of confocal microscopy results (FIG. 23b-e). Biofilms grown without the addition of phenyl-DPD show denser surface coverage and appeared more structured than biofilms grown with phenyl-DPD. The P. aeruginosa biofilms treated with both phenyl-DPD and gentamicin, similar to E. coli results, were much more sparse than controls with LB.

Leveraging Microscale Biofilm Reactor for Streamlined Measurement

While confocal microscopy is extremely effective for characterizing bacterial biofilms, especially in conjunction with analysis software such as COMSTAT and Imaris, implementing this method requires extensive sample preparation and imaging time; the staining and imaging performed in this study required up to 12 hours of time added to the experiment itself. In addition to the benefits provided by the microliter-size channel volume, microfluidic biofilm reactors also possess the ability to integrate precise biofilm measurements with the fluidic operation of the device. In this work, the microfluidic reactor was integrated with continuous optical density measurement to dynamically evaluate the synergistic influence of AI-2 analog and antibiotic on pre-formed biofilms.

Figure 18:
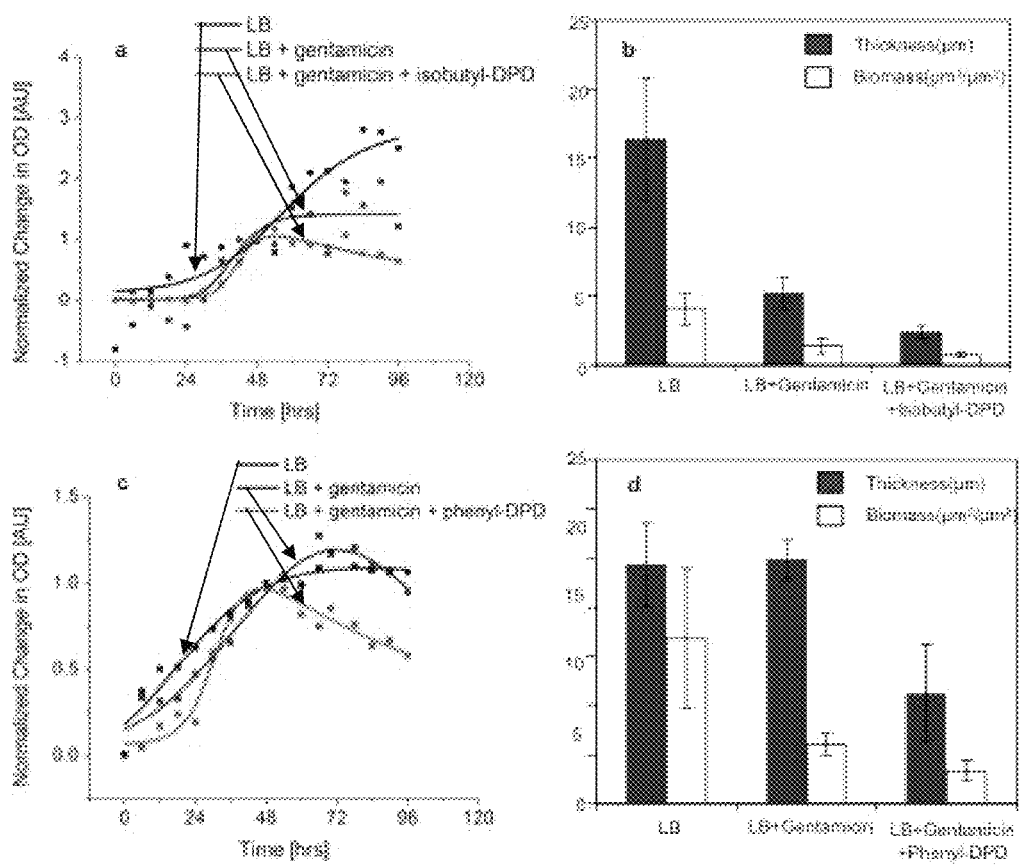
FIG. 18. Analysis of effect of combinatorial approach on optical density and thickness using analog and gentamicin on *E. coli* (a-b) and *P. aeruginosa* (c-d) biofilms preformed for 48 hours. (a) Normalized change in optical density of *E. coli* biofilms; raw data (dotted lines) were normalized with the change in OD at 48 hrs set to be 1. Curves were fitted (solid lines) using a Churchill model. (b) Thickness and biomass of *E. coli* biofilm analyzed by COMSTAT (Average of the 2 points in the channel). (c) Normalized change in optical density of *P. aeruginosa* biofilms; raw data (dotted lines) were normalized and fitted (solid lines) using a Churchill model. (d) Thickness and biomass of *P. aeruginosa* biofilm analyzed by COMSTAT (Average of the 2 points in the channel).

Dynamic analysis of replicate windows reveals a complex non-uniform process that when fitted to a mathematical model suggest relatively uniform biofilm growth overall for the first 48 h, at which time, divergent behaviors were observed based on small molecule addition (FIG. 18). That is, the addition of gentamicin slowed the progress of biofilm maturation relative to the controls and the combined effects of gentamicin with isobutyl- or phenyl-DPD then reversed biofilm growth, resulting in diminished films by the end of the experiments. Thus, the scenario is quite different dynamically than the natural inference following experiments depicted in (FIG. 23), where one would conclude a monotonic decrease in film thickness and density upon the combined additions of phenyl-DPD and gentamicin.

Figure 23:
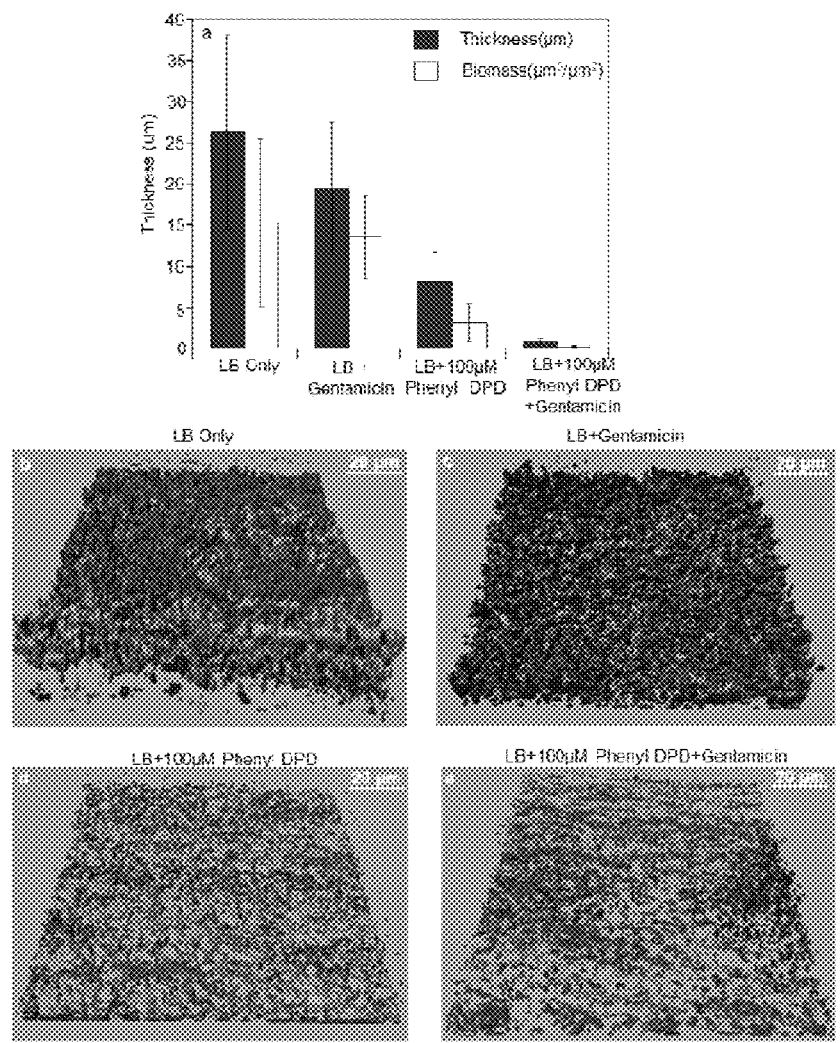
FIG. 23. Analysis of effect of combinatorial approach analog and gentamicin on preformed *P. aeruginosa* biofilm thickness and architecture (a) Thickness and biomass of biofilm analyzed by COMSTAT (Average of 5 different points in the channel). (b-e) Representative Imaris 3-D surface reconstructions of the biofilm with (b) LB Only (c) LB+5 μg/ml Gentamicin (d) LB+100 μM Phenyl (e) LB+100 μM Phenyl+5 g/ml Gentamicin. Images were selected from locations with average thicknesses and biomasses closest to the average of all points analyzed FIG. 24. Structure of AI-2 dimer.
Figure 24:
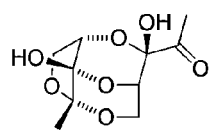

The following description refers to FIG. 23, from which it can be seen that there is no statistical difference between biofilms formed by P. aeruginosa that are treated with Gentamicin and control group (no gentamicin added). Therefore gentamicin alone caused ~0% biofilm reduction. When 100 uM phenyl DPD was added to P. aeruginosa biofilm reduction is about 40%. Interestingly, when gentamicin and 100 uM phenyl DPD were combined, biofilm reduction was close to 100% (a clear example of synergistic effect).

Compositions of the invention, and especially DPD analogs, can be used in combination with antibiotics that are members of classes such as aminoglycosides, beta lactams (with or without beta lactamase inhibitor such as clavulanic acid), macrolides, glycopeptides, polypeptides, cephalosporins, lincosamides, ketolides, rifampicin, polyketide, carbapenem, pleuromutilin, quinolones, streptogranin, oxazolidinones, lipopeptides.

Those skilled in the art will recognize that it is an understatement to state that bacterial biofilms are recalcitrant to antibiotic treatment. There are various hypotheses for mechanisms for antibiotic resistance within biofilms. First, the antibiotic is unable to penetrate through thick biofilm layers. Second, the altered chemical environment inside the biofilm, for example the accumulation of acidic waste products, can inactivate the antibiotic. Also, the differences in nutrient gradient concentrations and anaerobic niches in the biofilms can lead to cells entering a dormant state in which they are neither dead or alive, somewhat similar to spores. These cells, known as persister cells, are highly resistant to antibacterial agents. QS inhibitors, while not bactericidal, can mitigate biofilm formation by inhibiting bacterial communication, thereby restricting expression of genes related to biofilm formation. This suggests that the bacteria within a nascent biofilm might phenotypically be more "similar" to bacteria in suspension. Biofilms used to illustrate embodiments of the present invention, while continuously supplemented with AI-2 analogs showed decreased formation, even without additional antibiotic. While the AI-2 analogs did not directly kill the bacteria, interfering with the QS-regulated mechanisms involved in biofilm formation (e.g. motility, extracellular matrix secretion) appeared to delay or minimize creation of significant biofilm architecture. That is, lacking the structural cohesiveness of an extracellular matrix produced with the aid of native quorum sensing, biofilms treated with large analog concentrations are potentially more susceptible to delamination. As non-viable cells have weaker substrate adhesion than viable cells, they are more likely to delaminate. Results in FIG. 21 at 100 µM isobutyl-DPD where nonviable cells had been removed from the polysaccharide matrix, support this notion. Conversely, the remaining polysaccharide matrix that was not able to retain these cells, maintains adhesion to the substrate.

Then, when AI-2 analog was supplemented with gentamicin, the biofilms eventually subsided, presumably because they were more susceptible to antibiotic exposure. The present invention shows that QS inhibitors are capable of either dispersing/preventing biofilms on their own or potentiating the effects of traditional antibiotics for the clearance of E. coli and P. aeruginosa biofilms.

The potentiation of the antibiotic or anti-biofilm effect of gentamicin by the co-admnistration with AI-2 analogs is significant because it could lead to a scenario whereby biofilms of pathogenic bacteria could be pdispersed with sub-MIC levels of antibiotics, thereby preventing a wanton destruction of the surrounding natural microflora. Secondly, the use of sub-MIC concentrations of antibiotics would retard the emergence of resistant strains. For antibiotics that have a narrow therapeutic window, due to toxicity to the host, a strategy to lower the MIC or synergistically aid the antibiotic to clear biofilms at lower concentrations would be wholly welcomed.

In the present Example, the use of a microfluidic testing environment with integrated optical measurements in a dynamic and controllable environmental setting allowed for evaluating the "instantaneous" state of the biofilm. This contrasts with the sole use of microscopy, which would have only permitted an endpoint measurement. Therefore the use of the microfluidic setup revealed phenotypic data, which would have normally been lost had only used end-point measurements been utilized. This is especially important considering that the formation of a biofilm itself is highly variable; by tracking a single point in the biofilm throughout growth and treatment, the contribution of the analog and antibiotic synergism toward biofilm reduction is clarified.

Optical Density Data Analysis

The data corresponding to the change in optical density of the biofilms were obtained from the photodiodes using the standard methodologies. Data for each channel (the average of the response of the two photodiodes) was normalized with respect to the optical density at 48 hours; this method reflects that as of 48 hours, the biofilms have been grown under identical conditions although their optical density values may not be identical. Additionally, since the optical density data itself fluctuates as the biofilm grows, the data for each curve was fitted using a Churchill model (Churchill et al, 1972), represented by $$\log N = [f_1^{-1} + f_2^{-1}]^{-1} \quad (1)$$

Here, N represents the biomass; in this case, it is assumed to be directly correlated to the optical density. $f_1$ and $f_2$ represent the growth and death of the culture, respectively, and can be expressed in a generalized form as $$f_1 = K_1 \exp(\lambda_1 t) \quad (2)$$

$$f_2 = K_2 \exp(-\lambda_2 t) \quad (3)$$

While this model is intended for application toward batch cultures, it is used here to approximate the similar growth of a biofilm.

EXAMPLE 4

This Example provides yet another description of compounds of the invention, and methods of making and using them.

Synthesis of Diazocarbonyls

Generation of Diazomethane

Diazomethane was generated from Diazald® (Sigma-Aldrich) using a diazomethane generator apparatus (Sigma-Aldrich), following the protocol provided by Sigma-Aldrich. Briefly, a solution of Diazald® (5 g) in diethyl ether (45 mL) was slowly added to a solution of KOH (5 g) in mixed solvent (water (8 mL) and ethanol (10 mL)) at 65° C. over 20 min. The generated diazomethane and the diethyl ether solvent distilled and was trapped in a collecting vessel using a dry ice/isopropanol bath to give diazomethane as a solution in diethyl ether (ca. 0.4-0.5 M).

Addition of Diazomethane to Acyl Chlorides

To a solution of diazomethane (3 equiv.) in diethyl ether was added an acyl chloride (1 equiv.) dropwise at 0° C. The resulting solution was allowed to stir for another 2 h and warmed up gradually to room temperature. The solvent was removed under vacuum and the diazocarbonyl residue (yellow liquid) was used for the next step without further purification.

Synthesis of Diazodiols

DBU (0.16-0.20 equiv.) and 2-(tert-butyldimethylsilyloxy)acetaldehyde (1-1.5 equiv.) were added to a solution of the diazocarbonyl (crude, 1 equiv.) in anhydrous acetonitrile (0.2 M). The reaction was stirred at room temperature under nitrogen for 4-8 h and monitored by TLC. Upon disappearance of starting material, the reaction was quenched with sodium bicarbonate. The organic layer was extracted with dichloromethane (3×20 mL) and dried with magnesium sulfate. The solvent was evaporated under reduced pressure. To a solution of crude product in anhydrous tetrahydrofuran at 0° C., TBAF was added (1-2 equiv.). The solution was allowed to warm to room temperature and stirred for 1-3 h under nitrogen. The solvent was evaporated, and the crude product was purified by column chromatography. The products eluted as yellow oils using 1:3 to 3:2 ethyl acetate/hexane as the mobile phase.

Synthesis of Ester Protected Diazo Compounds

To a stirring solution of diazodiol (1 equiv.) catalytic 4-dimethyl aminopyridine (DMAP) and suspended 4 Å molecular sieves in dichloromethane (DCM) was added the requisite anhydride. The reaction was allowed to gently stir at room temperature for 2-4 h until complete disappearance of starting material was indicated by TLC. The crude reaction mixture was filtered washed with saturated aqueous $NaHCO_3$ solution and the organic phase was extracted with more DCM. The combined organic phases were dried with anhydrous $MgSO_4$ and the solvent was evaporated at reduced pressure. The crude product was purified by column chromatography. The products eluted as yellow oils using 1:3 to 1:2 ethyl acetate/hexane as the mobile phase.

Synthesis of DPDs

Dimethyldioxirane in acetone (15-20 mL) was added dropwise to a solution of ester protected diazodiol (1 equiv.) in acetone (1-2 mL). The reaction was allowed to stir at room temperature (1-2 h) until complete disappearance of starting material was indicated by TLC (loss of UV activity). Solvent and excess reagents were evaporated under reduced pressure.

Bacterial Strains and Growth Conditions

Table 3 lists the bacterial strains used in this study. *S. typhimurium* and *E. coli* strains were cultured in Luria-Bertani medium (LB, Sigma). These antibiotics were used for the following strains: (60 µg $mL^{-1}$) kanamycin for *S. typhimurium* (MET715) and (50 µg $mL^{-1}$) ampicillin for *E. coli* (LW7).

TABLE 3

Bacterial strains used in this Example.

| Strain | Relevant genotype and/or property |
| --- | --- |
| | *Escherichia coli* |
| LW7 | W3110ΔlacU160-tna2 ΔluxS :: Kan (LuxS-deficient: does not produce AI-2) |
| | *Salmonella typhimurium* |
| MET715 | rpsl putRA :: Kan-lsr-lacZYA luxS :: T-POP (LuxS-deficient: does not produce AI-2) |

Measurement of the QS Response (lsr Expression)

The QS response indicated by lsr gene expression was analyzed in pure culture studies by culturing *E. coli* LW7 pLW11 and *S. typhimurium* MET715 overnight at 30° C. in LB medium supplemented with appropriate antibiotics as stated previously. These cells were then diluted into fresh LB medium (with antibiotics) and grown to an $OD_{600}$ of 0.4-0.8 at 37° C., 250 rpm. Cells were then collected by centrifugation at 10,000×g for 10 min and resuspended in 10 mM phosphate buffer. AI-2 (20 µM) and the respective analog (20 µM) were added to the *E. coli* or *S. typhimurium* suspension for 2 h at 37° C. AI-2 dependent β-galactosidase production was quantified by the Miller assay.

Figure 25:
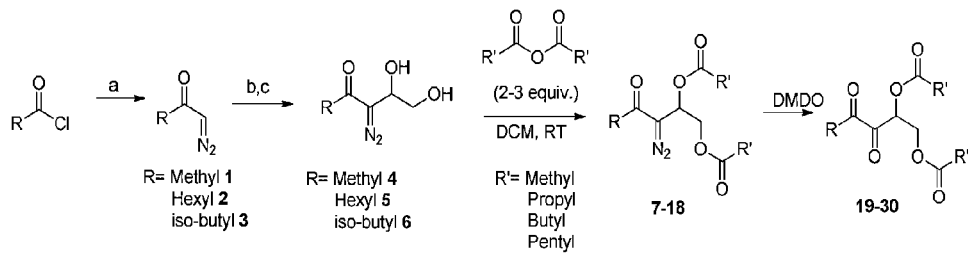
FIG. 25. Reagents and conditions: (a) diazomethane, 0° C., (b) tert-butyl-siloxyacetaldehyde, DBU (1,8 diazabicycloundec-7-ene), $CH_3CN$, RT (c) TBAF/THF. DCM=dichloromethane; DMDO=dimethyldioxirane.

As will be appreciated form the foregoing, the syntheses of bis-ester protected AI-2 and analogs 19-30 were achieved via the strategy shown in FIG. 25. Briefly, an Aldol reaction between diazo carbonyls 1-3 and 2-(tert-butyldimethylsilyloxy)acetaldehyde afforded diazo diols 4-6, after deprotection of the TBS group with TBAF. Oxidation of the diazo group in diazo diols 4-6 afforded AI-2 or analogs but for the production of ester protected AI-2 and analogs, it was important to perform the esterification step first to give bis-ester 7-18 before the oxidation of the diazo bis-ester to give targeted compounds 19-30.

Figure 26:
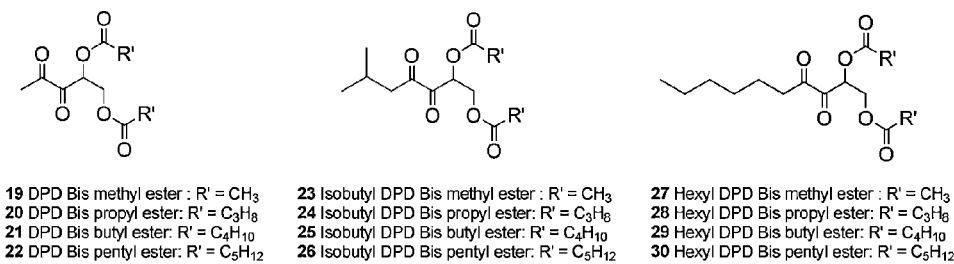
FIG. 26. Compounds evaluated as bis-ester protected AI-2 analogs.

With the various AI-2 or analog ester derivatives (methyl to pentyl esters) in hand (FIG. 26), the biological profiles of these esters was investigated. Previously demonstrated was that AI-2 analogs with longer C1-acyl chains permeate more readily into bacterial cells than shorter chains. This is presumably due to the favorable interactions of the alkyl chain with the phospholipid of the bacterial membrane. We tested whetehr the longer chain ester derivatives (such as butyl or pentyl) would permeate more readily into bacterial cells than the shorter chain analogs, such as the methyl ester series. However, if the cellular esterases were sensitive to the size of the esters, then the longer chain analogs would be hydrolyzed slower than the shorter chain ones. Because biological activity of ester prodrugs is dependent on permeation and prodrug activation and both of these processes would depend on the organism in question, it is not always easy to predict a priori which ester group is most suitable for derivatizing biologically active molecules.

Figure 27:
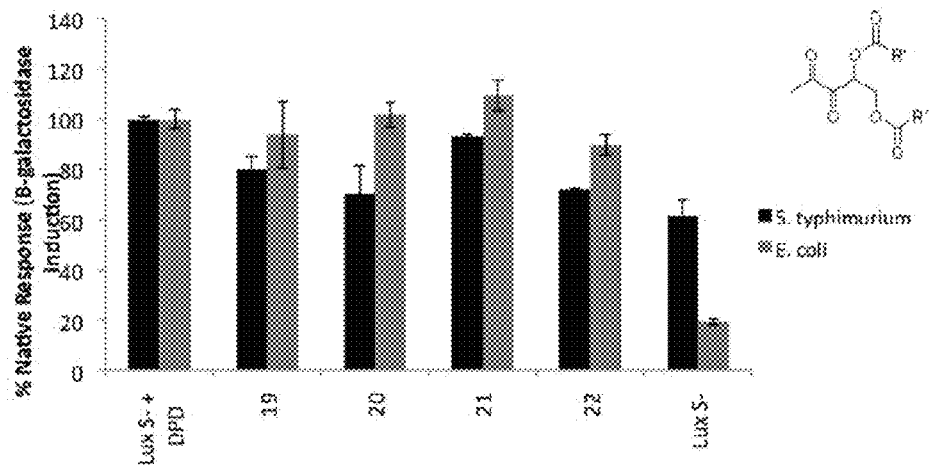
FIG. 27. AI-2 or analogs-mediated expression of β-galactosidase in *S. typhimurium* (MET715: LuxS⁻). AI-2 or analogs-mediated expression of β-galactosidase in *E. coli* LW7/LuxS⁻. AI-2 or bis-ester analogs of AI-2 (20 μM) were added to the bacterial strains, which do not produce their own AI-2. Compounds (19-22) represent ester-protected DPD analogs; 19: DPD bis-methyl ester, 20: DPD bis-propyl ester, 21: DPD bis-butyl ester, 22: DPD bis-pentyl ester.

Bis-ester-protected AI-2 analogs (with different ester chains; methyl, propyl, butyl and pentyl) were all effective lsr expression inducers in *E. coli* (see FIG. 27). For *S. typhimurium*, it appears that LsrR is not as good a repressor (compared to *E. coli*) and significant expression of the lacZ gene was observed even in the absence of added DPD (see control, FIG. 27). Nonetheless, it is apparent that more LacZ protein was present in *S. typhimurium* in the presence of AI-2 than when AI-2 was not present (about 30% more LacZ present when AI-2 is added. See FIG. 27, compare the histograms for "LuxS−+AI-2" and LuxS− (no AI-2 added)). Therefore, even if lacZ expression is not solely controlled by AI-2, one can safely conclude that AI-2 plays some role in lacZ expression in the *S. typhimurium*. Despite high LacZ background in *S. typhimurium*, the majority of the ester protected DPD analogs functioned (although not as effectively as DPD) in inducing lsr expression in *S. typhimurium*; bis-butyl DPD appears to be as effective as DPD (see FIG. 27).

Figure 28:
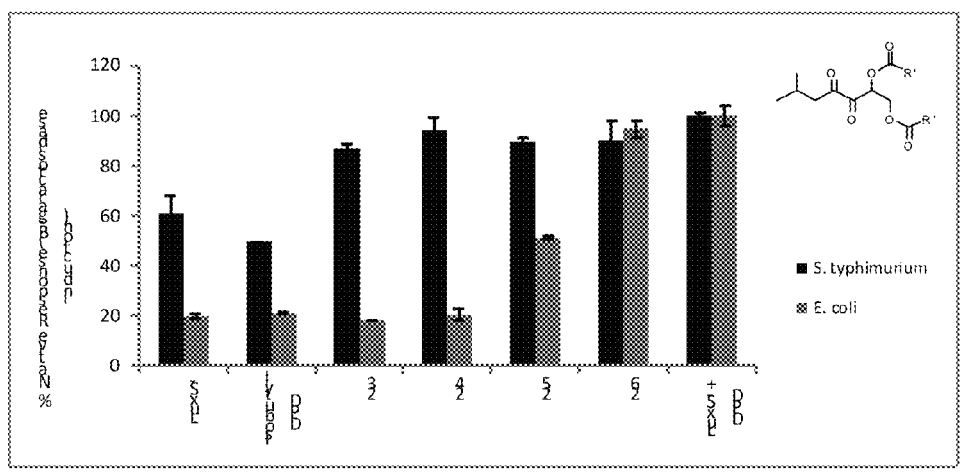
FIG. 28. Inhibition of AI-2-mediated β-galactosidase expression in *S. typhimurium* and *E. coli* with various bis-ester analogs of isobutyl DPD. [AI-2]=20 μM, [analogs]=20 μM. Compounds 23-26 represent ester protected isobutyl DPD analogs; 23: isobutyl DPD bis-methyl ester, 24: isobutyl DPD bis-propyl ester, 25: isobutyl DPD bis-butyl ester, 26: isobutyl DPD bis-pentyl ester.
Figure 29:
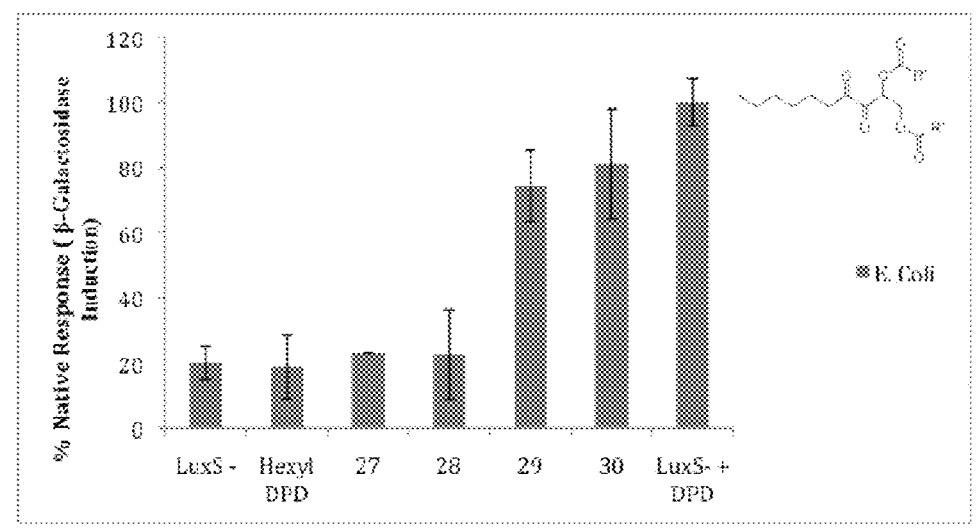
FIG. 29. Inhibition of AI-2-mediated β-galactosidase expression in *E. coli* with various bis-ester analogs of hexyl DPD. [DPD]=20 μM, [analogs]=20 μM. Compounds 27-30 represent ester protected hexyl DPD analogs; 27: hexyl DPD bis-methyl ester, 28: hexyl DPD bis-propyl ester, 29: hexyl DPD bis-butyl ester, 30: hexyl DPD bis-pentyl ester.

The antagonistic profile of the bis-ester analogs of isobutyl DPD in both *E. coli* and *S. typhimurium* was investigated. Isobutyl DPD is an antagonist of AI-2-mediated QS in both *E. coli* and *S. typhimurium* and stable versions of this analog have the potential to disrupt QS processes in these enteric bacteria, which sometimes cause food-borne diseases. For this assay, AI-2 was added to a LuxS-deficient strain of *E. coli* (LW7) or *S. typhimurium* (MET715) to induce lsr expression via the derepression of LrsR by phospho-AI-2. In *E. coli*, bis-methyl and bis-propyl DPD analogs were as effective QS quenchers as the unprotected isobutyl DPD (see FIG. 28). Increasing the length of the ester chain to butyl or pentyl either reduced (butyl) or abrogated (pentyl) the inhibitory profile of the DPD analog. In *E. coli*, the same trend was also observed for the bis-ester derivatives of hexyl DPD (bis-methyl and bis-propyl analogs, but not butyl or pentyl derivatives, were QS inhibitors, FIG. 29). In *S. typhimurium*, however, none of the bis-ester protected isobutyl DPD analogs were able to antagonize the action of AI-2. Addition of isobutyl DPD to *S. typhimurium* however decreased lacZ expression by about 50% (compare black bar corresponding to "isobutyl DPD" to black bar corresponding to "LuxS−+ DPD" in FIG. 28). Thus, *S. typhimurium* and *E. coli* have similar QS systems, but differences in the processing of ester analogs of isobutyl DPD allows for the selective modulation of QS processing in *E. coli* but not in *S. typhimurium*.

Figure 30:
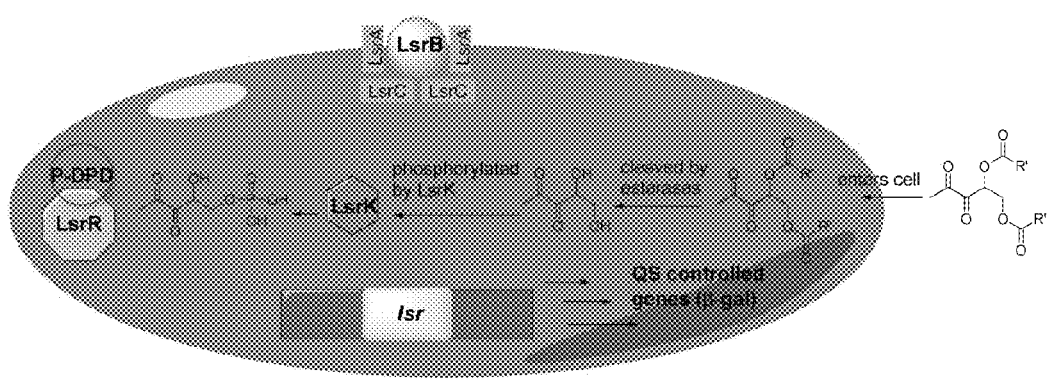
FIG. 30. Proposed model of action in enteric bacteria. Ester protected DPD analogs diffuse into the cell, where esterases hydrolyze the ester pro-DPD and analogs and the DPD or analogs are subsequently phosphorylated by LsrK.

It will be apparent to those skilled in the art from the foregoing description in this Example that derivatives of DPD analogs can be hydrolyzed inside bacterial cells to reveal the biologically active diol unit for quorum sensing disruption. It is possible to achieve selectivity of QS modulation amongst closely related bacteria (between *E. coli* and *S. typhimurium*) via the use of ester protection of the diol unit of AI-2. The origin of this selectivity remains unknown at this moment but it could be a number of several factors, including selective permeation of the analogs or different sensitivities of the esterases required for analog hydrolysis in the different bacteria (FIG. 30).

EXAMPLE 5

This Example provides yet another description of compounds of the invention and methods of making and using them.

Synthesis of Ester Protected Diazodiol

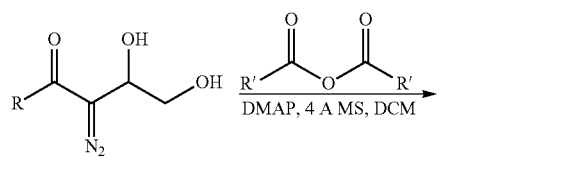

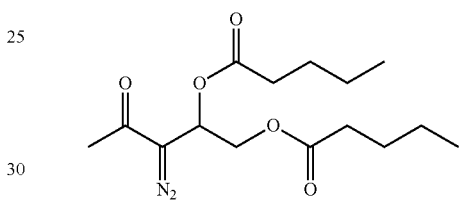

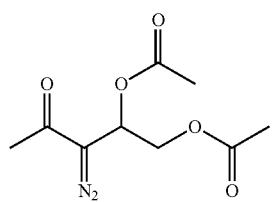

3-diazo-4-oxopentane-1,2-diyl diacetate (7): To a solution of methyl diazodiol 4 (89 mg, 0.62 mmol), DMAP (15 mg, 0.2 equiv.) and suspended 4 A molecular sieves (0.2 g) in anhydrous dichloromethane (DCM) was added acetic anhydride (0.12 mL, 2 equiv.). The reaction was gently stirred at room temperature overnight. The reaction was quenched with saturated aqueous NaHCO$_3$ solution. The organic and aqueous layers were separated and the organic layer was washed with brine and dried over anhydrous MgSO$_4$. The solvent was removed in vacuo and the residue was purified on silica gel, using 3:4 ethyl acetate/hexane as the mobile phase. The product eluted as a yellow oil (yield=90 mg, 64%).

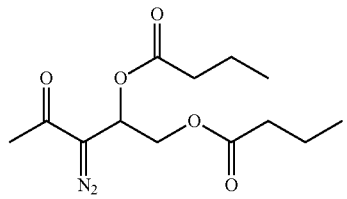

3-diazo-4-oxopentane-1,2-diyl dibutyrate (8): To a solution of methyl diazodiol 4 (23 mg, 0.16 mmol), DMAP (4 mg, 0.2 equiv.) and suspended 4 A molecular sieves (0.1 g) in anhydrous dichloromethane (DCM) was added butyric anhydride (0.05 mL, 2 equiv.). The reaction was stirred at room temperature overnight. The reaction was quenched with saturated aqueous NaHCO$_3$ solution. The organic and aqueous layers were separated and the organic layer was washed with brine and dried over anhydrous MgSO$_4$. The solvent was removed in vacuo and the residue was purified on silica gel, using 1:5 ethyl acetate/hexane as the mobile phase. The product eluted as a yellow oil (yield=23 mg, 51%).

3-diazo-4-oxopentane-1,2-diyl dipentanoate (9): To a solution of methyl diazodiol 4 (23 mg, 0.16 mmol), DMAP (4 mg, 0.2 equiv.) and suspended 4 A molecular sieves (0.1 g) in anhydrous dichloromethane (DCM) was added butyric anhydride (0.05 mL, 2 equiv.). The reaction was stirred at room temperature overnight. The reaction was quenched with saturated aqueous NaHCO$_3$ solution. The organic and aqueous layers were separated and the organic layer was washed with brine and dried over anhydrous MgSO$_4$. The solvent was removed in vacuo and the residue was purified on silica gel, using 1:5 ethyl acetate/hexane as the mobile phase. The product eluted as a yellow oil (yield=27 mg, 54%).

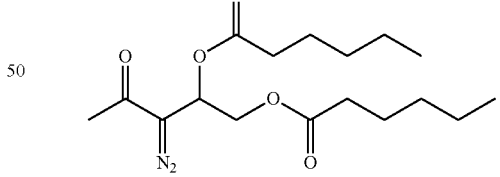

3-diazo-4-oxopentane-1,2-diyl dihexanoate (10): To a solution of methyl diazodiol 4 (23 mg, 0.16 mmol), DMAP (4 mg, 0.2 equiv.) and suspended 4 A molecular sieves (0.1 g) in anhydrous dichloromethane (DCM) was added butyric anhydride (0.05 ml, 2 equiv.). The reaction was stirred at room temperature overnight. The reaction was quenched with saturated aqueous NaHCO$_3$ solution. The organic and aqueous layers were separated and the organic layer was washed with brine and dried over anhydrous MgSO$_4$. The solvent was removed in vacuo and the residue was purified on silica gel, using 1:5 ethyl acetate/hexane as the mobile phase. The product eluted as a yellow oil (yield=38 mg, 67%).

Oxidation of Diazo Moiety into Carbonyl:

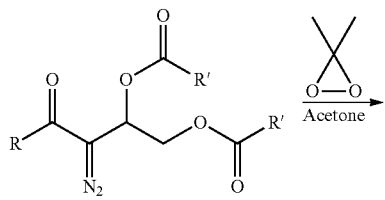

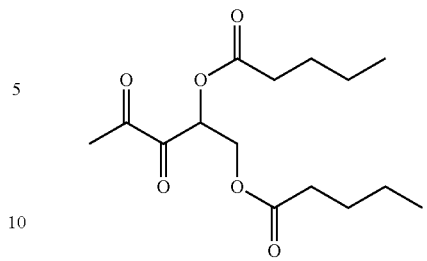

3,4-dioxopentane-1,2-diyl dipentanoate (21): To a solution of methyl diazo dipentanoate 9 (27 mg, 0.086 mmol) in acetone (1 mL) was added dimethyldioxirane acetone solution (2.5 mL, ca. 0.07-0.09 M). The resulting mixture was stirred for 1 h and solvent and excess reagents were removed under reduced pressure to obtain 21 as bright yellow oil (yield=26 mg, quantitative).

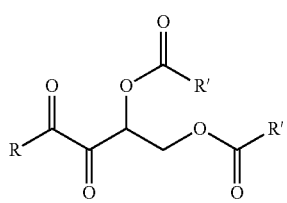

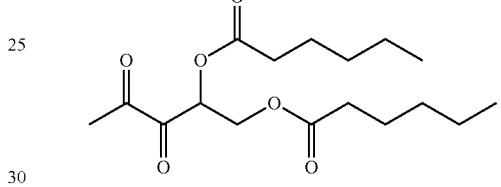

3,4-dioxopentane-1,2-diyl dihexanoate (22): To a solution of methyl diazo dihexanoate 10 (38 mg, 0.112 mmol) in acetone (1 mL) was added dimethyldioxirane acetone solution (2.5 mL, ca. 0.07-0.09 M). The resulting mixture was stirred for 1 h and solvent and excess reagents were removed under reduced pressure to obtain 22 as bright yellow oil (yield=36.8 mg, quantitative).

NMR and MS Data:

NMR spectra were measured on Bruker AV-400, Bruker DRX-400 ($^1$H at 400 MHz, $^{13}$C at 100 MHz). Data for 1H-NMR spectra are reported as follows: chemical shift (ppm, relative to residual solvent peaks or indicated external standards; s=singlet, t=triplets, m=multiplet), coupling constant (Hz), and integration. Data for $^{13}$C-NMR are reported in terms of chemical shift (ppm) relative to residual solvent peak. Mass spectra (MS) were recorded by JEOL AccuTOF-CS (ESI positive, needle voltage 1800~2400 eV).

3,4-dioxopentane-1,2-diyl diacetate (19): To a solution of methyl diazo diacetate 7 (20 mg, 0.088 mmol) in acetone (1 mL) was added dimethyldioxirane acetone solution (2.5 mL, ca. 0.07-0.09 M). The resulting mixture was stirred for 1 h and solvent and excess reagents were removed under reduced pressure to obtain 19 as bright yellow oil (yield=19 mg, quantitative).

Additional MS characterization was done by adding phenyl diamine to the diketones and stirred overnight to convert the diketones into quinoxalines, see Scheme below (this is a standard practice). MS data is reported for the quinoxaline derivatives.

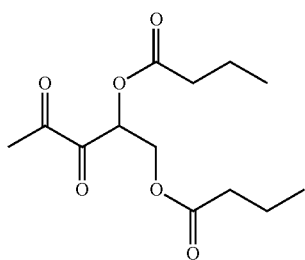

3,4-dioxopentane-1,2-diyl dibutyrate (20): To a solution of methyl diazo dibutyrate 8 (23 mg, 0.081 mmol) in acetone (1 mL) was added dimethyldioxirane acetone solution (2.5 mL, ca. 0.07-0.09 M). The resulting mixture was stirred for 1 h and solvent and excess reagents were removed under reduced pressure to obtain 20 as bright yellow oil (yield=22 mg, quantitative).

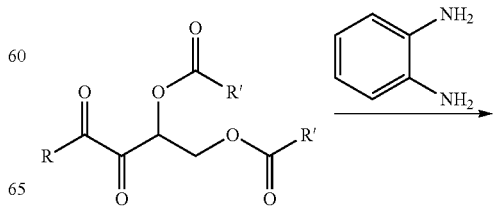

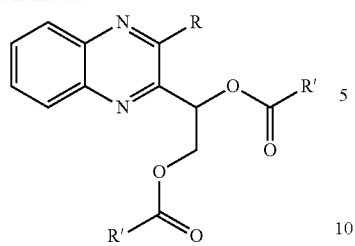

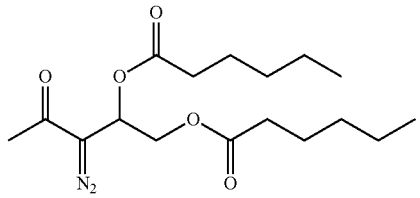

3-diazo-4-oxopentane-1,2-diyl dihexanoate (10): ¹H NMR (CDCl₃, 400 MHz) δ: 5.92-5.82 (m, 1H), 4.55-4.42 (m, 1H), 4.37-4.26 (m, 1H), 2.40-2.28 (m, 4H), 2.26 (s, 3H), 1.68-1.56 (m, 4H), 1.38-1.25 (m, 8H), 0.96-0.83 (m, 6H). ¹³C NMR (CDCl₃, 100 MHz) δ 173.4, 172.9, 66.0, 63.7, 34.4, 34.3, 31.6, 25.9, 24.9, 22.7, 14.3.

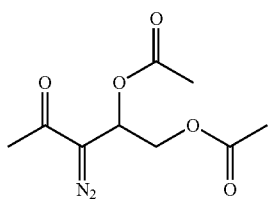

3-diazo-4-oxopentane-1,2-diyl diacetate (7): ¹H NMR (CDCl₃, 400 MHz) δ: 5.85-5.73 (m, 1H), 4.45-4.34 (m, 1H), 4.31-4.17 (m, 1H), 2.19 (s, 3H), 2.03 (s, 3H), 2.01 (s, 3H). ¹³C NMR (CDCl₃, 100 MHz) δ: 188.6, 170.1, 169.6, 68.5, 65.7, 63.5, 25.4, 20.7, 20.5.

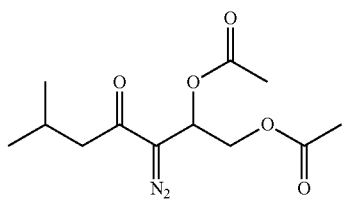

3-diazo-6-methyl-4-oxoheptane-1,2-diyl diacetate (11): ¹H NMR (CDCl₃, 400 MHz) δ 5.85-5.76 (m, 1H), 4.44-4.34 (m, 1H), 4.32-4.21 (m, 1H), 2.28 (d, J=6.7 Hz, 2H), 2.15-2.07 (m, 1H), 2.03 (s, 3H), 2.01 (s, 3H), 0.89 (d, J=8.0 Hz, 6H). ¹³C NMR (CDCl₃, 100 MHz) δ 170.5, 169.9, 66.3, 63.8, 47.1, 26.0, 22.8, 22.7, 21.0, 20.8.

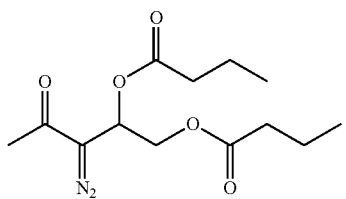

3-diazo-4-oxopentane-1,2-diyl dibutyrate (8): ¹H NMR (CDCl₃, 400 MHz) δ: 5.93-5.83 (m, 1H), 4.55-4.43 (m, 1H), 4.38-4.27 (m, 1H), 2.38-2.28 (m, 4H), 2.26 (s, 3H), 1.73-1.59 (m, 4H), 1.01-0.89 (m, 6H). ¹³C NMR (CDCl₃, 100 MHz) δ: 173.3, 172.7, 65.9, 63.7, 37.0, 36.3, 36.2, 31.3, 25.9, 18.7, 14.0, 13.9.

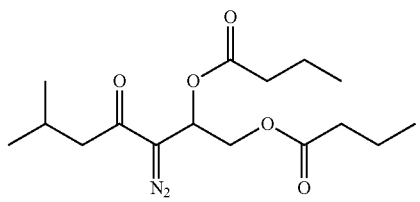

3-diazo-6-methyl-4-oxoheptane-1,2-diyl dibutyrate (12): ¹H NMR (CDCl₃, 400 MHz) δ 5.92-5.81 (m, 1H), 4.50-4.39 (m, 1H), 4.34-4.22 (m, 1H), 2.37-2.21 (m, 6H), 2.18-2.04 (m, 1H), 1.69-1.54 (m, 4H), 0.96-0.85 (m, 12H). ¹³C NMR (CDCl₃, 100 MHz) δ 173.2, 172.6, 66.1, 63.6, 47.2, 36.2, 36.1, 26.0, 22.8, 22.7, 18.7, 18.6, 13.9.

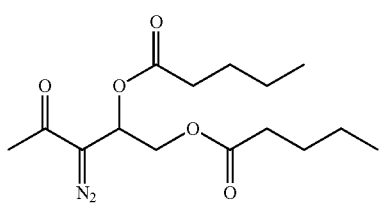

3-diazo-4-oxopentane-1,2-diyl dipentanoate (9): ¹H NMR (CDCl₃, 400 MHz) δ: 5.93-5.82 (m, 1H), 4.54-4.43 (m, 1H), 4.37-4.26 (m, 1H), 2.41-2.29 (m, 4H), 2.26 (s, 3H), 1.67-1.54 (m, 4H), 1.42-1.28 (m, 4H), 0.97-0.85 (m, 6H). ¹³C NMR (CDCl₃, 100 MHz) δ: 189.0, 173.4, 172.9, 67.0, 66.0, 63.7, 34.1, 34.0, 27.2, 25.9, 22.6, 22.5, 14.0.

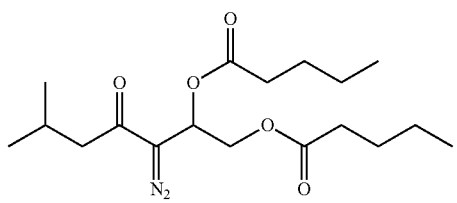

3-diazo-6-methyl-4-oxoheptane-1,2-diyl dipentanoate (13): ¹H NMR (CDCl₃, 400 MHz) δ 5.94-5.82 (m, 1H), 4.53-4.44 (m, 1H), 4.40-4.29 (m, 1H), 2.41-2.29 (m, 6H), 2.23-2.10 (m, 1H), 1.67-1.56 (m, 4H), 1.41-1.31 (m, 4H), 0.98-0.89 (m, 12H). ¹³C NMR (CDCl₃, 100 MHz) δ 180.0, 173.5, 172.9, 66.2, 63.7, 47.3, 34.2, 34.1, 34.0, 27.3, 22.6, 22.5, 14.1, 14.0.

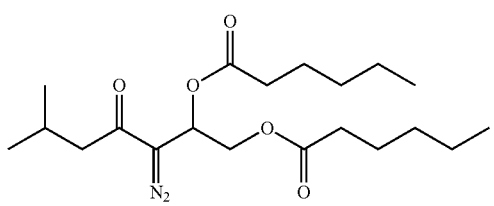

3-diazo-6-methyl-4-oxoheptane-1,2-diyl dihexanoate (14): ¹H NMR (CDCl₃, 400 MHz) δ 5.96-5.82 (m, 1H), 4.54-4.42 (m, 1H), 4.40-4.26 (m, 1H), 2.42-2.26 (m, 6H), 2.22-2.09 (m, 1H), 1.68-1.56 (m, 4H), 1.38-1.22 (m, 8H), 1.00-0.93 (m, 6H), 0.93-0.85 (m, 6H). ¹³C NMR (CDCl₃, 100 MHz) δ 173.4, 172.8, 66.2, 63.7, 47.3, 34.3, 31.6, 24.9, 22.7, 14.3.

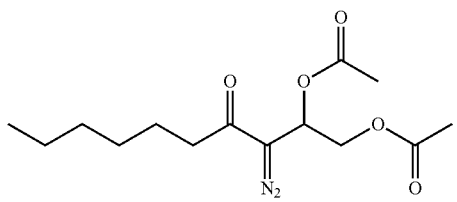

3-diazo-4-oxodecane-1,2-diyl diacetate (15): ¹H NMR (CDCl₃, 400 MHz) δ 5.95-5.85 (m, 1H), 4.54-4.43 (m, 1H), 4.41-4.29 (m, 1H), 2.49 (t, J=7.3 Hz, 2H), 2.12 (s, 3H), 2.11 (s, 3H), 1.69-1.60 (m, 2H), 1.38-1.27 (m, 6H), 0.91 (t, J=6.9 Hz, 3H). ¹³C NMR (CDCl₃, 100 MHz) δ 170.7, 170.1, 66.4, 64.0, 38.6, 31.9, 29.2, 24.8, 22.9, 21.2, 21.0, 14.4.

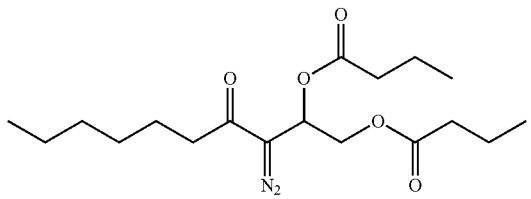

3-diazo-4-oxodecane-1,2-diyl dibutyrate (16): ¹H NMR (CDCl₃, 400 MHz) δ 5.96-5.85 (m, 1H), 4.56-4.46 (m, 1H), 4.40-4.28 (m, 1H), 2.53-2.43 (m, 2H), 2.38-2.29 (m, 4H), 1.72-1.61 (m, 6H), 1.37-1.25 (m, 6H), 1.02-0.94 (m, 6H), 0.94-0.87 (m, 3H). ¹³C NMR (CDCl₃, 100 MHz) δ 173.3, 172.7, 66.2, 63.7, 36.3, 36.2, 31.9, 29.2, 24.9, 22.9, 18.7, 14.4, 14.0.

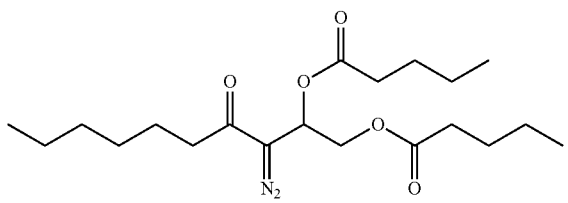

3-diazo-4-oxodecane-1,2-diyl dipentanoate (17): ¹H NMR (CDCl₃, 400 MHz) δ 5.95-5.84 (m, 1H), 4.56-4.43 (m, 1H), 4.40-4.27 (m, 1H), 2.55-2.44 (m, 2H), 2.40-2.33 (m, 6H), 1.69-1.59 (m, 6H), 1.43-1.28 (m, 8H), 0.98-0.88 (m, 9H). ¹³C NMR (CDCl₃, 100 MHz) δ 180.7, 173.5, 172.9, 66.2, 63.7, 34.2, 34.1, 31.9, 29.2, 27.3, 27.1, 24.9, 22.9, 22.6, 14.1, 14.1.

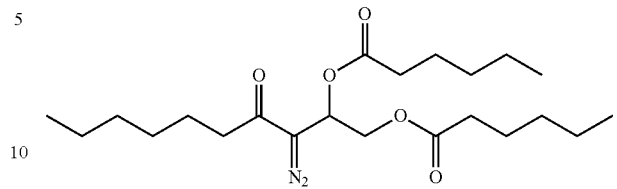

3-diazo-4-oxodecane-1,2-diyl dihexanoate (18): ¹H NMR (CDCl₃, 400 MHz) δ 5.97-5.83 (m, 1H), 4.56-4.42 (m, 1H), 4.40-4.27 (m, 1H), 2.57-2.2.43 (m, 2H), 2.43-2.28 (m, 6H), 1.73-1.57 (m, 6H), 1.40-1.26 (m, 12H), 0.97-0.86 (m, 9H). ¹³C NMR (CDCl₃, 100 MHz) δ 180.2, 173.5, 172.9, 66.2, 63.7, 34.4, 31.6, 24.9, 24.8, 22.9, 22.7, 14.4, 14.3.

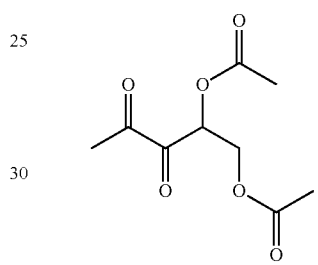

3,4-dioxopentane-1,2-diyl diacetate (19): ¹H NMR (CDCl₃, 400 MHz) δ 5.88-5.83 (m, 1H), 4.72-4.64 (m, 1H), 4.40-4.32 (m, 1H), 2.39 (s, 3H), 2.18 (s, 3H), 2.06 (s, 3H). ¹³C NMR (CDCl₃, 100 MHz) δ 196.3, 190.4, 171.5, 170.5, 62.7, 24.1, 21.0, 20.7. Derivatization using 1,2-diaminobenzene MS (ESI): Calcd for [C₁₅H₁₆N₂O₄+H]⁺ 289.1188. found 289.1234.

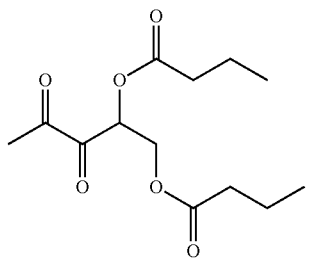 [SMILES: CCCC(=O)OCC(OC(=O)CCC)C(=O)C(C)=O]

3,4-dioxopentane-1,2-diyl dibutyrate (20): ¹H NMR (CDCl₃, 400 MHz) δ 5.90-5.84 (m, 1H), 4.75-4.66 (m, 1H), 4.41-4.32 (m, 1H), 2.46-2.40 (m, 2H), 2.39 (s, 3H), 2.29 (t, J=7.4 Hz, 2H), 1.73-1.66 (m, 2H), 1.66-1.58 (m, 2H), 0.99 (t, J=7.4 Hz, 3H), 0.94 (t, J=7.4 Hz, 3H). ¹³C NMR (CDCl₃, 100 MHz) δ 196.3, 190.5, 174.1, 173.1, 62.5, 36.1, 35.8, 24.1, 18.7, 18.6, 13.9. Derivatization using 1,2-diaminobenzene MS (ESI): Calcd for [C₁₉H₂₄N₂O₄+H]⁺ 345.1814. found 345.1709.

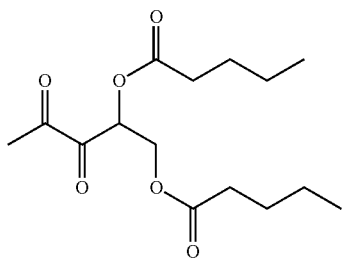 [SMILES: CCCCC(=O)OCC(OC(=O)CCCC)C(=O)C(C)=O]

3,4-dioxopentane-1,2-diyl dipentanoate (21): $^1$H NMR (CDCl$_3$, 400 MHz) δ 5.89-5.83 (m, 1H), 4.74-4.65 (m, 1H), 4.41-4.32 (m, 1H), 2.48-2.41 (m, 2H), 2.40 (s, 3H), 2.34-2.28 (m, 2H), 1.70-1.61 (m, 2H), 1.61-1.53 (m, 2H), 1.44-1.30 (m, 4H), 0.98-0.89 (m, 6H). $^{13}$C NMR (CDCl$_3$, 100 MHz) δ 196.3, 190.5, 174.3, 173.3, 62.5, 34.0, 33.7, 27.2, 24.1, 22.5, 14.1, 14.0. Derivatization using 1,2-diaminobenzene MS (ESI): Calcd for [C$_{21}$H$_{28}$N$_2$O$_4$+H]$^+$ 373.2127. found 373.2109.

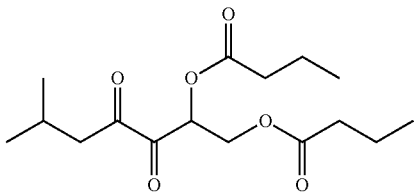

6-methyl-3,4-dioxoheptane-1,2-diyl dibutyrate (24): $^1$H NMR (CDCl$_3$, 400 MHz) δ 5.89-5.82 (m, 1H), 4.70-4.62 (m, 1H), 4.46-4.37 (m, 1H), 2.77-2.58 (m, 2H), 2.46-2.34 (m, 2H), 2.33-2.24 (m, 2H), 2.23-2.12 (m, 1H), 1.74-1.58 (m, 4H), 1.02-0.90 (m, 12H). $^{13}$C NMR (CDCl$_3$, 100 MHz) δ 198.3, 191.1, 173.8, 173.1, 62.5, 45.0, 36.1, 35.9, 24.4, 22.9, 22.8, 18.7, 18.6, 13.9. Derivatization using 1,2-diaminobenzene MS (ESI): Calcd for [C$_{22}$H$_{30}$N$_2$O$_4$+H]$^+$ 387.2284. found 387.2244.

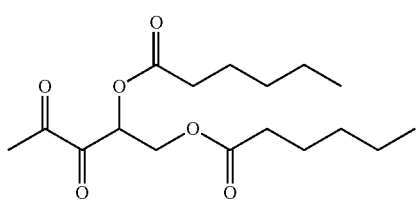 [SMILES: CCCCCC(=O)OCC(OC(=O)CCCCC)C(=O)C(C)=O]

3,4-dioxopentane-1,2-diyl dihexanoate (22): $^1$H NMR (CDCl$_3$, 400 MHz) δ 5.91-5.82 (m, 1H), 4.75-4.64 (m, 1H), 4.42-4.30 (m, 1H), 2.47-2.40 (m, 2H), 2.39 (s, 3H), 2.33-2.25 (m, 3H), 1.72-1.62 (m, 2H), 1.62-1.53 (m, 2H), 1.40-1.21 (m, 8H), 0.97-0.83 (m, 6H). $^{13}$C NMR (CDCl$_3$, 100 MHz) δ 196.3, 190.5, 174.2, 173.3, 72.9, 62.5, 34.2, 33.9, 31.5, 24.8, 24.1, 22.7, 22.6, 14.3. Derivatization using 1,2-diaminobenzene MS (ESI): Calcd for [C$_{23}$H$_{32}$N$_2$O$_4$+H]$^+$ 401.2440. found 401.2479.

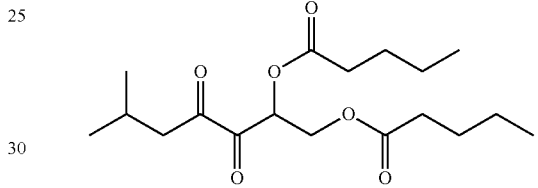

6-methyl-3,4-dioxoheptane-1,2-diyl dipentanoate (25): $^1$H NMR (CDCl$_3$, 400 MHz) 5.89-5.82 (m, 1H), 4.70-4.61 (m, 1H), 4.46-4.37 (m, 1H), 2.78-2.58 (m, 2H), 2.48-2.38 (m, 2H), 2.35-2.25 (m, 2H), 2.25-2.13 (m, 1H), 1.68-1.54 (m, 4H), 1.43-1.30 (m, 4H), 1.01-0.89 (m, 12H). δ. $^{13}$C NMR (CDCl$_3$, 100 MHz) δ 198.3, 191.1, 174.0, 173.3, 62.5, 45.0, 34.0, 27.2, 22.9, 22.5, 14.1, 14.0. Derivatization using 1,2-diaminobenzene MS (ESI): Calcd for [C$_{24}$H$_{34}$N$_2$O$_4$+H]$^+$ 415.2597. found 415.2499.

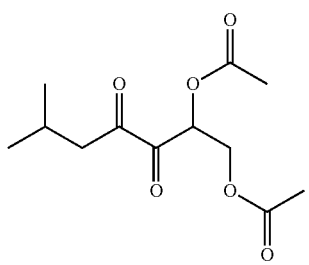 [SMILES: CC(=O)OCC(OC(C)=O)C(=O)C(=O)CC(C)C]

6-methyl-3,4-dioxoheptane-1,2-diyl diacetate (23): $^1$H NMR (CDCl$_3$, 400 MHz) δ 5.89-5.83 (m, 1H), 4.70-4.61 (m, 1H), 4.45-4.36 (m, 1H), 2.78-2.58 (m, 2H), 2.23-2.19 (m, 1H), 2.19 (s, 3H), 2.06 (s, 3H), 0.98 (d, J=2.7 Hz, 3H), 0.97 (d, J=2.7 Hz, 3H). $^{13}$C NMR (CDCl$_3$, 100 MHz) δ 198.2, 191.0, 171.2, 170.4, 73.2, 62.7, 45.0, 24.4, 22.9, 21.0, 20.7. Derivatization using 1,2-diaminobenzene MS (ESI): Calcd for [C$_{18}$H$_{22}$N$_2$O$_4$+H]$^+$ 331.1658. found 331.1740.

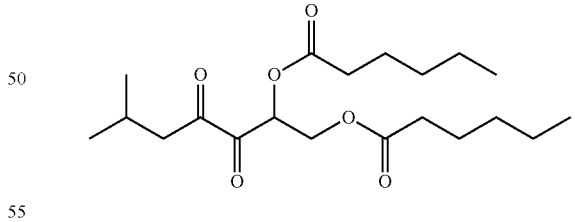

6-methyl-3,4-dioxoheptane-1,2-diyl dihexanoate (26): $^1$H NMR (CDCl$_3$, 400 MHz) δ 5.89-5.82 (m, 1H), 4.70-4.60 (m, 1H), 4.46-4.36 (m, 1H), 2.77-2.57 (m, 2H), 2.33-2.25 (m, 2H), 2.23-2.12 (m, 1H), 1.70-1.54 (m, 4H), 1.39-1.25 (m, 8H), 1.02-0.95 (m, 6H), 0.95-0.87 (m, 6H). $^{13}$C NMR (CDCl$_3$, 100 MHz) δ 198.3, 191.1, 174.0, 173.3, 62.5, 34.2, 31.5, 24.8, 22.9, 22.7, 14.3. Derivatization using 1,2-diaminobenzene MS (ESI): Calcd for [C$_{26}$H$_{38}$N$_2$O$_4$+H]$^+$ 443.2910. found 443.2855.

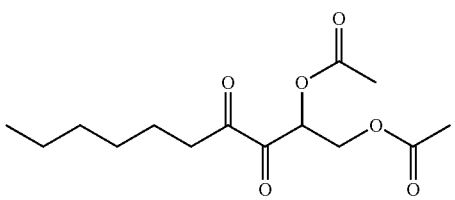 [SMILES: CCCCCCC(=O)C(=O)C(COC(C)=O)OC(C)=O]

3,4-dioxodecane-1,2-diyl diacetate (27): ¹H NMR (CDCl₃, 400 MHz) δ 5.90-5.84 (m, 1H), 4.71-4.64 (m, 1H), 4.45-4.36 (m, 1H), 2.87-2.72 (m, 2H), 2.19 (s, 3H), 2.17 (s, 3H), 1.68-1.58 (m, 2H), 1.38-1.27 (m, 6H), 0.94-0.87 (m, 3H). ¹³C NMR (CDCl₃, 100 MHz) δ 198.7, 190.9, 171.2, 170.4, 73.2, 62.7, 36.5, 31.9, 29.1, 23.1, 22.9, 21.0, 20.8, 14.4. Derivatization using 1,2-diaminobenzene MS (ESI): Calcd for [C₂₀H₂₆N₂O₄+H]⁺ 359.1971. found 359.1903.

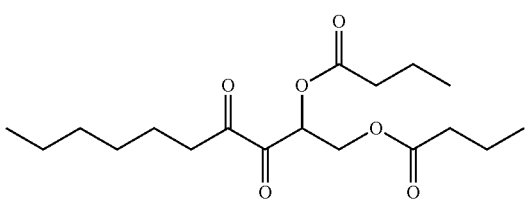 [SMILES: CCCCCCC(=O)C(=O)C(COC(=O)CCC)OC(=O)CCC]

3,4-dioxodecane-1,2-diyl dibutyrate (28): ¹H NMR (CDCl₃, 400 MHz) δ 5.91-5.84 (m, 1H), 4.72-4.64 (m, 1H), 4.46-4.37 (m, 1H), 2.86-2.2.72 (m, 2H), 2.47-2.38 (m, 2H), 2.33-2.24 (m, 2H), 1.76-1.1.60 (m, 6H), 1.38-1.27 (m, 6H), 1.04-0.88 (m, 9H). ¹³C NMR (CDCl₃, 100 MHz) δ 198.7, 191.0, 173.9, 173.1, 73.1, 62.5, 36.5, 36.2, 35.9, 31.9, 29.1, 23.1, 22.9, 18.7, 14.4, 14.0. Derivatization using 1,2-diaminobenzene MS (ESI): Calcd for [C₂₄H₃₄N₂O₄+H]⁺ 415.2597. found 415.2528.

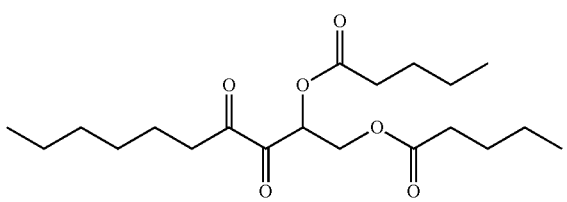 [SMILES: CCCCCCC(=O)C(=O)C(COC(=O)CCCC)OC(=O)CCCC]

3,4-dioxodecane-1,2-diyl dipentanoate (29): ¹H NMR (CDCl₃, 400 MHz) δ 5.90-5.83 (m, 1H), 4.71-4.63 (m, 1H), 4.45-4.37 (m, 1H), 2.85-2.72 (m, 2H), 2.48-2.40 (m, 2H), 2.40-2.34 (m, 2H), 2.34-2.27 (m, 2H), 1.69-1.57 (m, 6H), 1.45-1.30 (m, 8H), 0.97-0.89 (m, 9H). ¹³C NMR (CDCl₃, 100 MHz) δ 198.7, 191.0, 174.1, 173.3, 73.1, 62.5, 36.5, 34.0, 33.8, 31.9, 29.1, 27.2, 23.1, 22.9, 22.6, 22.5, 14.4, 14.1. Derivatization using 1,2-diaminobenzene MS (ESI): Calcd for [C₂₆H₃₈N₂O₄+H]⁺ 443.2910. found 443.2867.

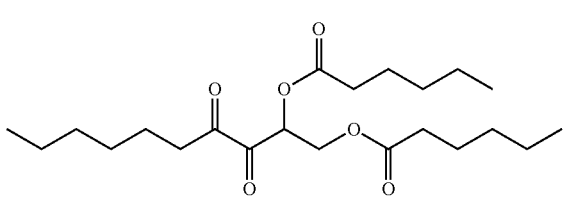 [SMILES: CCCCCCC(=O)C(=O)C(COC(=O)CCCCC)OC(=O)CCCCC]

3,4-dioxodecane-1,2-diyl dihexanoate (30): ¹H NMR (CDCl₃, 400 MHz) δ 5.90-5.83 (m, 1H), 4.72-4.62 (m, 1H), 4.45-4.36 (m, 1H), 2.86-2.71 (m, 2H), 2.48-2.40 (m, 2H), 2.40-2.33 (m, 2H), 2.33-2.25 (m, 2H), 1.71-1.58 (m, 6H), 1.39-1.27 (m, 12H), 0.96-0.87 (m, 9H). ¹³C NMR (CDCl₃, 100 MHz) δ 198.7, 191.0, 174.1, 173.3, 73.1, 62.5, 36.5, 34.3, 34.0, 31.9, 31.6, 31.5, 29.1, 24.8, 23.1, 22.9, 22.7, 14.4, 14.3. Derivatization using 1,2-diaminobenzene MS (ESI): Calcd for [C₂₈H₄₂N₂O₄+H]⁺ 471.3223. found 471.3176.

EXAMPLE 6

This Example provides a description of the synthesis and biological evaluation of an expanded set of AI-2 analogs, both biochemically and as interrupters of cross-talk in a polymicrobial system comprising *E. coli*, *S. typhimurium* and *P. aeruginosa*.

TABLE 4

List of strains and cells used in this study

| Strain, plasmid or primer | Relevant genotype and/or property |
|---|---|
| *Escherichia coli* strains | |
| W3110 | Wild type |
| LW7 | W3110 ΔlacU160-tna2 ΔluxS :: Kan |
| ZK126 | W3110 ΔlacU169-tna2 |
| LW8 | ZK126 ΔlsrR::Kan |
| *Salmonella typhimurium* strains | |
| MET715 | rpsl putRA :: Kan-lsr-lacZYA luxS :: T-POP |
| MET708 | rpsl putRA :: Kan-lsr-lacZYA |
| *P. aeruginosa* Strains | |
| PAO1 | Wild Type |
| Plasmids | |
| pLW11 | galK'-lacZYA transcriptional fusion vector, containing lsrACDBFG promoter region, Ampʳ |
| pCT6 | pFZY1 derivative, containing lsrR and lsrR promoter region fused with T7RPol, Apʳ |
| pET-dsRED | pET200 derivative, containing RFP, Kmʳ |

Figure 31:
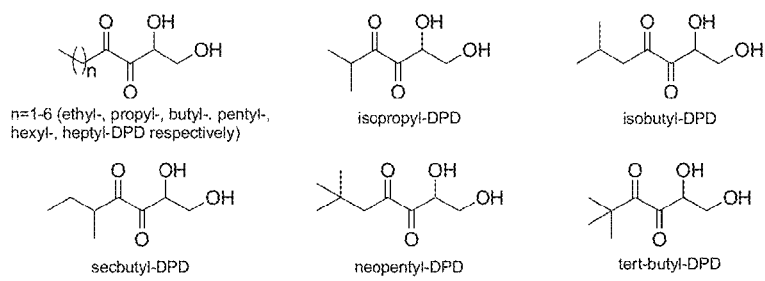
FIG. 31. Analog synthesis scheme and analog structures. a) previously synthesized linear and branched analogs; b) newly synthesized cyclic and aromatic analogs.
Figure 31:
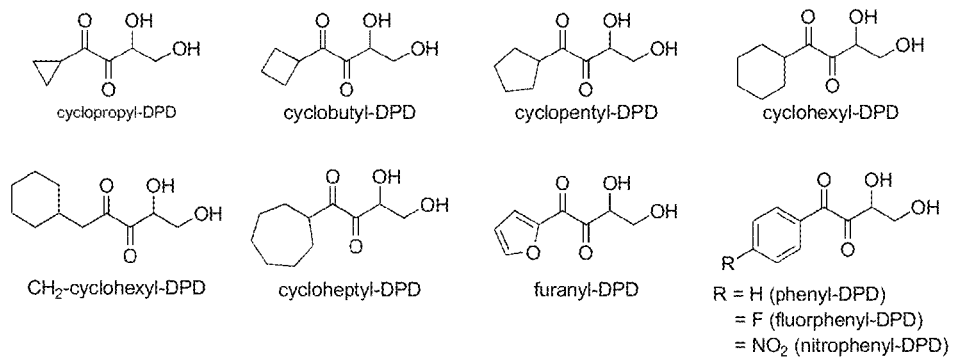

It will be apparent from the foregoing description in this Example that we have synthesized cyclic and aromatic AI-2 analogs. C-1 alkyl AI-2 analogs (FIG. 31, panel a) were synthesized following the diazocarbonyl aldol methodology. This methodology was adapted to make a variety of cyclic and aromatic AI-2 analogs, starting from the requisite acid chlorides, which are commercially available. Briefly, a DBU-catalyzed addition of (OTBS)-acetaldehyde to diazocarbonyls (generated from the addition of diazomethane to acid chlorides) afforded the protected diazo intermediates. Without isolation of these products, TBAF-deprotection was performed to afford diazodiol intermediates. Oxidation of these diazodiols into DPD proceeded quantitatively with excess DMDO and the excess reagent was evaporated to give the desired cyclic and aromatic DPD analogs. FIG. 31 (panel b) depicts eight new AI-2 analogs; their effects on three different bacteria: *E. coli*, *S. typhimurium* and *P. aeruginosa* were tested.

Figure 32:
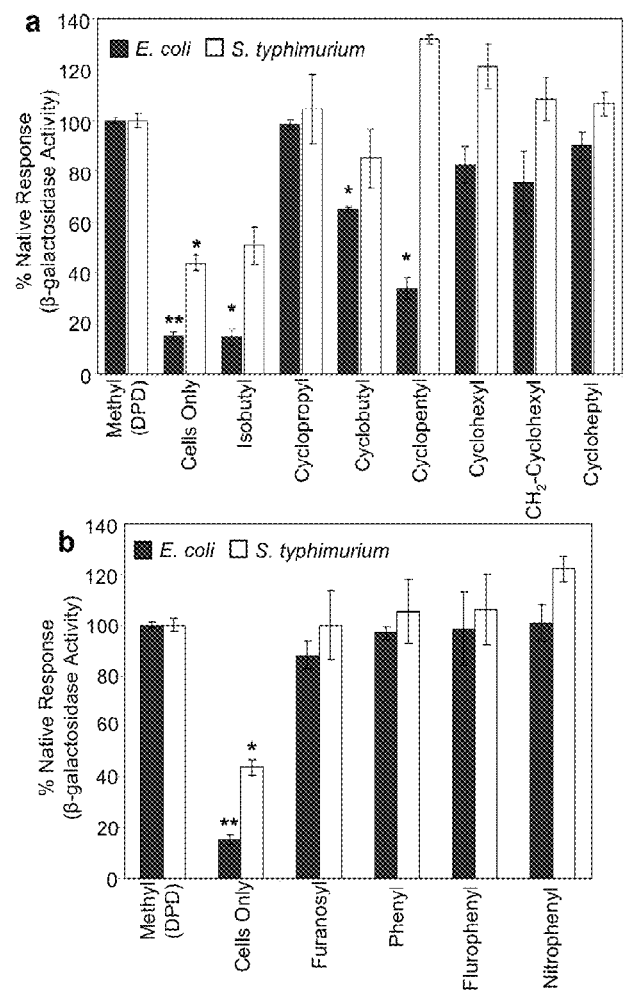
FIG. 32. Competitive inhibition of QS signaling by analogs in the presence of stoichiometric amounts of DPD in *E. coli* and *S. typhimurium*; AI-2 dependent β-galactosidase production in *E. coli* LW7 pLW11 and *S. typhimurium* MET715 (both luxS⁻) a) cyclic analogs (20 μM b) aromatic analogs (20 μM) (normalized to the native *E. coli* (LW7) response (1304 Miller units) and the *S. typhimurium* (MET715) response (3480 Miller units) following 20 μM DPD addition. Controls denoted "Cells Only" represent the response of the luxS⁻ cells when no compounds were added; controls denoted "Methyl (DPD)" indicate the response of luxS⁻ cells to exogenously added AI-2 (DPD). (* indicates $p<0.05$ and ** indicates $p<0.01$ for an unpaired t test of the particular analog as compared to the "Methyl (DPD)" response).

Effect of cyclic and aromatic DPD analogs on β-galactosidase production in *E. coli* and *S. typhimurium*. Cyclic and aromatic analogs were tested for their modulation of QS in *E. coli* and *S. typhimurium*. Both *E. coli* LW7 (luxS⁻) and *S. typhimurium* MET715 (luxS⁻) synthesize β-galactosidase in response to AI-2 by de-repressing lsr transcription. The addition of analogs to these cells yielded no increased LacZ activity relative to mock addition controls, hence they had no lsr agonist activity (not shown). Results in FIG. 32 depict responses to analogs (20 μM) added with 20 μM AI-2 (synthetic DPD). The "Methyl (DPD)" data are a control, demonstrating the elicitation of lsr gene expression (QS response)

due to exogenously added chemically synthesized AI-2; the "Cells Only" controls depicts the background level of β-galactosidase without addition of either analog or AI-2 (leaky transcription). In *E. coli* cultures, simultaneous addition of 20 μM DPD (eliciting response) and 20 uM cyclopentyl-DPD (quenching response) resulted in over 60% reduction in lsr promoter activity. Interestingly, nearly all the cyclic analogs tested (with the exception of cyclopropyl-DPD) attenuated the QS response in *E. coli*. The aromatic analogs exhibited minimal (furanosyl-DPD) or no (phenyl, fluorophenyl, and nitrophenyl) effect. In *S. typhimurium*, which has significant homology in operon structure, the effects were strikingly different, particularly for the cyclic analogs. Cyclopentyl-DPD, cyclohexyl-DPD, elicited increased expression suggesting synergistic agonist activity due to the presence of both DPD and analog. Effects of the other cyclic compounds when added to *Salmonella* with DPD were no different than DPD alone; this was distinctly different than *E. coli*. On the other hand, with the exception of nitrophenyl-DPD, results for the aromatic C-1 analogs were identical to those of *E. coli*, exhibiting no apparent effect on the QS response. Nitrophenyl-DPD addition resulted in increased QS response in *Salmonella*.

Using a variety of linear or branched chain C1 DPD analogs, it was indicated that of the analogs affecting *E. coli* and *S. typhimurium* QS activity (e.g. isobutyl-DPD, FIG. 32a) all worked through the native AI-2 signal processing system involving the kinase, LsrK, and the transcriptional regulator, LsrR. Because the analogs contained C1 chains that were dissimilar to the native DPD, both *E. coli* LsrK and LsrR were somehow promiscuous. The new data with the C1 cyclic alkyl analogs of AI-2 reveal that these *E. coli* AI-2 processing/binding proteins are not entirely promiscuous since only two cyclic analogs exhibited an effect. When coupled with the other Examples described herein, the data in this Example indicate that C1 acyl DPD analogs (both linear and branched chain) may fit into an active site pocket of the AI-2 processing/binding proteins whereas some of the cyclic analogs do not have this capability. It was investigated whether the cyclic and aromatic analogs were also processed via LsrR and LsrK.

Figure 33:
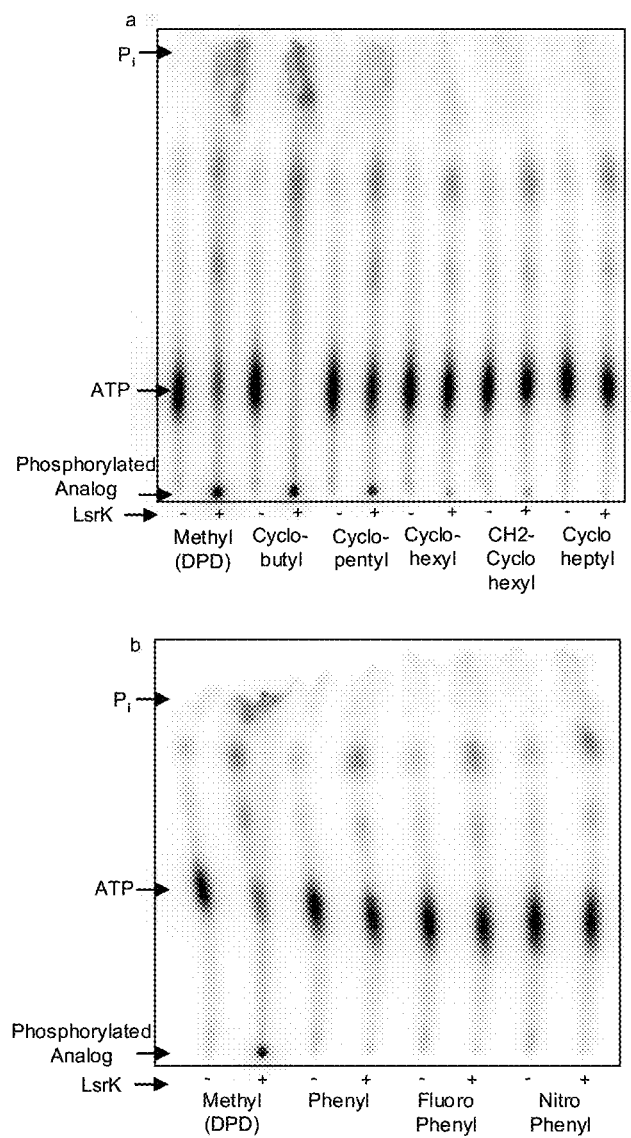
FIG. 33. In vitro phosphorylation of analogs by LsrK. Thin layer chromatography (TLC) analysis of LsrK mediated analog phosphorylation. a) Cyclic analogs-Methyl (DPD), cyclobutyl-DPD, cyclopentyl-DPD, cyclohexyl-DPD, $CH_2$-cyclohexyl-DPD, cycloheptyl-DPD and b) aromatic-phenyl, fluorophenyl, nitrophenyl DPD treated with LsrK.

Biological evaluations of DPD analogs on *E. coli* AI-2 Processing Enzymes (LsrK) and AI-2 Receptor (LsrR): Shown in other Examples was that analogs most effective in inhibiting lsr expression in *E. coli* were also phosphorylated by LsrK. The ability of *E. coli* LsrK to phosphorylate the cyclic analogs (both alkyl and aromatic) was tested by incubation with LsrK in vitro for one hour using a method adapted from known techniuqes. Cyclobutyl-DPD and cyclopentyl-DPD, which were significantly phosphorylated (FIG. 33, panel a) also inhibit lsr expression in *E. coli* (FIG. 32, panel a). Cyclohexyl-DPD and CH$_2$-cyclohexyl-DPD were weakly phosphorylated (FIG. 33, panel a) and attenuated lsr expression in *E. coli* to a lesser extent. Neither Cycloheptyl-DPD nor the aromatic analogs were phosphorylated (FIG. 33, panel a and b); nor did they affect LsrR-controlled transcription in *E. coli* (FIG. 32, panel a). IC$_{50}$ values of all analogs were evaluated; those that were significantly phosphorylated had significantly lower IC$_{50}$ than those not phosphorylated, (i.e. IC$_{50}$ for Cyclopentyl-DPD was 2.4 μM compared to phenyl-DPD, which was >40 μM). Isobutyl-DPD was the most efficient inhibitor, having an IC$_{50}$ in the nanomolar range. These observations support the notion that the active DPD analog species that are acting to repress lsr expression are the phosphorylated forms.

Figure 34:
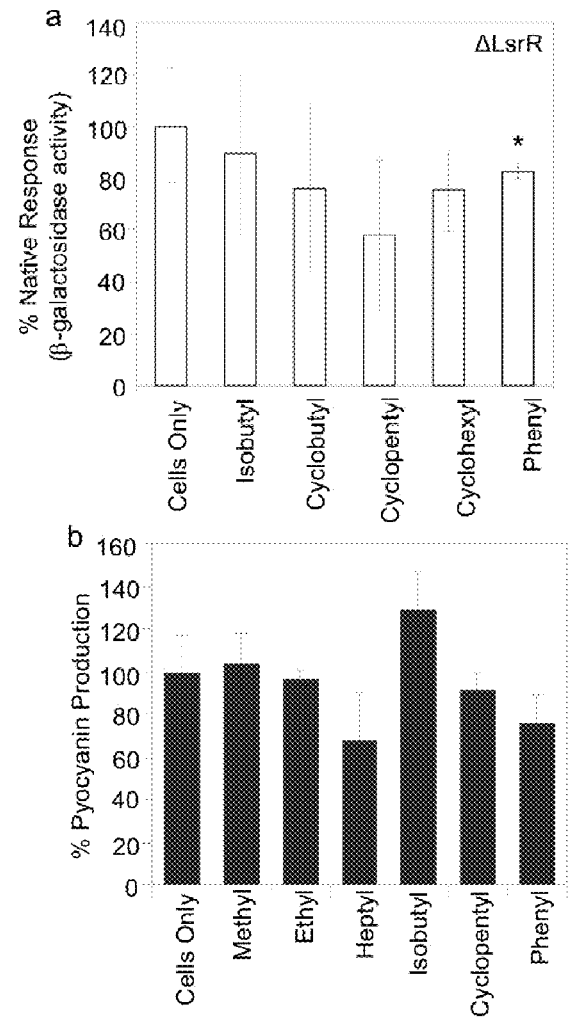
FIG. 34. Effects of analogs on (a) *E. coli* via LsrR, and (b) *P. aeruginosa* via production of pyocyanin. a) AI-2 dependent β-galactosidase production in *E. coli* ZK126 pLW11 LW8 (luxS+, lsrR−) in response to 20μ) analog. b) Effect of analogs (100 μM) on pyocyanin production in *P. aeruginosa* PAO1 (* indicates p<0.05 for an unpaired t test of the particular analog compared to the cells only response).

To test whether the phosphorylated analogs work through repressor LsrR, studies were carried out in isogenic lsrR null mutants. We showed in other Examples that DPD analogs did not alter lsr expression in the absence of LsrR, which is the transcriptional repressor of the circuit. In this Example the results are similar, while there was more variability, there was no statistically significant difference between the analogs and the control, with the exception of the aromatic phenyl-DPD (FIG. 34, panel a). Thus, we demonstrate that AI-2 analogs that act as antagonists do so via LsrR, which in part led to our discovery that that it is the phosphorylated analogs and LsrR that combine to achieve inhibition, which permits the use of phosphomimics of AI-2 as antagonists according to the invention.

TABLE 5

Inhibitory Concentrations (IC$_{50}$) of select analogs*

| Analog | IC$_{50}$ of analog (nM) to inhibit QS in *E. coli* | Standard Error (logIC$_{50}$) *E. coli* | IC$_{50}$ of analog (nM) to inhibit QS in *S. typhimurium* | Standard Error (logIC$_{50}$) *S. typhimurium* |
|---|---|---|---|---|
| Isobutyl-DPD | 54 | 181 | 20000 | 116 |
| Butyl-DPD | 2967 | 193 | >40000 | ND |
| Cyclopentyl-DPD | 2443 | 146 | >40000 | ND |
| Heptyl-DPD | 15940 | 244 | >40000 | ND |
| Phenyl-DPD | >40000 | ND | >40000 | ND |

*IC$_{50}$ values reflect the concentration of analogs required to reduce lsr expression (β-galactosidase production) to 50% in the presence of 20 μM exogenously added synthetic DPD. β-galactosidase production in the absence of analog (only 20 μM DPD) was set as the 100% response.

Figure 3:
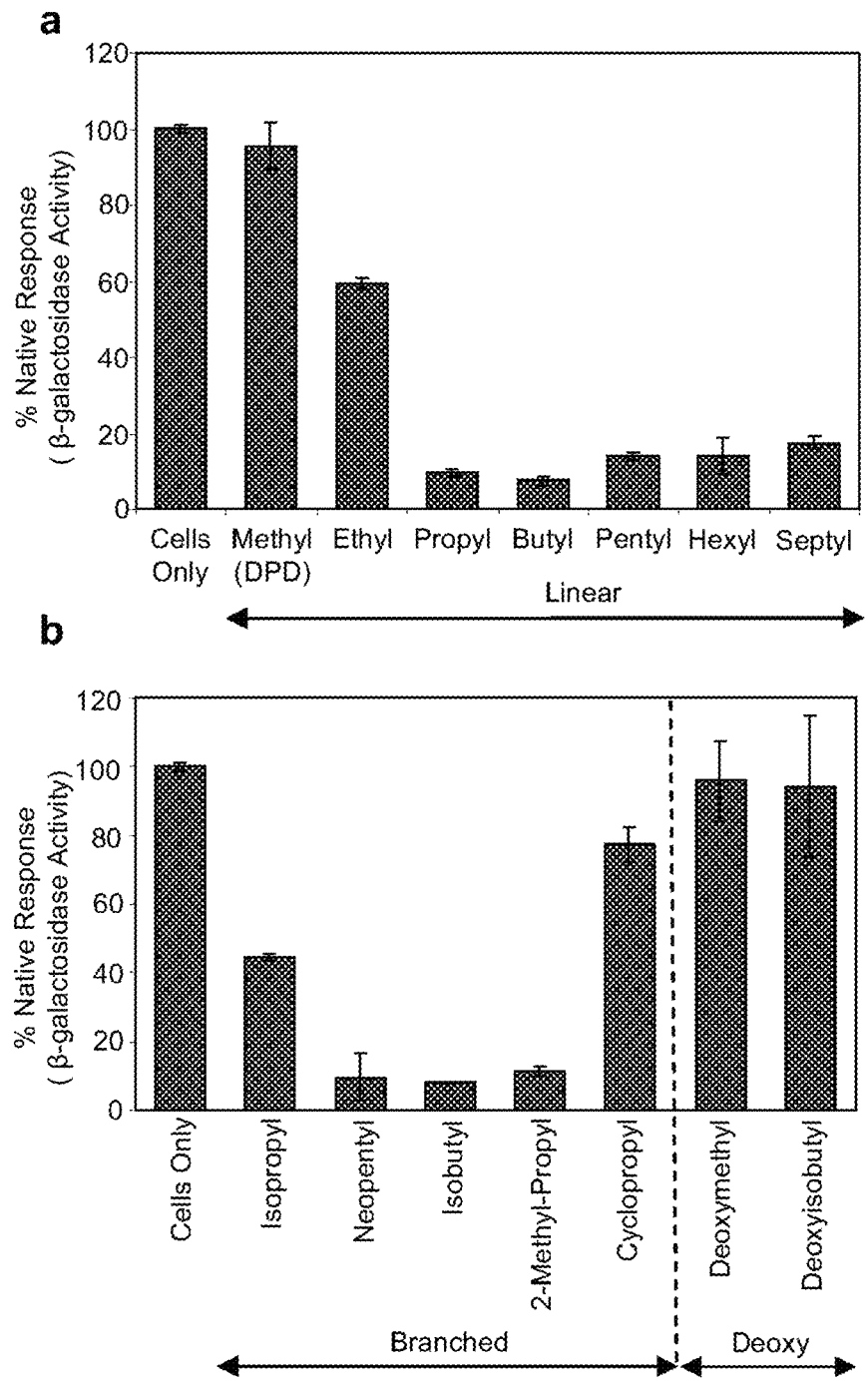
FIG. 3. DPD Analogs inhibit native signaling in E. coli in the absence of the AI-2 transporter but only in the presence of the QS lsr-circuit repressor LsrR AI-2 dependent β-galactosidase production in E. coli LW9 pLW11 (luxS+) in response to (a) linear analogs, and (b) branched and deoxy-DPD analogs.
Figure 38:
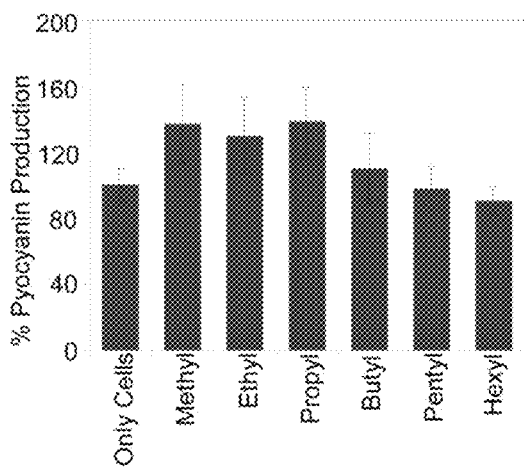
FIG. 38. Effect of linear analogs on pyocyanin production in *P. aeruginosa* PAO1.
Figure 39:
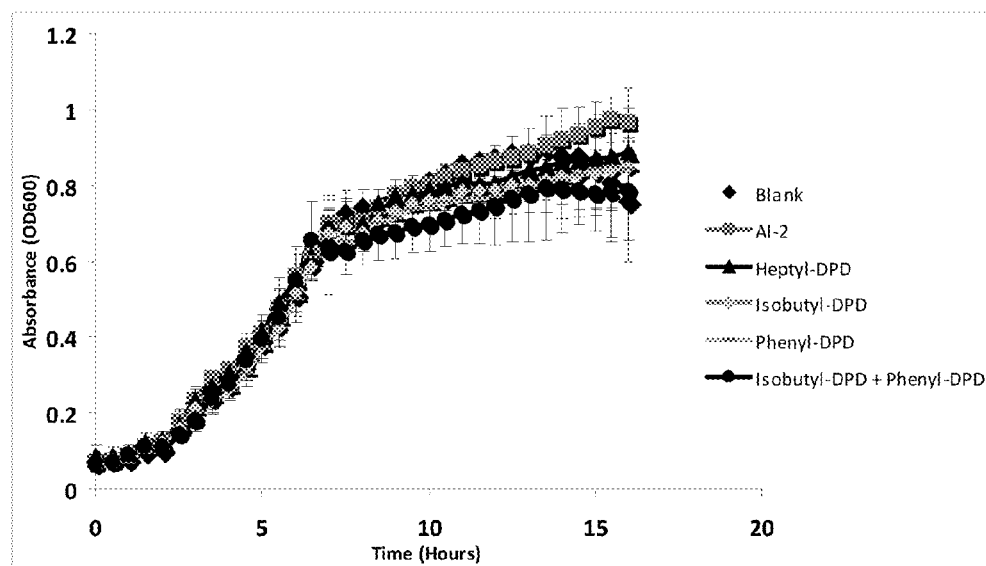
FIG. 39. Growth curve of *P. aeruginosa* PAO1 (over time) in the presence (or absence) of AI-2 and analogs (and cocktails).
Figure 40:
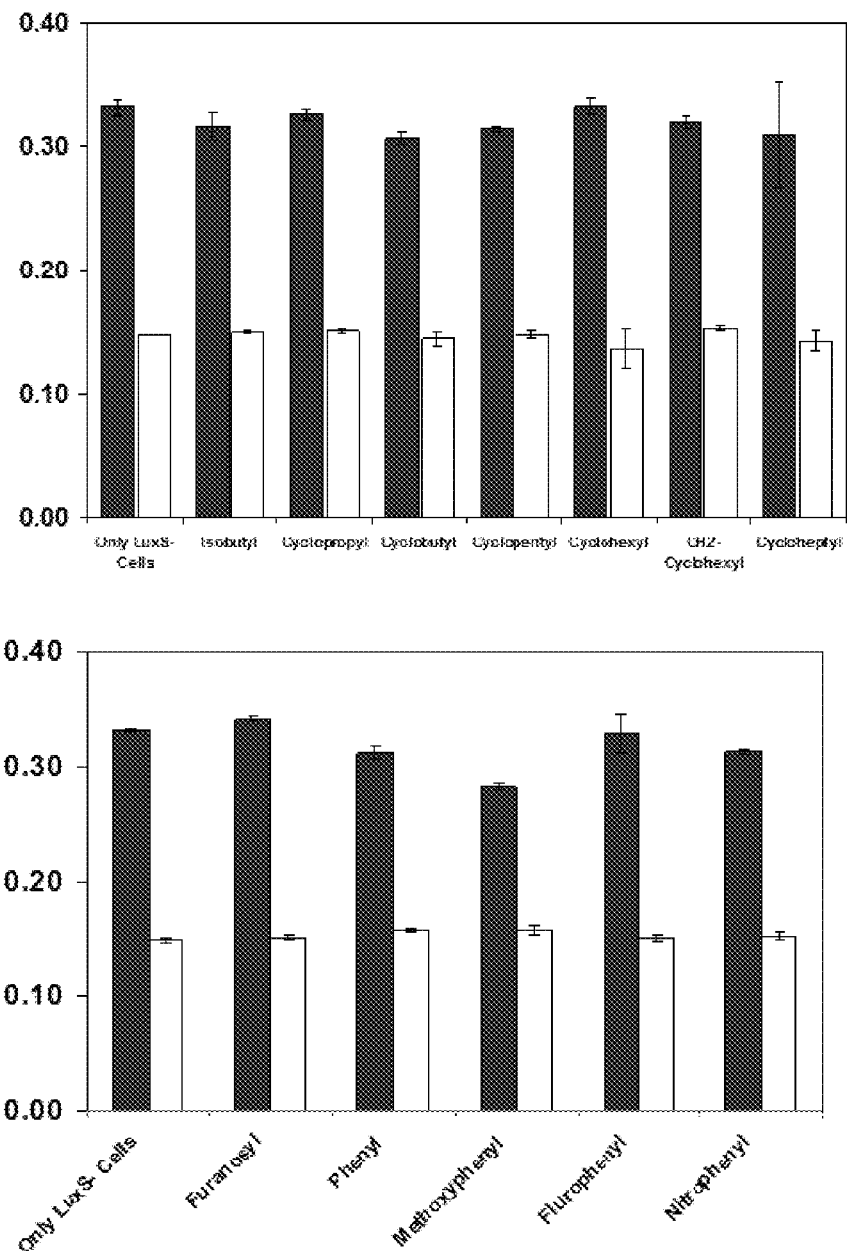
FIG. 40. Effect of cyclic and aromatic analogs on growth (final OD 600) of *E. coli* and *S. typhimurium*. (top) cyclic analogs (bottom) aromatic analogs.
Figure 41:
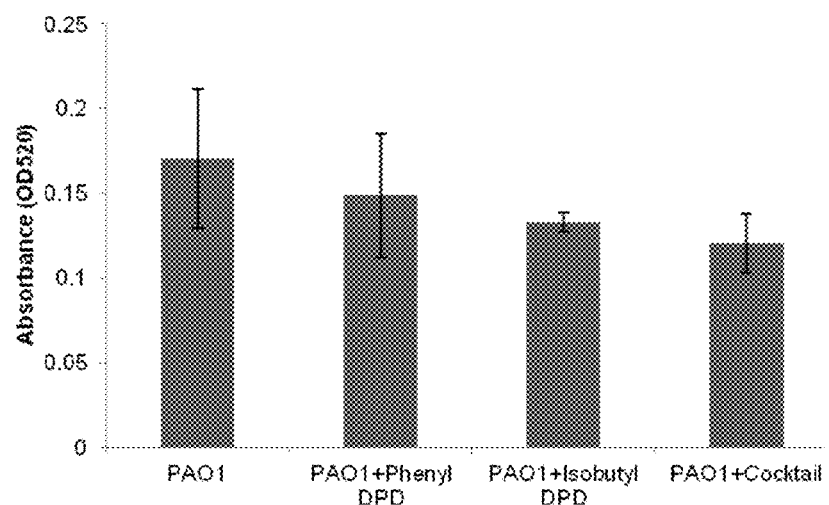
FIG. 41. Effect of phenyl-DPD, isobutyl-DPD and a cocktail (phenyl-DPD and isobutyl-DPD) on pyocyanin production in pure culture *P. aeruginosa*.
Figure 42:
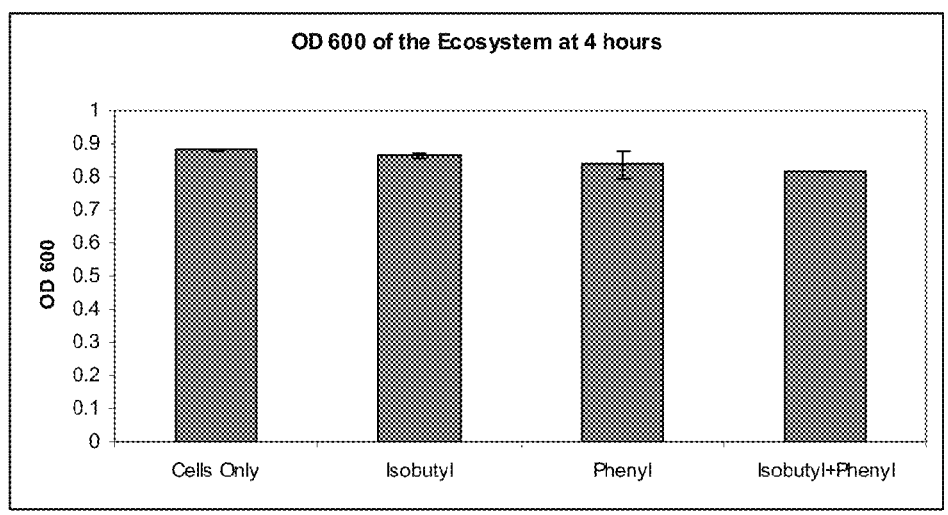
FIG. 42. OD600 of synthetic ecosystem in the presence of isobutyl-DPD, phenyl-DPD and the cocktail (isobutyl-DPD and phenyl-DPD).
Figure 43:
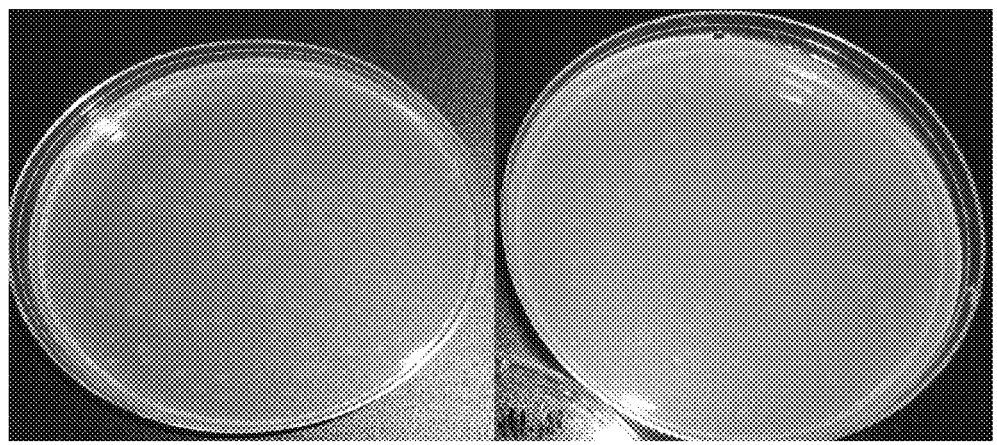
FIG. 43. CFU determination of *P. aeruginosa* grown alone and in the synthetic ecosystem. a) (left) Control (PAO1 alone): 7.3 E+07 CFU/ml and b) (right) PAO1/MET 708/W3110PCT6: 6.5 E+07 CFU/ml.

Identifying Modulators of *P. aeruginosa* QS. DPD analogs (100 μM) were screened for activity in *P. aeruginosa* PAO1 by monitoring pyocyanin production (FIG. 34b and FIG. 38). Pyocyanin is a redox active phenazine toxin produced by *P. aeruginosa* and has been shown to have antibiotic properties as well as being a signal for the up-regulation of QS-controlled genes in the stationary phase. Phenyl- and heptyl-DPD showed some inhibition of pyocyanin production (FIG. 34b and FIG. 3).

Figure 35:
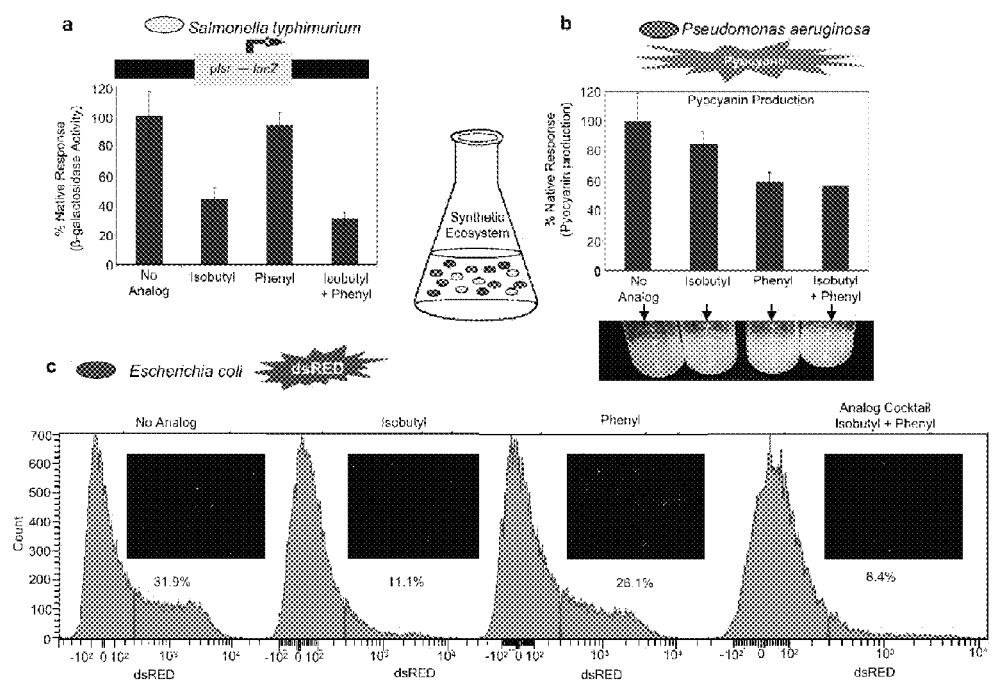
FIG. 35. Effect of analog and analog cocktail in a trispecies synthetic ecosystem. a) AI-2 dependent β-galactosidase production in *S. typhimurium* MET708 (normalized to native *S. typhimurium* response in trispecies culture=475 Miller units) b) QS related pyocyanin production in *P. aeruginosa* PAO1 (normalized to native *P. aeruginosa* response in trispecies culture=2.5 μg/mL) c) AI-2 dependent dsRED induction in *E. coli* W3110 pCT6 dsRED, in response to isobutyl-DPD (40 μM) and phenyl-DPD (40 μM) individually and a cocktail of both the analogs. Note, in this entire system, no exogenous AI-2 was added. Instead, the enteric bacteria present in the ecosystem synthesized the AI-2 signal present.

Effect of analogs in a tri-species synthetic ecosystem. The results suggesting species specific modulation of QS activity lead to the testing of effects in mixed cell cultures. Isobutyl-DPD (40 μM) and phenyl-DPD (40 μM) were added to a tri-species synthetic ecosystem created by culturing *E. coli*, *S. typhimurium* and *P. aeruginosa* in the same tubes. In order to differentiate and monitor the QS response from each organism, different and orthogonal reporter strains were used; in *E. coli*, AI-2 mediated dsRED expression, in *S. typhimurium*, AI-2 mediated β-galactosidase production; and in *P. aeruginosa* effects of AI-2 were examined for pyocyanin production. Isobutyl-DPD inhibited *E. coli* and *S. typhimurium* simultaneously, but due to its lack of inhibitory effects in *P. aeruginosa*, it was suspected that it would not serve well as a broad-spectrum quorum silencer in the tri-species synthetic ecosystem. Interestingly, it did inhibit all three species, but *P. aeruginosa* to a lesser extent (FIG. 35). Phenyl-DPD, on the other hand, was largely ineffective as a QS inhibitor for *E. coli* and *S. typhimurium* but retained some activity against pyocyanin production in *P. aeruginosa*.

The effect of each analog as a quorum quencher was undisturbed by the presence of the other analog. A conclusion can be drawn, therefore, that a cocktail of DPD analogs consisting of isobutyl- and phenyl-DPD analogs could simultaneously disrupt QS signaling in the three different bacteria simultaneously via a non-toxic mechanism (FIGS. 39, 40, 42 and 43).

In this Example, a set of C1 analogs that enhances understanding of the shapes and sizes of C1 substituted groups that are tolerated by AI-2 processing enzymes, such as LsrK, was developed. C1 alkyl chains needed at least 3-carbon length for lsr inhibition in *E. coli*; the shape as well as the conformational flexibility of the C1 side chain is also important. For cyclic compounds there was an apparent 5-carbon maximum where analogs larger than cyclopentyl-DPD (i.e. cyclohexyl, CH$_2$-cyclohexyl, cycloheptyl) were not phosphorylated by LsrK and were less effective on LsrR. IC$_{50}$ data (Table 5) shows that analogs that are not readily phosphorylated require higher concentrations in order to obtain 50% lsr repression. In *P. aeruginosa*, where the phosphorylation pathway is not involved, phenyl-DPD inhibited QS related pyocyanin production via unknown mechanisms. The inability of phenyl-DPD to completely inhibit pyocyanin production is probably due to the fact that other pathways, such as the AI-1 pathway, also control pyocyanin production.

Figure 36:
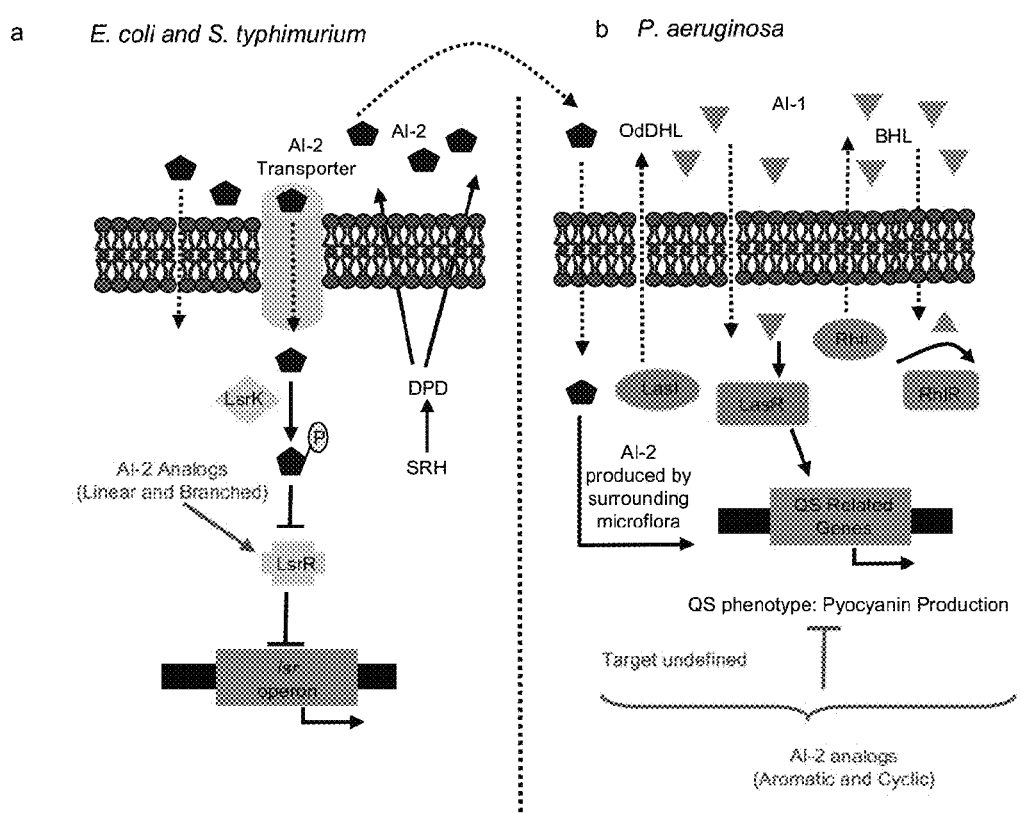
FIG. 36. Quorum Sensing Pathways in *E. coli*, *S. typhimurium* and *P. aeruginosa* and AI-2 Analog Points of Action (a) AI-2 based QS signaling circuit in *E. coli* and *S. typhimurium*; effective analogs are phosphorylated by LsrK and work via alteringrepressor LsrR activity. b) The two AI-1 based LuxI/LuxR QS signaling circuits in *P. aeruginosa*; LasI/R and RhlI/R that produce different AHL autoinducers, N-(3-oxododecanoyl)-HSL (OdDHL) and N-butyryl-HSL (BHL) respectively to control QS associated virulence factors. There remain no identified effectors modulated by AI-2 or analogs, just phenomenological observation.
Figure 37:
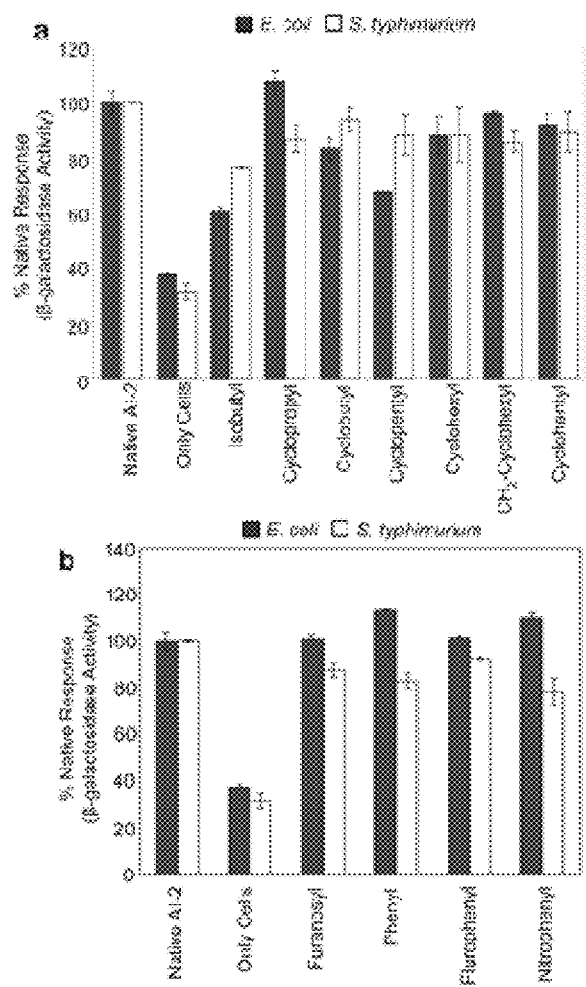
FIG. 37. Effect of analogs on native signaling in *E. coli* and *S. typhimurium* AI-2 dependent β-galactosidase production in *E. coli* ZK126 pLW11 and *S. typhimurium* MET708 both (luxS+) in response to a) cyclic b) aromatic (100% Native *E. coli* (ZK126) response=597 Miller units and 100% native *S. typhimurium* (MET708) response=4776 Miller units).

Exogenous AI-2 can up-regulate genes important for *P. aeruginosa* pathogenesis. *P. aeruginosa* utilizes the AI-1 controlled LuxI/LuxR QS signaling circuit (FIG. 36, panel b) but because they are often found among other Gram negative microbes capable of synthesizing AI-2, *P. aeruginosa* likely detects their AI-2 to coordinate the expression of pathogenic genes during infection. This Example indicates that AI-2 analogs, such as phenyl-DPD, could be *P. aeruginosa* antitoxin inhibitors. Interestingly, some evidence that the effects of phenyl-DPD were greater against *P. aeruginosa* when cultivated in the mixed culture were found. Noted was that *V. harveyi* QS signaling was dramatically attenuated when in a mixed culture with *E. coli*.

The following materials and methods were used to obtain the data presented in this Example.

Bacterial Strains and Growth Conditions (Table 4) lists the bacterial strains and plasmids used in this study. *S. typhimurium* and *E. coli* strains were cultured in Luria-Bertani medium (LB, Sigma) at 37° C. with shaking at (250 rpm) unless otherwise noted. Antibiotics were used for the following strains: (60 or 100 µg/mL) kanamycin for *S. typhimurium* MET715, *S. typhimurium* MET708 and (60 or 100 µg/mL) ampicillin for *E. coli* LW7 pLW11, (50 µg/mL) ampicillin and (50 µg/mL) kanamycin for *E. coli* W3110 pCT6 dsRED.

Measurement of the QS Response (lsr Expression)

The QS response indicated by lsr gene expression was analyzed in pure culture studies by culturing *E. coli* LW7 pLW11, *E. coli* ZK126 pLW11 and *S. typhimurium* MET708, *S. typhimurium* MET715 overnight in LB medium individually supplemented with appropriate antibiotics, as specified above. These cells were diluted into fresh LB medium (with antibiotics) and grown to an $OD_{600}$ of 0.8-1.0 at 30° C., 250 rpm. Cells were collected by centrifugation at 10,000×g for 10 minutes, and resuspended in 10 mM phosphate buffer. AI-2 (20 µM) and the respective analog (20 µM) were added to the *E. coli* or *S. typhimurium* suspension for 2 hours at 37° C. AI-2 dependent β-galactosidase production was quantified by the Miller assay.

In Vitro Phosphorylation of Analogs

LsrK was purified from *E. coli* BL21 pET200-LsrK as described before. Phosphorylated analogs were synthesized by incubating (1 µM) LsrK with (40 µM) ATP (Roche), (0.2 Ci) of [$P^{32}$] ATP (Perkin-Elmer), (300 µM) AI-2 or analog, (200 µM) $MgCl_2$, in (25 mM) phosphate buffer, pH 7.4 for 2 hours. An aliquot (2.5 µL) was then spotted onto a cellulose TLC plate (Selecto Scientific). The plate was developed using 0.8 M LiCl as the solvent, air dried and developed via autoradiography.

Measurement of the QS Response (Pyocyanin Production)

The cells were grown with the analog at 3 mL total volume in 50 mL flasks in LB medium, with continuous shaking. Between 22-24 h, when the cells turned green after pyocyanin secretion, the pigment was extracted. The pyocyanin quantification assay was conducted as described. 2 mL chloroform was added to the 3 mL culture and pipetted up and down. 1 mL of the chloroform was transferred to a separate tube and the pyocyanin was re-extracted into 200 µL of 0.2 M HCl. The absorbance of the solution was measured at OD 520 nm. To calculate the concentration of pyocyanin extracted as µg/mL, the OD at 520 nm was multiplied by 17.07.

Analyzing QS Response in the Synthetic Ecosystem

*S. typhimurium* MET708, *P. aeruginosa* PAO1 and *E. coli* W3110 pCT6 dsRED were each cultured separately overnight in LB medium supplemented with the appropriate antibiotic. *P. aeruginosa* PAO1, *S. typhimurium* MET708 and *E. coli* W3110 pCT6 dsRED were diluted (25 µL:2.5 µL:100 µL) of the overnight culture respectively, into a single 2 mL final volume of fresh LB medium without antibiotics. The co-culture was supplemented with (40 µM) of the respective analog or analog cocktail initially and again after 2.5, 5, 9 and 18 h of growth. The *S. typhimurium* lacZ (β-galactosidase) activity was measured after 4 h. The *E. coli* response was determined after 24 h, by fixing the cells with 1:1 cold 4% paraformaldehyde and using flow cytometric analysis. Samples were analyzed by flow cytometry (FACS Canto II, BD 394 Biosciences), with 30,000 gated events analyzed per sample. Pyocyanin was also extracted after 24 h of growth.

EXAMPLE 7

Procedure for *P. aeruginosa* CFU Determination:

*S. typhimurium* MET708, *P. aeruginosa* PAO1 and *E. coli* W3110 pCT6 dsRED were each cultured separately overnight in LB medium supplemented with the appropriate antibiotic (kanamycin (60 µg/ml) for *S. typhimurium* MET 708, and ampicillin (50 µg/ml) for *E. coli* W3110 pCT6 dsRED). *P. aeruginosa* PAO1, *S. typhimurium* MET708 and *E. coli* W3110 pCT6 dsRED were diluted (25 µl:2.5 µl:100 µl) of the overnight culture respectively, into a single 2 ml final volume of fresh LB medium without antibiotics. The control, PAO1 (25 µl) was also diluted in 2 ml LB. After 3 hours of incubation, the cultures were diluted up to 1 in 100000 and 10 µl of inoculum was plated on Cetrimide agar. Plates used for CFU determination represent 1:10000 dilution.

DPD Analogs were Prepared as Followed:

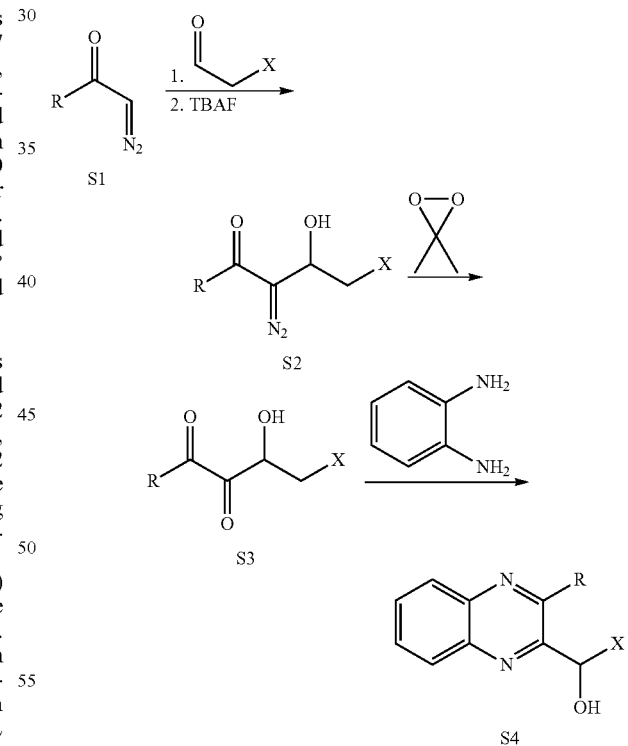

NMR Characterization

NMR spectra were measured on Bruker AV-400, Bruker DRX-400 ($^1$H at 400 MHz, $^{13}$C at 100 MHz), Bruker DRX-500 ($^1$H at 500 MHz, $^{13}$C at 125 MHz) or Bruker AVIII-600 ($^1$H at 600 MHz, $^{13}$C at 150 MHz). Data for $^1$H-NMR spectra are reported as follows: chemical shift (ppm, relative to residual solvent peaks or indicated external standards; s=singlet, d=doublet, t=triplet, q=quartet, dd=doublet of doublets, td=triplet of doublets, m=multiplet), coupling constant (Hz), and integration. Data for $^{13}$C-NMR are reported in terms of chemical shift (ppm) relative to residual solvent peak. Mass spectra (MS) and high resolution mass spectra (HRMS) were recorded by JEOL AccuTOF-CS (ESI positive, needle voltage 1800~2400 eV). Infrared spectra (IR) were recorded by a ThermoNicolet IR200 Spectrometer.

DPD analogs exist as mixture of isomers and it is a practice in the field to make quinoxaline derivatives of DPD analogs, which are single compounds, and characterized to provide final proof of analog identity. Therefore, all new DPD analogs were converted into their respective quinoxaline derivatives and characterized.

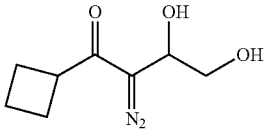

1-cyclobutyl-2-diazo-3,4-dihydroxybutan-1-one $^1$H NMR (400 MHz, CDCl$_3$) δ ppm=4.72 (1H, s), 4.64 (1H, s), 4.13-3.90 (1H, m), 3.81-3.71 (1H, m), 3.71-3.60 (1H, m), 3.49-3.36 (1H, m), 2.38-2.21 (2H, m), 2.18-2.05 (2H, m), 2.04-1.90 (1H, m), 1.90-1.77 (1H, m). $^{13}$C NMR (100 MHz, CDCl$_3$) δ ppm=196.7, 69.1, 66.2, 64.8, 42.4, 24.9, 18.3.

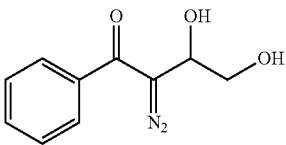

2-diazo-3,4-dihydroxy-1-phenylbutan-1-one $^1$H NMR (400 MHz, d$_4$-MeOD) δ ppm=7.66 (2H, d, J=7.1 Hz), 7.61-7.55 (1H, m), 7.55-7.48 (2H, m), 4.84 (1H, br s), 3.83-3.70 (2H, m). $^{13}$C NMR (100 MHz, d$_4$-MeOD) δ ppm=190.1, 138.1, 131.8, 128.8, 127.2, 66.5, 64.1.

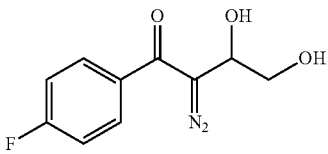

2-diazo-1-(4-fluorophenyl)-3,4-dihydroxybutan-1-one $^1$H NMR (400 MHz, CDCl$_3$) δ ppm=7.69-7.59 (2H, m), 7.18-7.07 (2H, m), 4.99-4.91 (1H, m), 4.13 (1H, br s), 3.98-3.90 (1H, m), 3.89-3.80 (1H, m), 3.28 (1H, br s). $^{13}$C NMR (100 MHz, CDCl$_3$) δ ppm=188.6, 166.4, 163.9, 133.6, 130.2, 116.5, 67.3, 64.8.

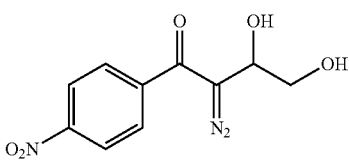

2-diazo-3,4-dihydroxy-1-(4-nitrophenyl)butan-1-one $^1$H NMR (400 MHz, d$_4$-MeOD) δ ppm=8.37 (2H, d, J=8.7 Hz), 7.89 (2H, d, J=8.7 Hz), 4.89-4.71 (1H, m), 3.82-3.71 (2H, m). $^{13}$C NMR (100 MHz, d$_4$-MeOD) δ ppm=149.8, 143.5, 128.6, 124.0, 66.0, 64.0.

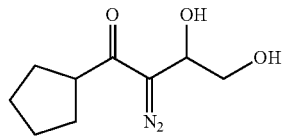

1-cyclopentyl-2-diazo-3,4-dihydroxybutan-1-one $^1$H NMR (400 MHz, CDCl$_3$) δ ppm=4.80-4.70 (1H, m), 4.69-4.61 (1H, m), 4.06 (1H, br s), 3.82-3.70 (1H, m), 3.70-3.58 (1H, m), 3.06-2.93 (1H, m), 1.86-1.72 (4H, m), 1.71-1.61 (2H, m), 1.61-1.50 (2H, m). $^{13}$C NMR (100 MHz, CDCl$_3$) δ ppm=197.9, 69.6, 65.8, 64.4, 46.7, 29.5, 26.1.

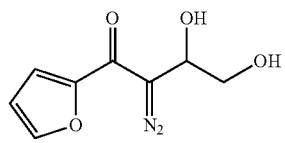

2-diazo-1-(furan-2-yl)-3,4-dihydroxybutan-1-one $^1$H NMR (400 MHz, d$_4$-MeOD) δ ppm=7.75-7.69 (1H, m), 7.23-7.17 (1H, m), 6.68-6.64 (1H, m), 4.97-4.91 (1H, m), 3.77-3.70 (2H, m). $^{13}$C NMR (100 MHz, d$_4$-MeOD) δ ppm=152.6, 145.4, 116.1, 112.3, 65.8, 64.0.

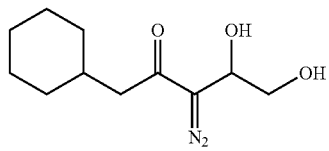

1-cyclohexyl-3-diazo-4,5-dihydroxypentan-2-one $^1$H NMR (400 MHz, CDCl$_3$) δ ppm=4.87-4.67 (1H, m), 4.31 (1H, br s), 3.87-3.75 (1H, m), 3.75-3.65 (1H, m), 3.61 (1H, br s), 2.34 (2H, d, J=6.9 Hz), 1.89-1.76 (1H, m), 1.76-1.59 (5H, m), 1.34-1.20 (2H, m), 1.20-1.07 (1H, m), 1.05-0.87 (2H, m). $^{13}$C NMR (100 MHz, CDCl$_3$) δ ppm=195.0, 71.5, 66.4, 64.8, 46.3, 35.7, 33.5, 26.5, 26.4.

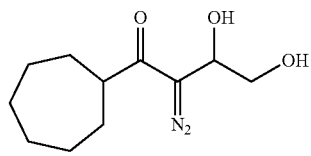

1-cycloheptyl-2-diazo-3,4-dihydroxybutan-1-one $^1$H NMR (400 MHz, CDCl$_3$) δ ppm=4.81-4.71 (1H, m), 4.06-3.86 (1H, br s), 3.86-3.78 (1H, m), 3.77-3.68 (1H, m), 3.19 (1H, br s), 2.75-2.64 (1H, m), 1.87-1.73 (4H, m), 1.73-1.63 (2H, m), 1.63-1.52 (4H, m), 1.52-1.41 (2H, m). $^{13}$C NMR (100 MHz, CDCl$_3$) δ ppm=199.9, 68.6, 66.8, 64.8, 48.1, 31.0, 28.5, 27.0.

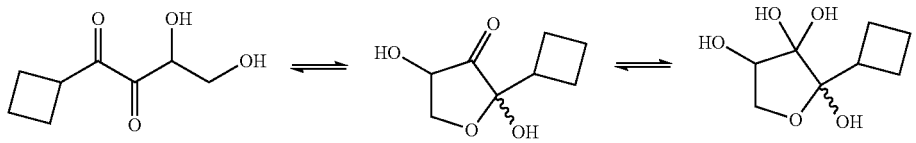 [SMILES: O=C(C(=O)C1CCC1)C(O)CO ; O=C1C(O)COC1(O)C1CCC1 ; OC1COC(O)(C2CCC2)C1(O)O]

Equilibrium Mixture of Cyclobutyl DPD $^1$H NMR (400 MHz, D$_2$O) δ ppm=4.66-4.39 (m), 4.27-3.98 (m), 3.96-3.46 (m), 2.92-2.59 (m), 2.24-1.55 (m). $^{13}$C NMR (100 MHz, D$_2$O) δ ppm=212.9, 104.8, 100.2, 97.24, 74.6, 74.0, 70.6, 69.1, 67.1, 61.5, 40.6, 38.1, 38.0, 25.7, 25.5, 23.1, 22.9, 22.6, 22.5, 17.8, 17.7.

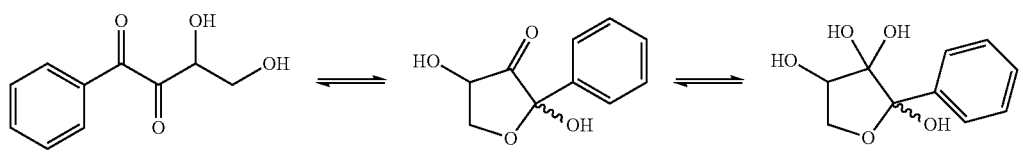 [SMILES: O=C(C(=O)C(O)CO)c1ccccc1 ; O=C1C(O)COC1(O)c1ccccc1 ; OC1COC(O)(c2ccccc2)C1(O)O]

Equilibrium Mixture of Phenyl DPD $^1$H NMR (400 MHz, D$_2$O) δ ppm=8.19-8.05 (m), 7.94-7.83 (m), 7.75-7.20 (m), 4.56-4.45 (m), 4.44-4.26 (m), 4.16-3.54 (m). $^{13}$C NMR (100 MHz, D$_2$O) δ ppm=138.2, 137.8, 136.3, 134.5, 130.4, 129.6, 129.4, 129.1, 128.5, 128.4, 127.4, 127.3, 104.3, 104.1, 100.5, 99.7, 75.8, 75.1, 74.6, 73.8, 71.8, 69.2, 62.5, 61.6.

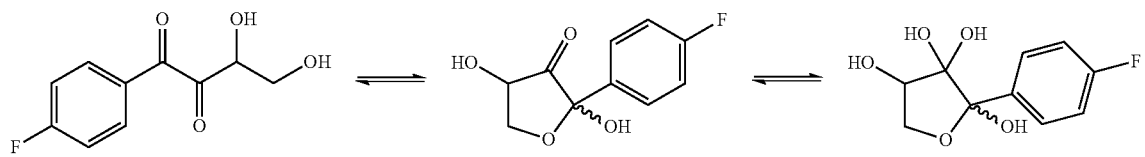 [SMILES: O=C(C(=O)C(O)CO)c1ccc(F)cc1 ; O=C1C(O)COC1(O)c1ccc(F)cc1 ; OC1COC(O)(c2ccc(F)cc2)C1(O)O]

Equilibrium Mixture of 4-fluorophenyl DPD $^1$H NMR (400 MHz, D$_2$O) δ ppm=8.31-8.10 (m), 8.10-7.88 (m), 7.63-7.32 (m), 7.31-6.89 (m), 4.52-4.15 (m), 4.15-3.54 (m). $^{13}$C NMR (100 MHz, D$_2$O) δ ppm=198.7, 164.6, 162.2, 133.8, 133.7, 133.6, 129.5, 129.4, 115.2, 115.1, 115.0, 104.0, 103.8, 100.4, 99.5, 97.5, 75.7, 75.1, 74.6, 73.7, 71.9, 69.2, 62.5, 61.6.

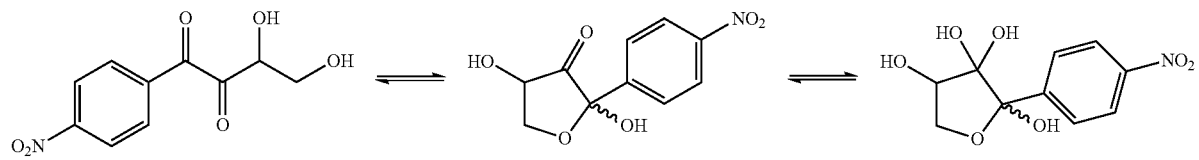

Equilibrium Mixture of 4-nitrophenyl DPD $^1$H NMR (400 MHz, D$_2$O) δ ppm=8.39-8.11 (m), 8.02-7.67 (m), 4.55-4.28 (m), 4.20-3.98 (m), 3.85-3.75 (m). $^{13}$C NMR (100 MHz, D$_2$O) δ ppm=215.9, 148.4, 145.9, 128.7, 123.6, 103.5, 100.7, 99.9, 74.7, 73.8, 72.2, 69.6, 30.6.

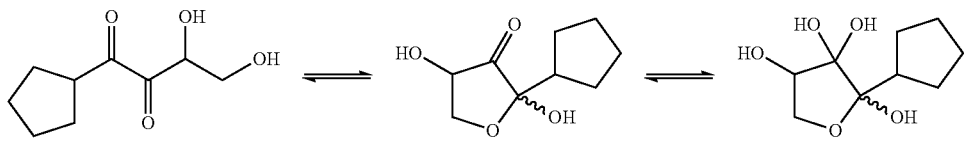 [SMILES: O=C(C(=O)C1CCCC1)C(O)CO ; O=C1C(O)COC1(O)C1CCCC1 ; OC1COC(O)(C2CCCC2)C1(O)O]

Equilibrium Mixture of Cyclopentyl DPD $^1$H NMR (400 MHz, D$_2$O) δ ppm=4.60-4.29 (m), 4.12-3.27 (m), 2.35-2.11 (m), 1.89-1.22 (m). $^{13}$C NMR (100 MHz, D$_2$O) δ ppm=216.4, 214.8, 204.3, 200.4, 105.8, 100.5, 100.3, 97.2, 75.1, 74.6, 74.0, 73.8, 71.6, 70.8, 68.7, 66.8, 63.0, 61.6, 45.5, 45.4, 44.7, 43.6, 42.7, 42.5, 31.9, 31.6, 28.7, 28.2, 26.7, 26.6, 26.5, 26.3, 26.1, 26.0, 25.9, 25.8, 25.7, 25.6, 25.3.

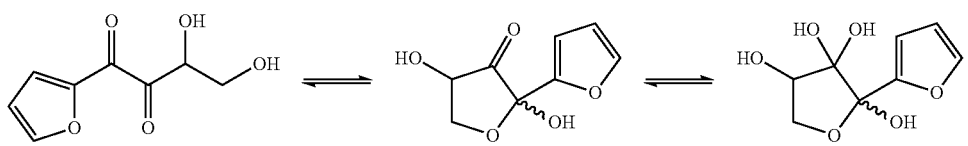 [SMILES: O=C(C(=O)C(O)CO)c1ccco1 ; O=C1C(O)COC1(O)c1ccco1 ; OC1COC(O)(c2ccco2)C1(O)O]

Equilibrium Mixture of Furanyl DPD $^1$H NMR (400 MHz, D$_2$O) δ ppm=7.89-7.76 (m), 7.75-7.62 (m), 6.72-6.57 (m), 6.33-6.03 (m), 4.54-4.18 (m), 4.18-3.40 (m). $^{13}$C NMR (100 MHz, D$_2$O) δ ppm=188.1, 150.0, 149.4, 125.3, 113.4, 97.2, 75.6, 61.5, 30.6.

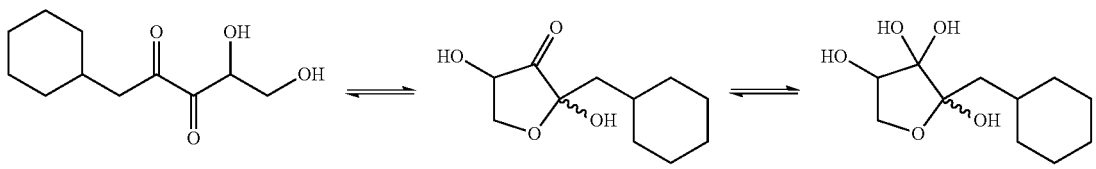 [SMILES: O=C(CC1CCCCC1)C(=O)C(O)CO ; O=C1C(O)COC1(O)CC1CCCCC1 ; OC1COC(O)(CC2CCCCC2)C1(O)O]

Equilibrium Mixture of Cyclohexyl DPD $^1$H NMR (400 MHz, D$_2$O) δ ppm=3.89-3.78 (m), 3.76-3.62 (m), 3.60-3.47 (m), 2.68-2.45 (m), 1.83-1.35 (m), 1.24-1.01 (m), 0.99-0.82 (m). $^{13}$C NMR (100 MHz, D$_2$O) δ ppm=211.9, 96.8, 74.0, 61.6, 44.4, 33.1, 32.9, 30.7, 26.2, 26.0.

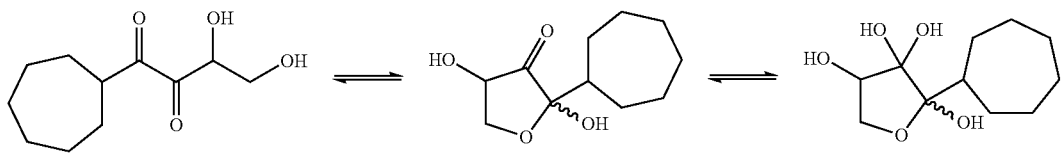 [SMILES: O=C(C(=O)C1CCCCCC1)C(O)CO ; O=C1C(O)COC1(O)C1CCCCCC1 ; OC1COC(O)(C2CCCCCC2)C1(O)O]

Equilibrium Mixture of Cycloheptyl DPD $^1$H NMR (400 MHz, D$_2$O) δ ppm=4.55-4.45 (m), 4.45-4.35 (m), 3.90-3.64 (m), 3.59-3.42 (m), 1.97-1.13 (m). $^{13}$C NMR (100 MHz, D$_2$O) δ ppm=216.9, 97.4, 74.0, 71.6, 68.3, 66.9, 66.5, 61.7, 46.0, 44.6, 41.6, 31.5, 31.0, 29.7, 29.0, 28.0, 26.9, 14.5.

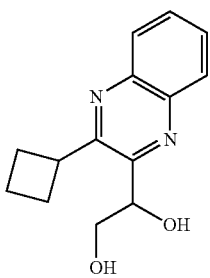 [SMILES: OCC(O)c1nc2ccccc2nc1C1CCC1]

1-(3-cyclobutylquinoxalin-2-yl)ethane-1,2-diol $^1$H NMR (400 MHz, CDCl$_3$) δ ppm=8.14 (1H, dd, J=8.0, 1.4 Hz), 8.04 (1H, dd, J=8.0, 1.4 Hz), 7.82-7.70 (2H, m), 5.18-5.06 (1H, m), 4.63 (1H, br s), 4.08-3.94 (1H, m), 3.79-3.69 (1H, m), 2.86 (1H, br s), 2.75-2.57 (2H, m), 2.50-2.34 (2H, m), 2.25-2.10 (1H, m), 2.08-1.97 (1H, m). $^{13}$C NMR (100 MHz, CDCl$_3$) δ ppm=157.2, 152.5, 142.5, 139.6, 130.2, 129.8, 129.4, 128.6, 71.0, 67.1, 38.4, 27.9, 18.5. HRMS (ESI$^+$) m/z calcd. for C$_{14}$H$_{17}$N$_2$O$_2$ [M+H]$^+$ 245.1290. found 245.1294.

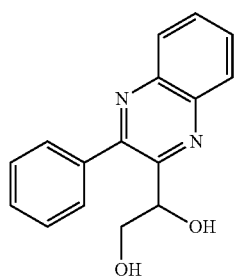 [SMILES: OCC(O)c1nc2ccccc2nc1-c1ccccc1]

1-(3-phenyl-quinoxalin-2-yl)-ethane-1,2-diol $^1$H NMR (400 MHz, CDCl$_3$) δ ppm=8.25-8.17 (1H, m), 8.17-8.09 (1H, m), 7.88-7.78 (2H, m), 7.75-7.65 (2H, m), 7.62-7.50 (3H, m), 5.36-5.25 (1H, m), 4.70 (1H, br s), 3.82-3.70 (1H, m), 3.62-3.51 (1H, m), 2.76 (1H, br s). $^{13}$C NMR (100 MHz, CDCl$_3$) δ ppm=154.1, 153.0, 142.2, 140.0, 138.0, 130.9, 130.8, 130.0, 129.8, 129.4, 129.2, 128.8, 71.0, 66.1. HRMS (ESI$^+$) m/z calcd. for C$_{16}$H$_{15}$N$_2$O$_2$ [M+H]$^+$ 267.1134. found 267.1123.

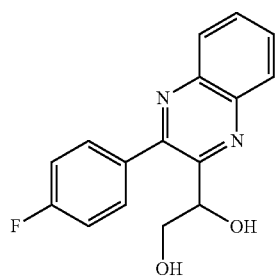 [SMILES: OCC(O)c1nc2ccccc2nc1-c1ccc(F)cc1]

1-(3-fluorophenyl-quinoxalin-2-yl)-ethane-1,2-diol $^1$H NMR (400 MHz, CDCl$_3$) δ ppm=8.25-8.15 (1H, m), 8.15-8.07 (1H, m), 7.91-7.80 (2H, m), 7.79-7.68 (2H, m), 7.34-7.21 (2H, m), 5.31-5.18 (1H, m), 4.60 (1H, br s), 3.85-3.72 (1H, m), 3.70-3.57 (1H, m), 2.83 (1H, br s). $^{13}$C NMR (100 MHz, CDCl$_3$) δ ppm=165.2, 162.7, 153.1, 153.0, 142.0, 140.1, 131.4, 131.3, 131.0, 129.8, 128.8, 116.7, 116.4, 70.9, 66.1. HRMS (ESI$^+$) m/z calcd. for C$_{16}$H$_{14}$FN$_2$O$_2$ [M+H]$^+$ 285.1039. found 285.1019.

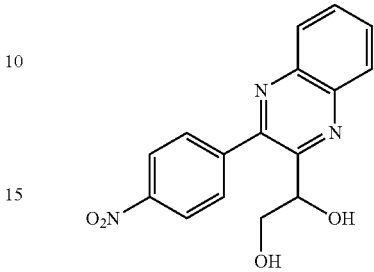

1-(3-nitrophenyl-quinoxalin-2-yl)-ethane-1,2-diol $^1$H NMR (400 MHz, CDCl$_3$) δ ppm=8.44 (2H, d, J=8.6 Hz), 8.27-8.12 (2H, m), 7.99 (2H, d, J=8.6 Hz), 7.95-7.82 (2H, m), 5.24-5.08 (1H, m), 4.43 (1H, br s), 3.87-3.79 (1H, m), 3.79-3.70 (1H, m), 2.97 (1H, br s). $^{13}$C NMR (100 MHz, CDCl$_3$) δ ppm=152.8, 151.9, 148.8, 144.3, 142.1, 140.5, 131.7, 131.5, 130.7, 129.9, 129.0, 124.5, 70.6, 66.2. HRMS (ESI$^+$) m/z calcd. for C$_{16}$H$_{14}$N$_3$O$_4$ [M+H]$^+$ 312.0984. found 312.0962.

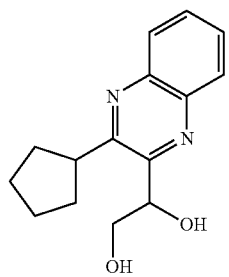 [SMILES: OCC(O)c1nc2ccccc2nc1C1CCCC1]

1-(3-cyclopentylquinoxalin-2-yl)ethane-1,2-diol $^1$H NMR (400 MHz, CDCl$_3$) δ ppm=8.14-7.98 (2H, m), 7.83-7.66 (2H, m), 5.31-5.19 (1H, m), 4.73 (1H, br s), 4.13-3.98 (1H, m), 3.85-3.71 (1H, m), 3.61-3.45 (1H, m), 2.92 (1H, br s), 2.25-2.04 (3H, m), 2.04-1.90 (3H, m), 1.84-1.71 (2H, m). $^{13}$C NMR (100 MHz, CDCl$_3$) δ ppm=159.5, 152.5, 142.7, 139.4, 130.2, 129.7, 129.3, 128.6, 71.1, 67.4, 42.9, 34.7, 33.7, 26.7. HRMS (ESI$^+$) m/z calcd. for C$_{15}$H$_{19}$N$_2$O$_2$ [M+H]$^+$ 259.1447. found 259.1461.

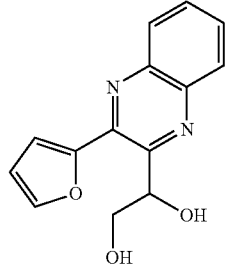 [SMILES: OCC(O)c1nc2ccccc2nc1-c1ccco1]

1-(3-(furan-2-yl)quinoxalin-2-yl)ethane-1,2-diol $^1$H NMR (400 MHz, CDCl$_3$) δ ppm=8.18-8.10 (1H, m), 8.09-8.02 (1H, m), 7.86-7.71 (3H, m), 7.45-7.39 (1H, m), 6.73-6.64 (1H, m), 5.80-5.68 (1H, m), 5.01 (1H, br s), 4.15-4.06 (1H, m), 3.78-3.67 (1H, m), 2.73 (1H, br s). $^{13}$C NMR (100 MHz, CDCl$_3$) δ ppm=152.0, 151.0, 145.4, 142.6, 142.0, 139.4, 131.0, 130.6, 129.5, 128.7, 114.6, 113.0, 71.7, 66.9. HRMS (ESI$^+$) m/z calcd. for C$_{14}$H$_{13}$N$_2$O$_3$ [M+H]$^+$ 257.0926. found 257.0929.

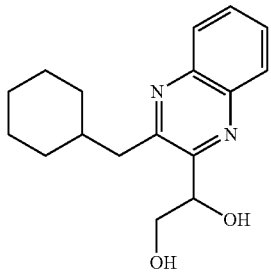 [SMILES: OCC(O)c1nc2ccccc2nc1CC1CCCCC1]

1-(3-(cyclohexylmethyl)quinoxalin-2-yl)ethane-1,2-diol $^1$H NMR (400 MHz, CDCl$_3$) δ ppm=8.15-8.08 (1H, m), 8.08-8.00 (1H, m), 7.84-7.69 (2H, m), 5.27-5.14 (1H, m), 4.58 (1H, br s), 4.11-3.97 (1H, m), 3.85-3.72 (1H, m), 2.94 (2H, d, J=7.1 Hz), 2.87 (1H, br s), 2.15-1.98 (1H, m), 1.80-1.60 (6H, m), 1.33-1.08 (4H, m). $^{13}$C NMR (100 MHz, CDCl$_3$) δ ppm=154.7, 152.8, 142.0, 139.1, 129.9, 129.5, 128.7, 128.3, 70.6, 66.6, 41.6, 38.2, 33.5, 33.2, 26.3, 26.2. HRMS (ESI$^+$) m/z calcd. for C$_{17}$H$_{23}$N$_2$O$_2$ [M+H]$^+$ 287.1760. found 287.1718.

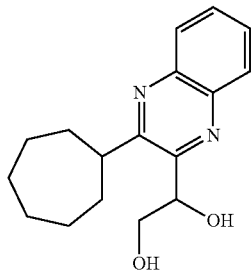 [SMILES: OCC(O)c1nc2ccccc2nc1C1CCCCCC1]

1-(3-cycloheptylquinoxalin-2-yl)ethane-1,2-diol $^1$H NMR (400 MHz, CDCl$_3$) δ ppm=8.13-8.06 (1H, m), 8.06-7.97 (1H, m), 7.80-7.67 (2H, m), 5.28-5.14 (1H, m), 4.71 (1H, br s), 4.10-4.00 (1H, m), 3.82-3.70 (1H, m), 3.29-3.15 (1H, m), 2.22-2.05 (1H, m), 2.00-1.90 (4H, m), 1.82-1.56 (8H, m). $^{13}$C NMR (100 MHz, CDCl$_3$) δ ppm=161.2, 151.7, 142.6, 139.4, 130.2, 129.7, 129.3, 128.7, 70.9, 67.4, 43.3, 35.6, 34.3, 28.5, 28.3, 27.6, 27.5. HRMS (ESI$^+$) m/z calcd. for C$_{17}$H$_{23}$N$_2$O$_2$ [M+H]$^+$ 287.1760. found 287.1723.

While the invention has been particularly shown and described with reference to specific embodiments (some of which are preferred embodiments), it should be understood by those having skill in the art that various changes in form and detail may be made therein without departing from the spirit and scope of the present invention as disclosed herein.

What is claimed is:

1. A compound having the following structure:

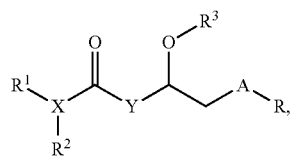

(I)

wherein R and R$^3$ are each are each independently a phosphonate group, sulfonate group, sulfoxide group, or carboxylate group, ii) R is a phosphonate group, sulfonate group, sulfoxide group, or carboxylate group and R$^3$ is a H or keto group, or iii) R$^3$ is a phosphonate group, sulfonate group, sulfoxide group, or carboxylate group and R is a H or keto group, A is selected from the group consisting of: S, NH, CH$_2$, O, CZ$_2$, and CHZ, where Z is a halogen, Y is selected from the group consisting of: CH$_2$, CZ$_2$, and C=O, where Z is a halogen, X is selected from the group consisting of: CH, C—CH$_3$, and N, R$^1$ is selected from the group consisting of: H, C$_1$ to C$_{16}$ substituted or unsubstituted branched alkyl group, C$_1$ to C$_{16}$ substituted or unsubstituted linear alkyl group, C$_1$ to C$_{16}$ heterocyclic ring, and C$_3$ to C$_8$ carbocyclic ring, and R$^2$ is selected from the group of: H and CH$_3$, wherein, optionally, taken together R$^1$—X—R$^2$ form a C$_3$ to C$_8$ carbocyclic ring or heterocyclic ring, and the ring is, optionally, substituted, wherein, optionally, X is CH, R$^1$ is CR$^x$R$^y$, and R$^x$ is H or C$_1$ to C$_{16}$ substituted or unsubstituted linear alkyl group, R$^y$ is H or C$_1$ to C$_{16}$ substituted or unsubstituted linear alkyl group, and the bond between R$^1$ and X is a double bond, wherein, optionally, X is CH, and R$^1$ and X are each bonded to a single O to form an epoxide, wherein, optionally, A is a N, and taken together A and R form a 1,2,5-thiadiazolidin-3-one 1,1-dioxide, wherein if X is CH, then R$^1$ and R$^2$ are not H, and wherein if X is CH, then R$^1$ is not H and R$^2$ is not CH$_3$.

2. The compound of claim 1, wherein the compound has the following structure:

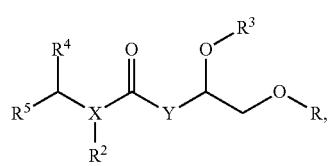

(II)

wherein X is selected from the group consisting of: CH, C—CH$_3$, and N,

Y is selected from the group consisting of: CH$_2$, CZ$_2$, and C=O, where Z is a halogen, R$^2$ is selected from the group consisting of: H and CH$_3$, R$^4$ is selected from the group consisting of: C$_1$ to C$_{16}$ substituted or unsubstituted branched alkyl group, C$_1$ to C$_{16}$ substituted or unsubstituted linear alkyl group, C$_3$ to C$_8$ heterocyclic ring, and C$_3$ to C$_8$ carbocyclic ring, R$^5$ is selected from the group consisting of: C$_1$ to C$_{16}$ substituted or unsubstituted branched alkyl group, C$_1$ to C$_{16}$ substituted or unsubstituted linear alkyl group, C$_3$ to C$_8$ heterocyclic ring, and C$_3$ to C$_8$ carbocyclic ring.

3. The compound of claim 1, wherein the compound has the following structure:

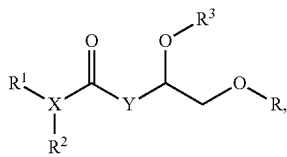
(III)

wherein X is selected from the group consisting of: CH, C—CH₃, and N,
Y is selected from the group consisting of: $CH_2$, $CZ_2$, and C=O, where Z is a halogen, and
wherein taken together $R^1$—X—$R^2$ form a $C_3$ to $C_8$ carbocyclic ring or heterocyclic ring, and the ring is optionally substituted.

4. The compound of claim 1, wherein the compound has the following structure:

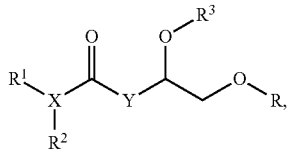
(III)

wherein X is selected from the group consisting of: CH, and N,
Y is selected from the group consisting of: $CH_2$, $CZ_2$, and C=O, where Z is a halogen
$R^1$ is $C_1$ to $C_{16}$ substituted or unsubstituted linear alkyl group,
$R^2$ is H,
wherein, optionally, where X is CH, $R^1$ is $CR^xR^y$, $R^x$ is H or $C_1$ to $C_{16}$ substituted or unsubstituted linear alkyl group, wherein $R^y$ is H or $C_1$ to $C_{16}$ substituted or unsubstituted linear alkyl group, and the bond between $R^1$ and X is a double bond,
wherein, optionally, X is CH, and $R^1$ and X are each bonded to O to form an epoxide, and
wherein when R is H, X is CH, Y is C=O, $R^2$ is H, $R^3$ is H, and $R^1$ is not $C_1$ to $C_6$ unsubstituted linear alkyl group.

5. The compound of claim 1, wherein the compound has the following structure:

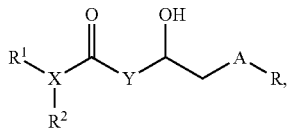
(IV)

wherein X is selected from the group consisting of: CH, C—CH₃, and N,
Y is selected from the group consisting of: $CH_2$, $CZ_2$, and C=O, where Z is a halogen,
A is selected from the group consisting of: NH, $CH_2$, $CF_2$, CHF and O,
R is selected from the group consisting of: phosphonate group, sulfonate group,
sulfoxide group, and carboxylate group,
$R^1$ is selected from the group consisting of: $C_1$ to $C_{16}$ substituted or unsubstituted branched alkyl group, $C_1$ to $C_{16}$ substituted or unsubstituted linear alkyl group, and $C_3$ to $C_8$ carbocyclic ring, and $R^2$ is selected from the group consisting of: H or CH₃,
wherein, optionally, taken together $R^1$ and $R^2$ form a $C_3$ to $C_8$ carbocyclic ring or heterocyclic ring,
wherein the ring is, optionally, substituted,
wherein, optionally, where X is CH, $R^1$ is $CR^xR^y$, $R^x$ is H or $C_1$ to $C_{16}$ substituted or unsubstituted linear alkyl group, wherein $R^y$ is H or $C_1$ to $C_{16}$ substituted or unsubstituted linear alkyl group, and the bond between $R^1$ and X is a double bond, and
wherein, optionally, where X is CH, and $R^1$ and X are each bonded to 0 to form an epoxide,
wherein, optionally, where A is N, and taken together A and R form a 1,2,5-thiadiazolidin-3-one 1,1-dioxide.

6. The compound of claim 1, wherein the compound has one of the following structures:

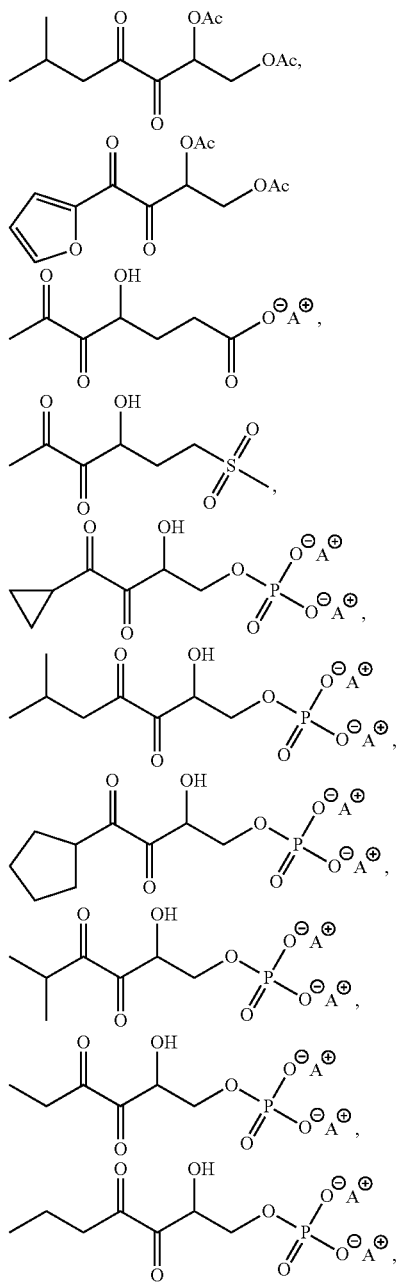

-continued

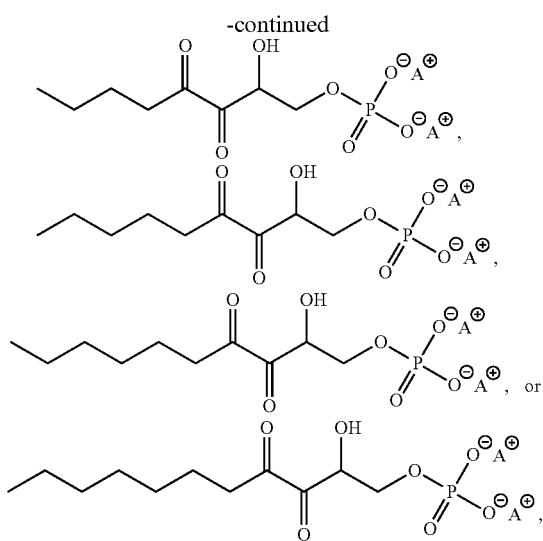

wherein $A^+$ is $H^+$, alkali metal cation, divalent cation, trivalent cation, or ammonium cation.

7. A method for modulating quorum sensing (QS) in a population of bacteria comprising contacting the population of bacteria with a composition comprising a compound having the following structure (I):

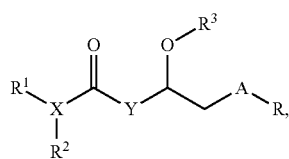
(I)

wherein i) R and $R^3$ are each are each independently a phosphonate group, sulfonate group, sulfoxide group, or carboxylate group, ii) R is a phosphonate group, sulfonate group, sulfoxide group, or carboxylate group and $R^3$ is a H or keto group, or iii) $R^3$ is a phosphonate group, sulfonate group, sulfoxide group, or carboxylate group and R is a H or keto group, A is selected from the group consisting of: S, NH, $CH_2$, O, $CZ_2$, and CHZ, where Z is a halogen;

Y is selected from the group consisting of: $CH_2$, $CZ_2$, and C=O, where Z is a halogen;

X is selected from the group consisting of: CH, C—$CH_3$, and N;

$R^1$ is selected from the group consisting of: H, $C_1$ to $C_{16}$ substituted or unsubstituted branched alkyl group, $C_1$ to $C_{16}$ substituted or unsubstituted linear alkyl group, $C_1$ to $C_{16}$ heterocyclic ring, and $C_3$ to $C_8$ carbocyclic ring, and $R^2$ is selected from the group of: H and $CH_3$, wherein, optionally, taken together $R^1$—X—$R^2$ form a $C_3$ to $C_8$ carbocyclic ring or heterocyclic ring, and the ring is, optionally, substituted, wherein, optionally, X is CH, $R^1$ is $CR^xR^y$, and $R^x$ is H or $C_1$ to $C_{16}$ substituted or unsubstituted linear alkyl group, $R^y$ is H or $C_1$ to $C_{16}$ substituted or unsubstituted linear alkyl group, and the bond between $R^1$ and X is a double bond, wherein, optionally, X is CH, and $R^1$ and X are each bonded to a single O to form an epoxide, wherein, optionally, A is a N, and taken together A and R form a 1,2,5-thiadiazolidin-3-one 1,1-dioxide, and wherein if X is CH, then $R^1$ and $R^2$ are not H, and wherein if X is CH, then $R^1$ is not H and $R^2$ is not $CH_3$.

8. A pharmaceutical preparation comprising a composition a compound having the following structure (I):

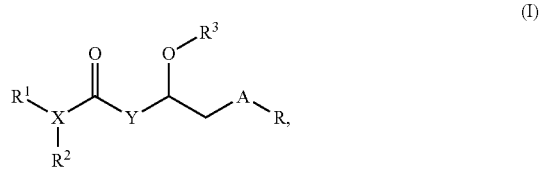
(I)

wherein i) R and $R^3$ are each are each independently a phosphonate group, sulfonate group, sulfoxide group, or carboxylate group, ii) R is a phosphonate group, sulfonate group, sulfoxide group, or carboxylate group and $R^3$ is a H or keto group, or iii) $R^3$ is a phosphonate group, sulfonate group, sulfoxide group, or carboxylate group and R is a H or keto group, A is selected from the group consisting of: S, NH, $CH_2$, O, $CZ_2$, and CHZ, where Z is a halogen;

Y is selected from the group consisting of: $CH_2$, $CZ_2$, and C=O, where Z is a halogen;

X is selected from the group consisting of: CH, C—$CH_3$, and N;

$R^1$ is selected from the group consisting of: H, $C_1$ to $C_{16}$ substituted or unsubstituted branched alkyl group, $C_1$ to $C_{16}$ substituted or unsubstituted linear alkyl group, $C_1$ to $C_{16}$ heterocyclic ring, and $C_3$ to $C_8$ carbocyclic ring, and $R^2$ is selected from the group of: H and $CH_3$, wherein, optionally, taken together $R^1$—X—$R^2$ form a $C_3$ to $C_8$ carbocyclic ring or heterocyclic ring, and the ring is, optionally, substituted, wherein, optionally, X is CH, $R^1$ is $CR^xR^y$, and $R^x$ is H or $C_1$ to $C_{16}$ substituted or unsubstituted linear alkyl group, $R^y$ is H or $C_1$ to $C_{16}$ substituted or unsubstituted linear alkyl group, and the bond between $R^1$ and X is a double bond, wherein, optionally, X is CH, and $R^1$ and X are each bonded to a single O to form an epoxide, wherein, optionally, A is a N, and taken together A and R form a 1,2,5-thiadiazolidin-3-one 1,1-dioxide, and wherein if X is CH, then $R^1$ and $R^2$ are not H, and wherein if X is CH, then $R^1$ is not H and $R^2$ is not $CH_3$.

* * * * *